US012674193B2

(12) United States Patent (10) Patent No.: US 12,674,193 B2
Ali et al. (45) Date of Patent: Jul. 7, 2026

(54) DNAZYME-BASED SENSOR FOR STAPHYLOCOCCUS AUREUS

(71) Applicant: McMaster University, Hamilton (CA)

(72) Inventors: Monsur Ali, Hamilton (CA); Dawn White, Winnipeg (CA); Saeed Mohammadi, Ancaster (CA); John D. Brennan, Dundas (CA); Yingfu Li, Dundas (CA); Alfredo Capretta, Dundas (CA)

(73) Assignee: MCMASTER UNIVERSITY, Hamilton (CA)

( * ) Notice: Subject to any disclaimer, the term of this patent is extended or adjusted under 35 U.S.C. 154(b) by 770 days.

(21) Appl. No.: 17/990,445

(22) Filed: Nov. 18, 2022

(65) Prior Publication Data

US 2023/0257802 A1 Aug. 17, 2023

Related U.S. Application Data

(60) Provisional application No. 63/281,299, filed on Nov. 19, 2021.

(51) Int. Cl.
| | |
|---|---|
| *C12Q 1/68* | (2018.01) |
| *C12Q 1/6837* | (2018.01) |
| *C12Q 1/689* | (2018.01) |

(52) U.S. Cl.
CPC ........... *C12Q 1/6837* (2013.01); *C12Q 1/689* (2013.01)

(58) Field of Classification Search
None
See application file for complete search history.

(56) References Cited

PUBLICATIONS

Fonkwo. Pricing infectious disease. The economic and health implications of infectious diseases. EMBO Reports, vol. 9 Special Issue, published Jul. 2008, pp. S13-S17.
Suhrcke et al. The Impact of Economic Crises on Communicable Disease Transmission and Control: A Systematic Review of the Evidence. PLoS One, vol. 6(6), published Jun. 10, 2011, pp. 1-12.
Uemura et al. Helicobacter Pylori Infection and the Development of Gastric Cancer. The New England Journal of Medicine, vol. 345(11), published Sep. 13, 2001, pp. 784-789.
Mehraj et al. Epidemiology of *Staphylococcus aureus* Nasal Carriage Patterns in the Community. Current Topics in Microbiology and Immunology, vol. 398, published online Jun. 28, 2016, pp. 55-87.
Fitzgerald. Evolution of *Staphylococcus aureus* during human colonization and infection. Infection, Genetics and Evolution, vol. 21, published Jan. 2014, pp. 542-547.
Schmidt et al. Hospital Cost of Staphylococcal Infection after Cardiothoracic or Orthopedic Operations in France: A Retrospective Database Analysis. Surgical Infections, vol. 16(4), published Aug. 1, 2015, pp. 428-435.

Sakr et al. *Staphylococcus aureus* Nasal Colonization: An Update on Mechanisms, Epidemiology, Risk Factors, and Subsequent Infections. Frontiers in Microbiology, vol. 9(2419), published Oct. 8, 2018, pp. 1-15.
Brown et al. *Staphylococcus aureus* colonization: modulation of host immune response and impact on human vaccine design. Frontiers in Immunology, vol. 4(507), published Jan. 8, 2014, pp. 1-20.
Shi et al. Efficacy and safety of cefazolin versus antistaphylococcal penicillins for the treatment of methicillin-susceptible *Staphylococcus aureus* bacteremia: a systematic review and meta-analysis. BMC Infectious Diseases, vol. 18(508), published Oct. 11, 2018, pp. 1-9.
Asgeirsson et al. *Staphylococcus aureus* bacteraemia and endocarditis—epidemiology and outcome: a review. Infectious Diseases, vol. 50(3), published Mar. 2018, pp. 175-192.
Gudiol et al. Pharmacotherapeutic options for treating *Staphylococcus aureus* bacteremia. Expert Opinion on Pharmacotherapy, vol. 18(18), published online Dec. 4, 2017, pp. 1947-1963.
Naber. *Staphylococcus aureus* Bacteremia: Epidemiology, Pathophysiology, and Management Strategies. Clinical Infectious Diseases, vol. 48, published May 15, 2009, pp. S231-S237.
Rubab et al. Biosensors for rapid and sensitive detection of *Staphylococcus aureus* in food. Biosensors and Bioelectronics, vol.(105), published online Jan. 11, 2018, pp. 49-57.
Marquez et al. Foodborne illness outbreak due to *Staphylococcus aureus* among hospital staff following Hurricane Harvey. Infection Control & Hospital Epidemiology, vol. 40(1), published online Nov. 6, 2018, pp. 115-117.
Puah et al. Diverse Profiles of Biofilm and Adhesion Genes in *Staphylococcus aureus* Food Strains Isolated from Sushi and Sashimi. Journal of Food Science, vol. 83(9), published Sep. 2018, pp. 2337-2342.
Lakhundi and Zhang. Methicillin-Resistant *Staphylococcus aureus*: Molecular Characterization, Evolution, and Epidemiology. Clinical Microbiology Reviews, vol. 31(4), published Oct. 2018, pp. 1-103.
Lee et al. Methicillin-resistant *Staphylococcus aureus*. Nature Reviews. Disease Primers, vol. 4(18033), published online May 31, 2018, pp. 1-23.
Templier and Roupioz. On the challenges of detecting whole *Staphylococcus aureus* cells with biosensors. Journal of Applied Microbiology, vol. 123, published online Aug. 13, 2017, pp. 1056-1067.
Zi et al. An improved assay for rapid detection of viable *Staphylococcus aureus* cells by incorporating surfactant and PMA treatments in qPCR. BMC Microbiology, vol. 18(132), published Oct. 11, 2018, pp. 1-8.
Lara et al. Comparison of five methods of extraction of *Staphylococcus aureus* DNA for molecular detection by PCR. Journal of the Brazilian Society of Tropical Medicine, vol. 51(04), published Jul.-Aug. 2018, pp. 528-532.
Wiriyachaiporn et al. Evaluation of a rapid lateral flow immunoassay for *Staphylococcus aureus* detection in respiratory samples. Diagnostic Microbiology and Infectious Disease, vol. 75, published Jan. 2013, pp. 28-36.

(Continued)

*Primary Examiner* — Juliet C Switzer

(74) *Attorney, Agent, or Firm* — SMART & BIGGAR LP

(57) ABSTRACT

This disclosure relates to catalytic nucleic acid probes, biosensors and lateral flow biosensor systems and methods and kits of using the probes, biosensors and lateral flow biosensor systems for detecting microorganisms such as *Staphylococcus aureus*.

20 Claims, 32 Drawing Sheets

Specification includes a Sequence Listing.

(56)          References Cited

PUBLICATIONS

Zschöck et al. Evaluation of six commercial identification kits for the identification of *Staphylococcus aureus* isolated from bovine mastitis. Journal of Applied Microbiology, vol. 98(2), published Feb. 1, 2005, pp. 450-455.

Asante et al. Multidrug-Resistant Coagulase-Negative Staphylococci Isolated from Bloodstream in the Mgungundlovu District of KwaZulu-Natal Province in South Africa: Emerging Pathogens. Antibiotics, vol. 10(198), published Feb. 18, 2021, pp. 1-10.

Essers and Radebold. Rapid and Reliable Identification of *Staphylococcus aureus* by a Latex Agglutination Test. Journal of Clinical Microbiology, vol. 12(5), published Nov. 1980, pp. 641-643.

Papasian and Garrison. Evaluation of a Rapid Slide Agglutination Test for Identification of *Staphylococcus aureus*. Diagnostic Microbiology and Infectious Disease, vol. 33, published Mar. 1999, pp. 201-203.

Ali et al. Fluorogenic DNAzyme Probes as Bacterial Indicators. Angewandte Chemie International Edition, vol. 50, published online Mar. 15, 2011, pp. 3751-3754.

Shen et al. A Catalytic DNA Activated by a Specific Strain of Bacterial Pathogen. Angewandte Chemie, vol. 128, published online Dec. 16, 2015, pp. 2477-2480.

Ali et al. A DNAzyme-Based Colorimetric Paper Sensor for Helicobacter pylori. Angewandte Chemie, vol. 131, published online Jun. 6, 2019, pp. 10012-10016.

Ali et al. A Simple DNAzyme-Based Fluorescent Assay for Klebsiella pneumoniae. ChemBioChem, vol. 20, published online Feb. 11, 2019, pp. 906-910.

Rothenbroker et al. Selection and Characterization of an RNA-Cleaving DNAzyme Activated by Legionella pneumophila. Angewandte Chemie International Edition, vol. 60, published online Jan. 20, 2021, pp. 4782-4788.

McConnell et al. Biosensing with DNAzymes. Chemical Society Reviews, vol. 50, first published Jul. 6, 2021, pp. 8954-8994.

Aguirre et al. A Sensitive DNA Enzyme-Based Fluorescent Assay for Bacterial Detection. Biomolecules, vol. 3, published Aug. 20, 2013, pp. 563-577.

Ali et al. A Printed Multicomponent Paper Sensor for Bacterial Detection. Scientific Reports, vol. 7(12335), published online Sep. 26, 2017, pp. 1-10.

Ting et al. A simple mix-and-read bacteria detection system based on a DNAzyme and a molecular beacon. Chemical Communications, vol. 55, published May 24, 2019, pp. 7358-7361.

Tram et al. Translating Bacterial Detection by DNAzymes into a Litmus Test. Angewandte Chemie International Edition, vol. 53, published online Sep. 11, 2014, pp. 12799-12802.

Liu et al. Target-Induced and Equipment-Free DNA Amplification with a Simple Paper Device. Angewandte Chemie International Edition, vol. 55, published online Jan. 8, 2016, pp. 2709-2713.

Mazumdar et al. Easy-to-use dipstick tests for detection of lead in paints using non-cross-linked gold nanoparticle-DNAzyme conjugates. Chemical Communications, vol. 46, published Jan. 26, 2010, pp. 1416-1418.

Fang et al. Lateral flow nucleic acid biosensor for Cu2+ detection in aqueous solution with high sensitivity and selectivity. Chemical Communications, vol. 46, published Nov. 4, 2010, pp. 9043-9045.

Chen et al. Enzyme-free strip biosensor for amplified detection of Pb2+ based on a catalytic DNA circuit. Chemical Communications, vol. 49, published Dec. 12, 2012, pp. 984-986.

Verhoeven et al. Better Detection of *Staphylococcus aureus* Nasal Carriage by Use of Nylon Flocked Swabs. Journal of Clinical Microbiology, vol. 48(11), published Nov. 2010, pp. 4242-4244.

FIG. 1B

RFD-SA06

ATGCCATCCT ACCAACCACG AAGTACATTT CAAACTCATA ACAATCCATC
GGTTAGGTCC TGGTTGCAAGC TCTTGAACTCG

RFD-SA6T1

ATGCCATCCT ACCAACCACG AAGTACATTT CAAACTCATA ACAATCCATC
GGTTAGGTCC TGGTTGG~~~ ~~~~~~~~~~

RFD-SA6T2

~~~~~~~~~~ ~~~~~CACG AAGTACATTT CAAACTCATA ACAATCCATC
GGTTAGGTCC TGGTTGCAAGC TCTTGAACTCG

RFD-SA6T3

~~~~~~~~~~ ~~~~~CACG AAGTACATTT CAAACTCATA ACAATCCATC
GGTTAGGTCC TGGTTGG~~~ ~~~~~~~~~~

```
DL:  ATGCCATCCTACCAAC-N50-GAGCTCTGAACTCG
FP:  ATGCCATCCTACCAAC
RP1: CGAGTTCAGAGCTC
RP2: A20-L-CGAGTTCAGAGCTC
LT:  GTTGGTAGGATGGCATCTTGGTAGTGAGGTC
FS:  CTATGAACTGACQRFGACCTCACTACCAAG
```

FIG. 3

RFD-SA01:
RFD-SA02:
RFD-SA03:
RFD-SA04:
RFD-SA05:
RFD-SA06:
RFD-SA07:
RFD-SA08:
RFD-SA09:
RFD-SA10:
RFD-SA11:
RFD-SA12:
RFD-SA13:
RFD-SA14:
RFD-SA15:
RFD-SA16:
RFD-SA17:
RFD-SA18:
RFD-SA19:
RFD-SA20:

FIG. 4

RFD-SA6

SEQ ID NO: 45

FIG. 6 (cont'd)

RFD-SA6T1

SEQ ID NO: 46

SEQ ID NO: 47

RFD-SA6T3

SEQ ID NO: 48

Substrate

Cleavage site

FS-RFD-SA6T1:
CTATGAACTG ACQRFGACC TCACTACCAA GATGCCATCC
TACCAACCAC GAAGTACATT TCAAACTCAT AACAATCCAT
CGGTTAGGTC CTGGTTGG    (SEQ ID NO: 38)
FS:
CTATGAACTGACQRFGACCTCACTACCAAG (SEQ ID NO: 10)

FIG. 11A

RFD-SA6T1B: (SEQ ID NO: 30)
CTAATGAGTACCTACCTGTCTTTTTTTTTTTTTCTGGATGATGATCCTATGAACTGAC
QrAFGACCTCACTACCACCAAGATGCCATCCTACCAACCACGAAGTACATTTCA
AACTCATAACAAATCCATCGGTTAGGTCCTGGTTCCTGGTTTTTTTTTTB

FS: CTATGAACTGACQrAFGACCTCACTACCAAG (SEQ ID NO: 10)

TGNP-DNA: AGACAGTAGGTACTCATTAGTTTTTTTTTTTTTSH (SEQ ID NO: 31)

TL-DNA: BTTTTTTTTTTTTAGTCAGTTCATAGGATCATCCAG (SEQ ID NO: 32)

CGNP-DNA: ACCTGGGGGGAGTATTGCGGAGGAAGGTTTTTTSH (SEQ ID NO: 33)

CL-DNA: ACCTTCCTCCGCAATACTCCCCCAGGTTTTTTTB (SEQ ID NO: 34)

FIG. 15A

RFD-SA6T1
CTATGAACTG ACCATCGACCT CACTACCAAG ATGCCATCCT ACCAACCACG AAGTACATTT
CAAACTCATA ACAATCCATC GGTTAGGTCC TGGTTGG (SEQ ID NO: 35)

RFD-SA6T1FRQ
CTATGAACTG ACCATCGACCT CACTACCAAG ATGCCATCCT ACCAACCACG AAGTACATTT
CAAACTCATA ACAATCCATC GGTTAGGTCC TGGTTGG (SEQ ID NO: 36)

RFD-SA6T1R
CTATGAACTG ACTATCGACCT CACTACCAAG ATGCCATCCT ACCAACCACG AAGTACATTT
CAAACTCATA ACAATCCATA GGTTAGGTCC TGGTTGG (SEQ ID NO: 37)

FIG. 15B
FIG. 15C
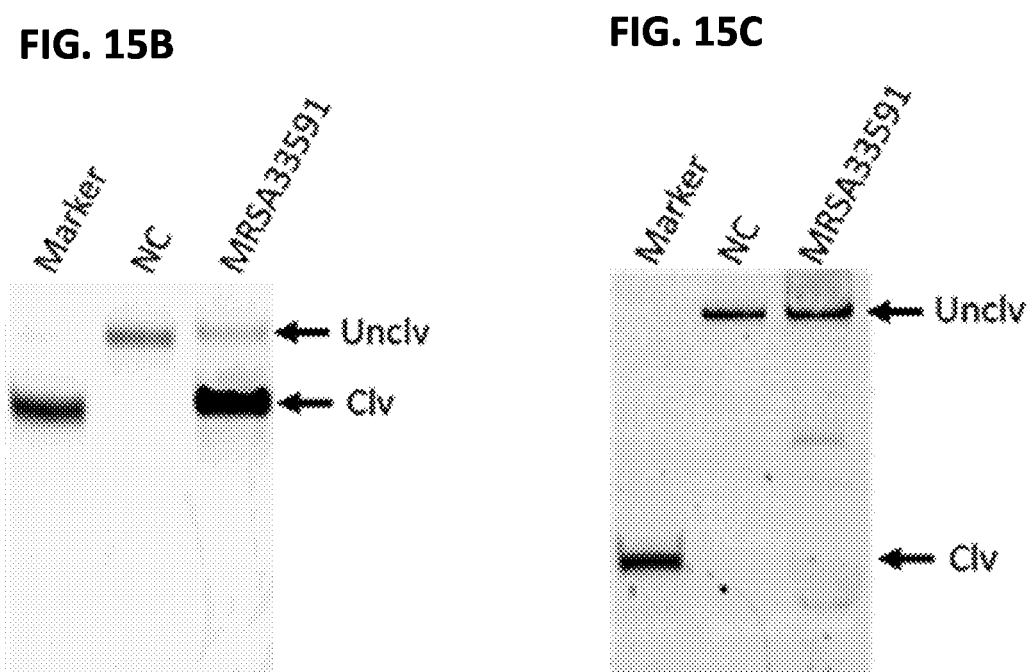
FIG. 15D
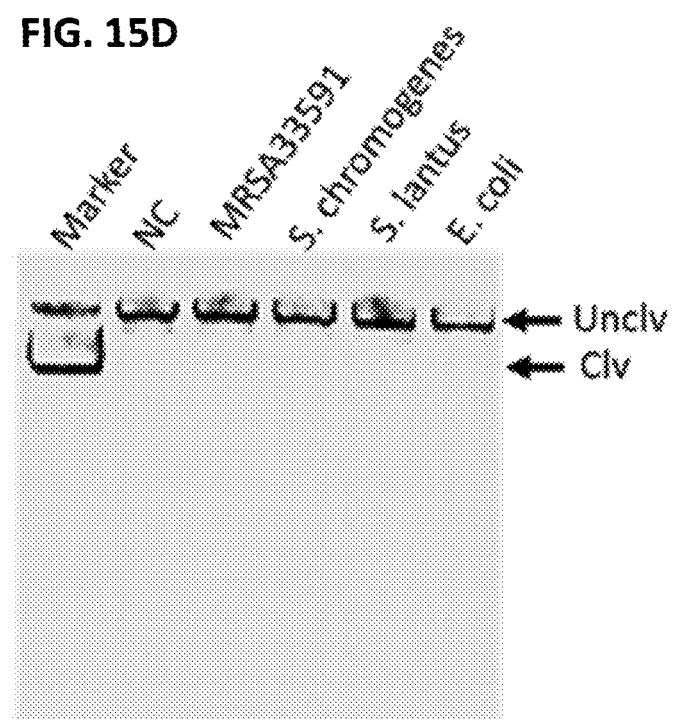

DNAZYME-BASED SENSOR FOR STAPHYLOCOCCUS AUREUS

CROSS REFERENCE TO RELATED APPLICATION

The present disclosure claims priority from U.S. provisional application No. 63/281,299 filed on Nov. 19, 2021, which is hereby incorporated by reference in its entirety.

INCORPORATION OF SEQUENCE LISTING

A computer readable form of the Sequence Listing "3244P93240106US02_93689987_SequenceListing_1.xml" (59,784 bytes), submitted via Patent Center and created on Dec. 11, 2025, is herein incorporated by reference.

FIELD

The present disclosure relates to catalytic nucleic acid probes, biosensors, and lateral flow biosensor systems for detecting pathogenic bacteria, and in particular, for detecting *Staphylococcus aureus*.

BACKGROUND

Infection by pathogenic bacteria remains a major health concern and socioeconomical burden. [1] *Staphylococcus aureus* (SA), a gram positive cocci, is one of the most dangerous and opportunistic human pathogens, causing a variety of infections ranging from benign skin infections to life threatening septicemia. [2] About 30% to 50% of the human population asymptomatically carries this bacteria in the nose, pharynx or on the skin. [3] Being opportunistic, SA infects through injury and surgery often causing SA bacteremia, [4] and is also a major food borne pathogen. [5] Moreover, there are emerging antibiotic resistant SA strains, such as methicillin-resistant SA (MRSA), that have imposed additional burdens owing to more limited treatment options. [6] Therefore, accurate and convenient detection of SA can play a vital role in preventing the transmission of SA and in following the effectiveness of treatment interventions.

Classical methods involving plate culturing have been successfully used for decades for detecting SA. [5a,7] However, while these methods are accurate and sensitive, they require up to 2 days to provide results. More recently, rapid detection techniques such as molecular assays based on polymerase chain reaction (PCR) and antigen assays utilizing enzyme linked immunoassays (ELISA) have been developed. [7c,8] In addition, several rapid tests for SA have been reported, including the MASTASTAPH™ and StaphAurex™ latex agglutination tests, lateral flow tests using antibodies against SA cell-wall peptidoglycan and Staphylococcal enterotoxin-A and B, as well as the coagulase test for SA positive blood samples. [9] While these detection methods can produce results in under 1 h, such tests still require extensive sample processing, multiple assay steps, or suffer from poor sensitivity and specificity. Hence, improved assays and rapid tests are needed to allow simple and rapid diagnosis of SA in a manner that is amenable to use in doctor's offices, long-term care facilities or resource limited settings.

SUMMARY

The present disclosure describes a simple fluorogenic or colorimetric solution or paper-based biosensor capable of providing specific and sensitive detection of SA, a pathogen linked to a variety of infections ranging from benign skin infections to life threatening septicemia. [2] The sensor molecule, an RNA-cleaving DNAzyme derived by in vitro selection, is activated by a target that was present in both MRSA and MSSA (methicillin-sensitive *Staphylococcus aureus*). The colorimetric and fluorogenic biosensor device, designed on the basis of the RNA-cleaving property of the DNAzyme, is capable of delivering sensitive detection of SA in human nasal mucus with minimal sample processing and provides results in minutes. The device remains fully functional for at least 6 months when stored desiccated at room temperature.

This disclosure also relates to a method of detecting a microorganism, for example *Staphylococcus aureus*, in a sample using a biosensor or lateral flow biosensor system, and method and kits for detecting said microorganism.

In accordance with an aspect, provided herein is a catalytic nucleic acid probe for detecting *Staphylococcus aureus*, wherein the catalytic nucleic acid probe comprises a nucleic acid molecule comprising (a) a first nucleic acid region that (i) is capable of binding to a microorganism target, and (ii) has catalytic activity for cleaving a substrate, optionally a detectable substrate, upon contacting with the microorganism target, and (b) a second nucleic acid region comprising the substrate, wherein the catalytic nucleic acid probe comprises a nucleic acid sequence selected from the group consisting of SEQ ID NOs: 2, 1, 3, 4, 11-30, 35-38, and 43, a functional fragment or modified derivative thereof.

In some embodiments, the catalytic nucleic acid probe comprises a nucleic acid sequence selected from the group of SEQ ID NOs: 2, 35-38, and 43, a functional fragment or modified derivative thereof. In some embodiments, the catalytic nucleic acid probe comprises a nucleic acid sequence of SEQ ID NO: 2, a functional fragment or modified derivative thereof.

According to another aspect, there is provided a biosensor comprising the catalytic nucleic acid probe described herein coupled to a solid support, wherein the catalytic nucleic acid probe is an RNA-cleaving catalytic nucleic acid probe for cleaving the substrate that upon cleavage releases a fragment of the second nucleic acid region.

In some embodiments, the solid support comprises a bead surface. In some embodiments, the solid support comprises agarose beads. In some embodiments, the fragment comprises a sensor zone test oligonucleotide binding domain and a test capture zone oligonucleotide binding domain, and wherein the sensor zone test oligonucleotide binding domain is capable of binding to a sensor zone test oligonucleotide by complementarity and the test capture zone oligonucleotide binding domain is capable of binding to a test capture zone oligonucleotide by complementarity.

According to another aspect, there is provided a lateral flow biosensor system for detecting presence of a microorganism target in a test sample comprising:

- a) a sample pad for applying the test sample in a running buffer to initiate a lateral flow process, wherein the catalytic nucleic acid probe is a catalytic nucleic acid probe described herein immobilized to a solid support, wherein the catalytic nucleic acid probe comprises the substrate, wherein the second nucleic acid region comprises a fragment comprising a sensor zone test oligonucleotide binding domain and a test capture zone oligonucleotide binding domain,
- b) a sensor zone comprising a sensor zone test oligonucleotide coupled to a nanoparticle and a sensor zone control DNA oligonucleotide coupled to a nanoparticle, wherein the sensor zone test oligonucleotide is capable of binding by complementarity to the sensor zone test oligonucleotide binding domain in the fragment to form a probe complex, c) a test capture zone comprising an immobilized test capture oligonucleotide, wherein the immobilized test capture oligonucleotide is capable of binding to the probe complex by complementarity to the test capture zone oligonucleotide binding domain in the fragment, d) a control capture zone comprising an immobilized control capture oligonucleotide, wherein the control capture oligonucleotide is capable of binding to the sensor zone control oligonucleotide, and e) an absorbent pad.

In some embodiments, the catalytic nucleic acid probe is comprised in the sample pad. In some embodiments, the solid support comprises agarose beads. In some embodiments, the biosensor is immobilized to the agarose beads by biotin-streptavidin interaction. In some embodiments, the lateral flow biosensor system comprises nitrocellulose paper, a polymer support layer and a hydrophobic material. In some embodiments, the nanoparticle is a gold nanoparticle. In some embodiments, the test capture zone oligonucleotide and the control capture zone oligonucleotide are immobilized on a paper. In some embodiments, the paper is nitrocellulose paper.

According to another aspect, there is provided a method of detecting *Staphylococcus aureus* in a test sample, comprising:

a) contacting the test sample with the biosensor described herein, wherein the catalytic nucleic acid probe comprises a detectable label, b) allowing cleavage of the catalytic nucleic acid probe if a microorganism target is present, thereby releasing the detectable label, and c) measuring a detectable signal if the portion of the catalytic nucleic acid probe comprising the detectable label is released, wherein the RNA cleavage activity of the catalytic nucleic acid probe is activated by a target from *Staphylococcus aureus*.

In some embodiments, the test sample comprises a clinical sample, a clinical matrix comprising methicillin-sensitive *Staphylococcus aureus* (MSSA), nasal mucus, scab exudate, or faeces.

According to another aspect, there is provided a method of detecting *Staphylococcus aureus* in a test sample, comprising:

a) applying the test sample in a running buffer to the sample pad of the lateral flow biosensor system described herein, wherein the test sample comprises an analyte from *Staphylococcus aureus*, and wherein the analyte contacts the immobilized catalytic nucleic acid probe, optionally in the sample pad, and activates the catalytic nucleic acid probe which cleaves the substrate at a ribonucleotide cleavage site and releases the fragment comprising a sensor zone test oligonucleotide binding domain and a test capture zone oligonucleotide binding domain, b) allowing the running buffer to laterally flow into the sensor zone, and then the probe complex laterally flows to the test capture zone and the sensor zone control oligonucleotide laterally flows to the control capture zone, c) allowing the probe complex to produce a signal, d) detecting the signal in the test capture zone, optionally the signal is a color change signal, optionally color is indicative of amount of analyte, e) allowing the sensor zone control oligonucleotide to produce a signal, and f) detecting the signal in the control capture zone, optionally the signal is a color change signal, whereby the signal is indicative of the lateral flow biosensor system functioning correctly.

In some embodiments, the test sample comprises a clinical sample, a clinical matrix comprising methicillin-sensitive *Staphylococcus aureus* (MSSA), nasal mucus, scab exudate, or faeces.

According to another aspect, there is provided a kit for detecting *Staphylococcus aureus*, wherein the kit comprises the lateral flow biosensor system described herein, and instructions for use of the kit. In some embodiments, the kit further comprises at least one of a collection receptacle for storing the test sample, optionally a collection tube, running buffer, optionally HEPES buffer, a container for storing the running buffer, a test sample collector, optionally a swab, a bag optionally a slide lock bag, a label for identifying the test sample, and a package for the kit.

Other features and advantages of the present disclosure will become apparent from the following detailed description. It should be understood, however, that the detailed description and the specific examples, while indicating embodiments of the disclosure, are given by way of illustration only and the scope of the claims should not be limited by these embodiments but should be given the broadest interpretation consistent with the description as a whole.

DRAWINGS

The embodiments of the disclosure will now be described in greater detail with reference to the attached drawings in which:

FIG. 1A shows a schematic of the DNAzyme cleavage and signaling reaction in an exemplary embodiment of the disclosure. The inactive DNAzyme is activated upon binding to the target and cleaves the substrate, producing a high fluorescence signal.

FIG. 1B shows sequences in sequence truncation studies (SEQ ID NOs: 1-4) in an exemplary embodiment of the disclosure. RFD-SA06 (SEQ ID NO: 1) is the full length DNAzyme. The light grey font in both termini denotes the PCR primers for amplification during the selection process. The curved dashed lines in other sequences indicate the deleted nucleotides.

Figures 2A, 2B:
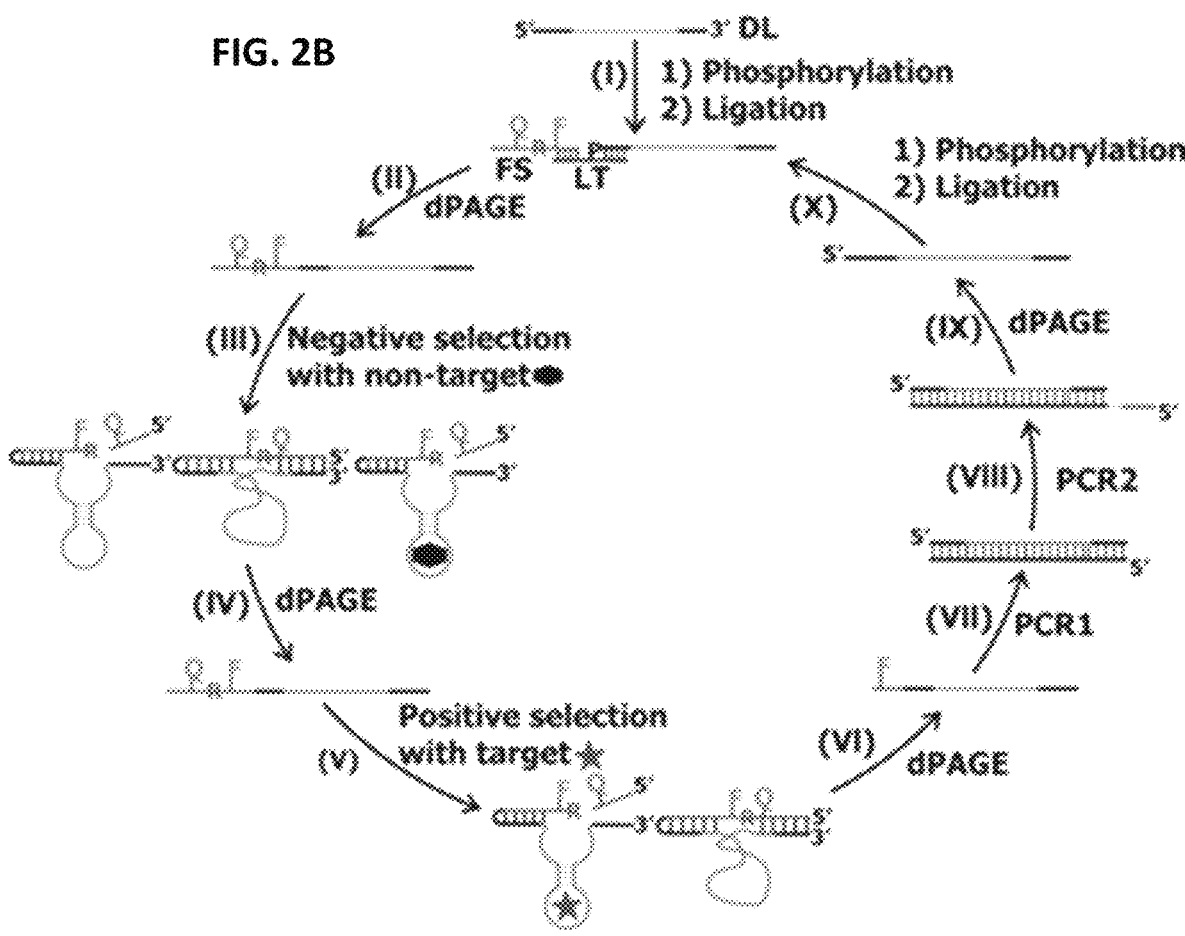

FIG. 2A shows the DNA library including the primer sequences and schematics of in vitro selection in an exemplary embodiment of the disclosure. FIG. 2A shows oligonucleotide sequences used in the in vitro selection process. DL (SEQ ID NO: 5) is the library: N50 represents 50 random nucleotides in the middle flanked by two PCR primer binding arms. FP (SEQ ID NO: 6), RP1 (SEQ ID NO: 7) and RP2 (SEQ ID NOs: 8 & 44) are the forward and reverse primers, respectively. L in RP2 (SEQ ID NOs: 8 & 44) is a glycol linker (IDT spacer 9) with a poly-A tail that generates PCR products with asymmetric lengths to help in purification by dPAGE. FS (SEQ ID NO: 10) is the fluorogenic DNA-RNA substrate: F is fluorescein-dT, R is riboadenosine (designated as the cleavage junction) and Q is dabcyl-dT. LT (SEQ ID NO: 9) serves as a template to enzymatically ligate DL (SEQ ID NO: 5) to FS (SEQ ID NO: 10).

FIG. 2B shows a schematic illustration of in vitro selection in an exemplary embodiment of the disclosure.

Figure 2C:
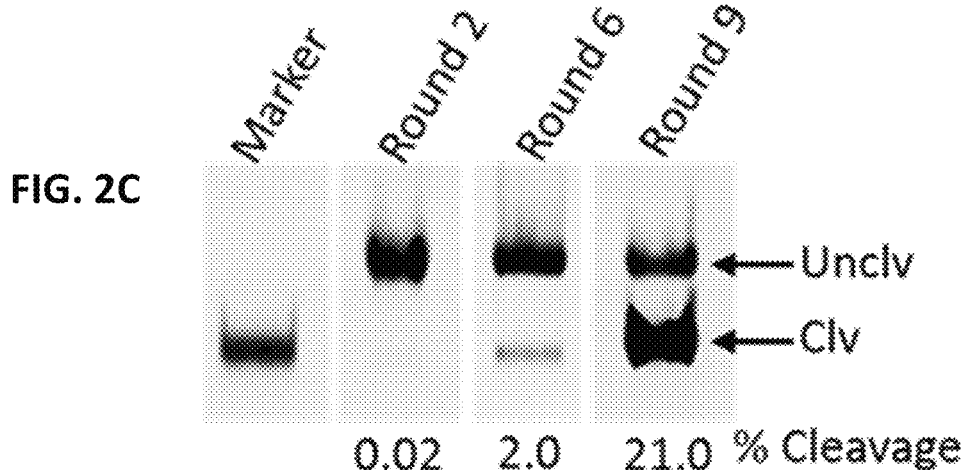

FIG. 2C shows 10% dPAGE images of different rounds of selection showing the progress of the in vitro selection, in an exemplary embodiment of the disclosure. Cleavage product increased with progressing selections rounds which can be seen by the percentage of cleavage in round 2, 6 and 9 (almost no cleavage in round 2, 2% cleavage in round 6 and 21% cleavage in round 9). Unclv: uncleaved full length DL-FS sequences. Clv: shorter sequences after cleavage.

FIG. 3 shows the top 20 sequences (SEQ ID NOs: 1 and 11-29) obtained after sequencing of round 9 populations in an exemplary embodiment of the disclosure. Light grey sequence domains on both ends represent the PCR primers used in PCR amplification during in vitro selection. The black domains in the middle are the DNAzyme sequences evolved from the in vitro selection.

Figure 4:
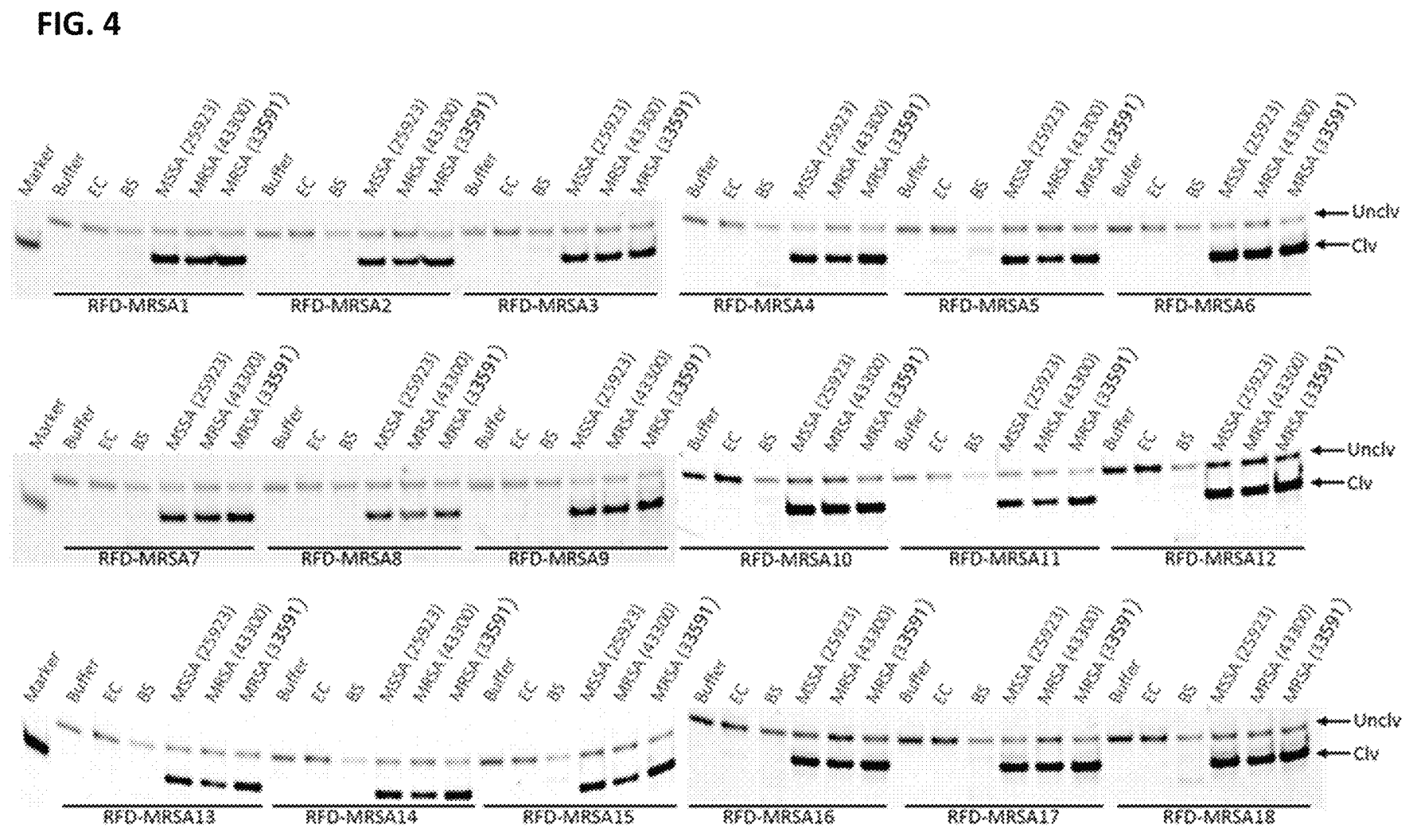

FIG. 4 shows cleavage tests of the top 18 DNAzymes shown in FIG. 3 in an exemplary embodiment of the disclosure. EC: *E. coli*, BS: *Bacillus sphaericus*, MSSA: methicillin-sensitive *S. aureus*, MRSA: methicillin-resistant *S. aureus*. Unclv: Uncleaved full length DNAzyme including the substrate FS. Clv: cleaved shorter fragment.

Figure 5:
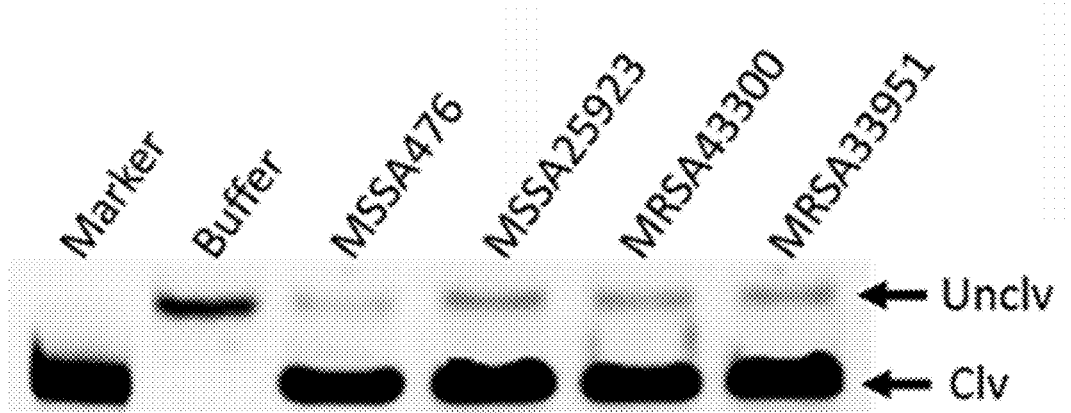
Figure 6:
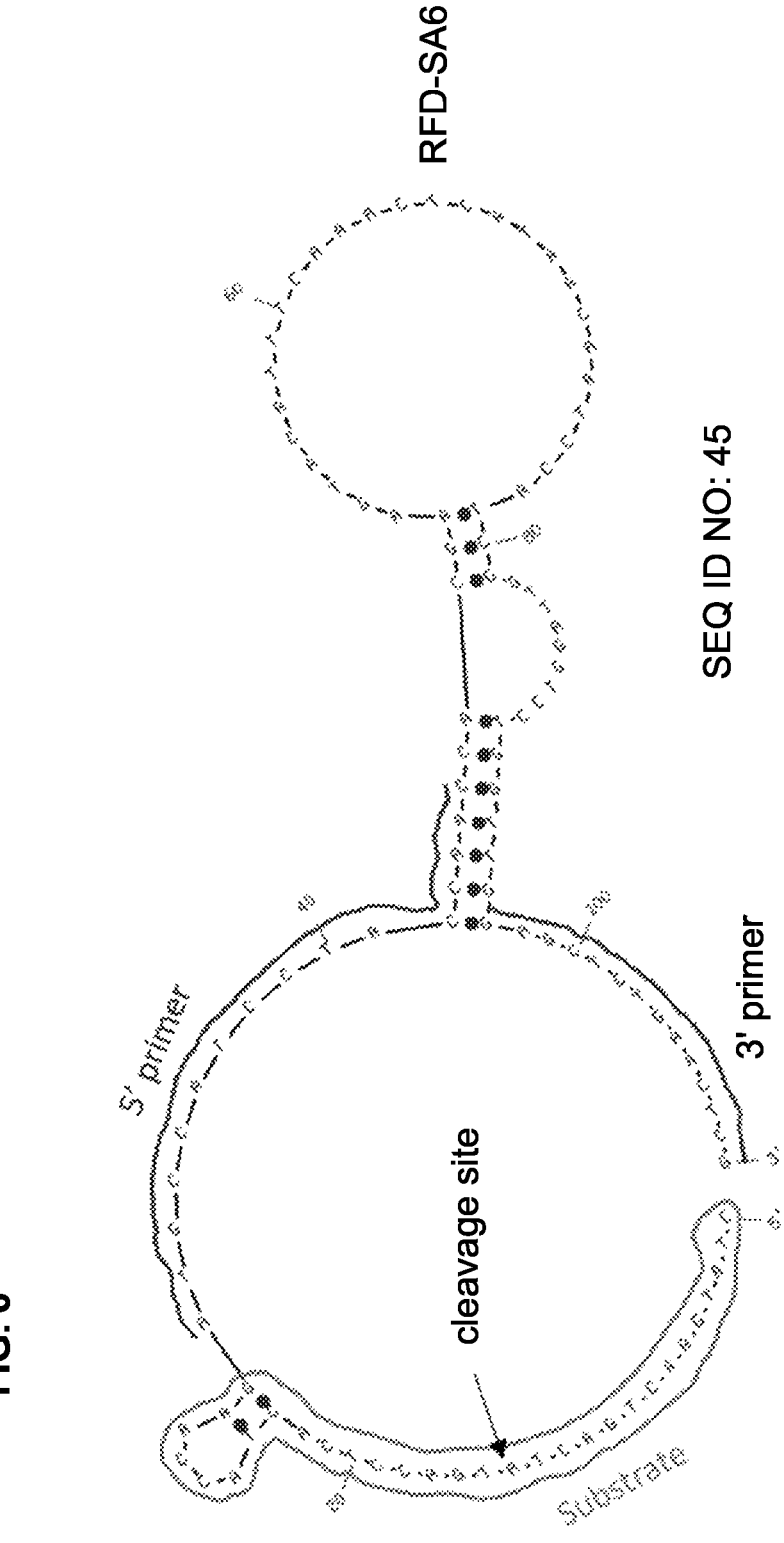
Figure 6:
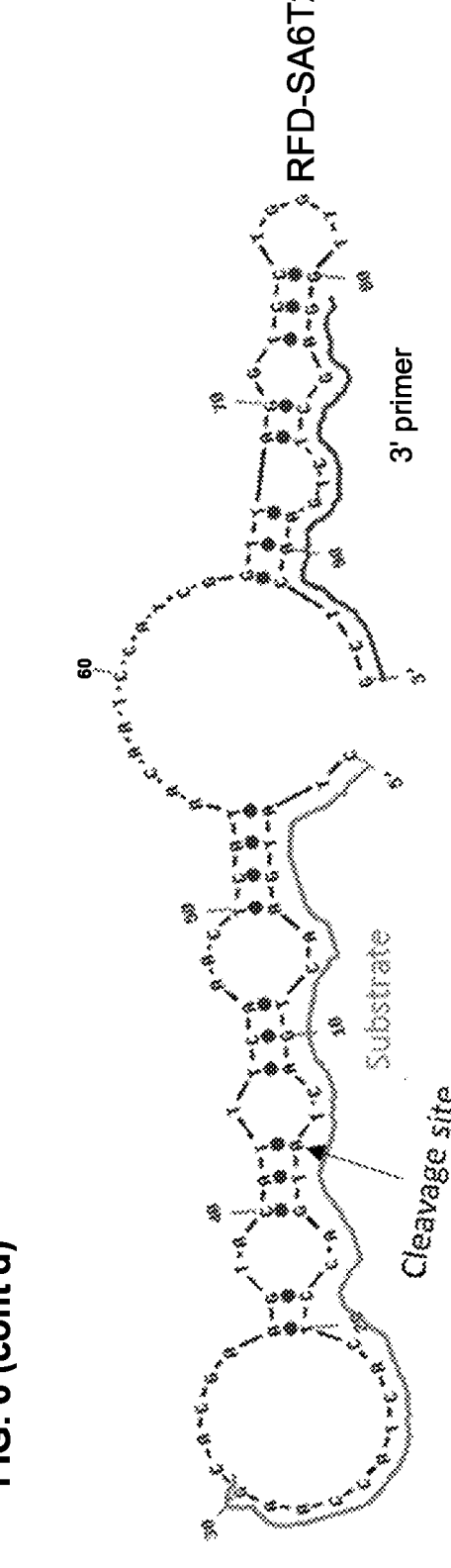
Figure 6:
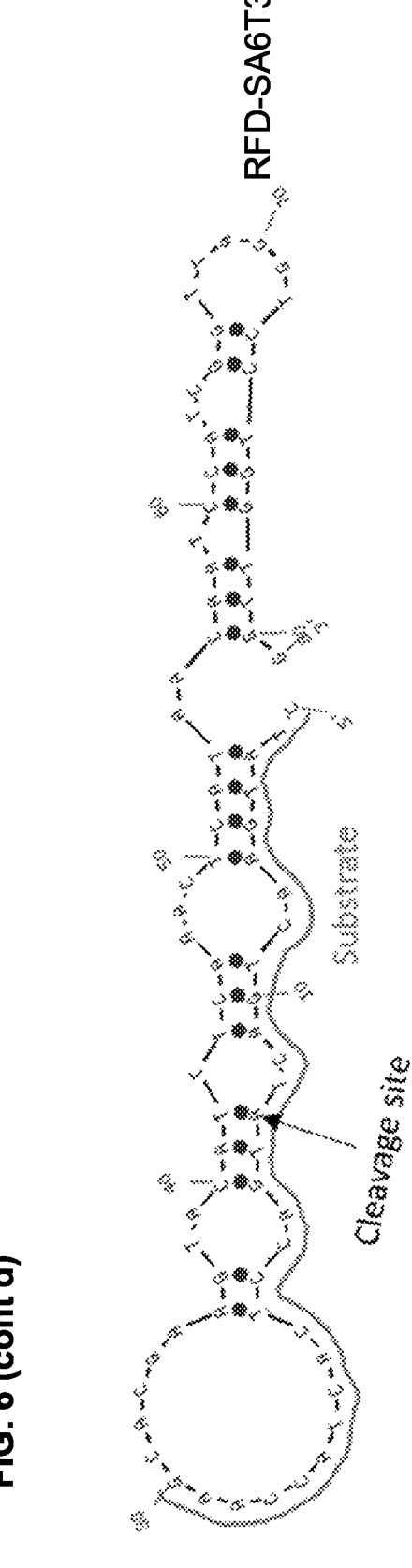

FIG. 5 shows cleavage reactions with each of the 4 strains of *S. aureus* used in the selection experiments in an exemplary embodiment of the disclosure. The DNAzyme was treated with $10^7$ CFU/mL in the selection buffer for 30 min at room temperature and the reaction mixtures were analyzed by 10% dPAGE MSSA: methicillin-sensitive *S. aureus*, MRSA: methicillin-resistant *S. aureus*.

secondary structures FIG. 6 shows predicted (https://www.idtdna.com/Unafold/) of the full length and the truncated DNAzyme shown in FIG. 1B in an exemplary embodiment of the disclosure. The structures of the DNAzymes were obtained including the substrate FS. The substrate and the primers of the library are highlighted and labeled indicating the cleavage site with arrow.

Figure 7A:
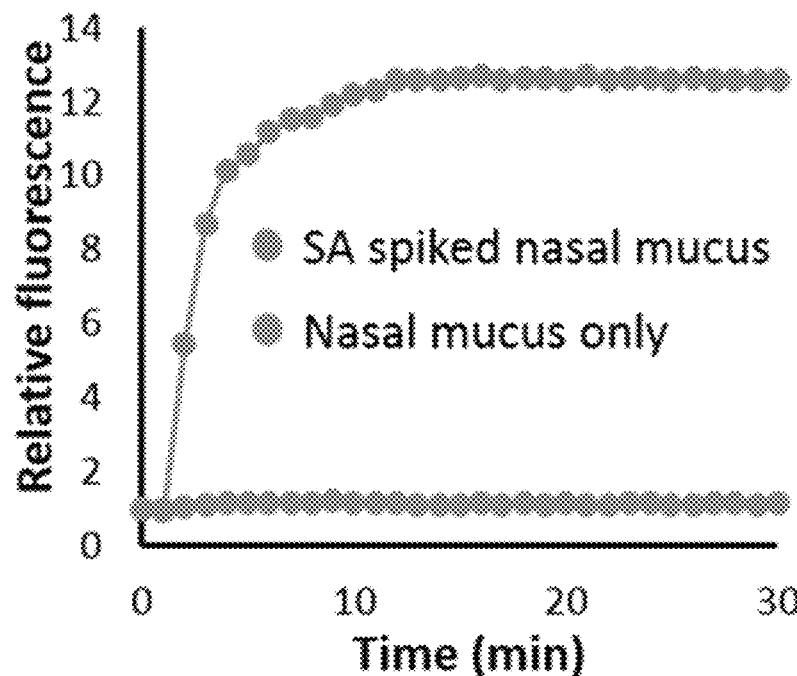

FIG. 7A shows cleavage and fluorescence signaling of RFD-SA6T1 with MRSA spiked into nasal mucus in an exemplary embodiment of the disclosure.

Figure 7B:
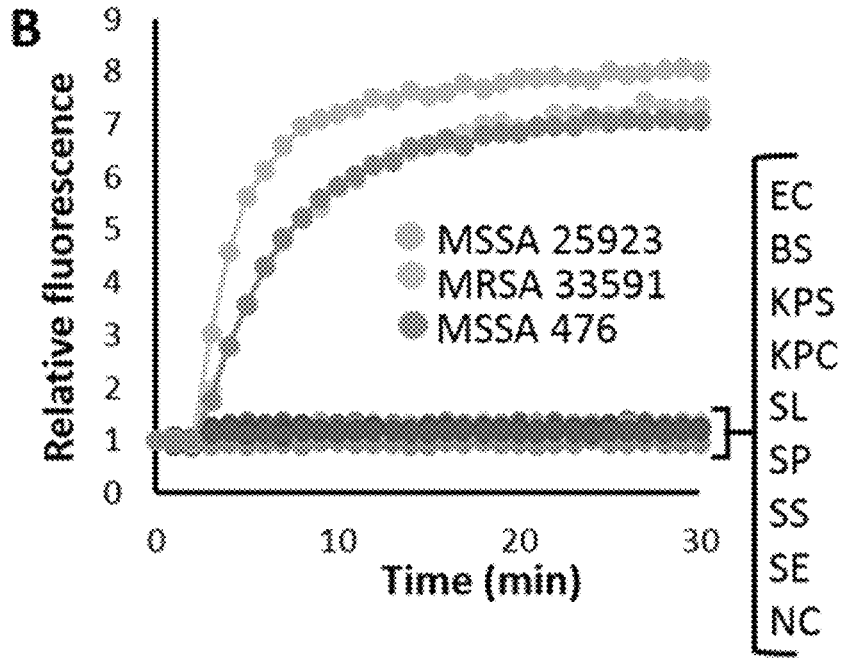

FIG. 7B shows selectivity of RFD-SA6T1 with different bacterial cell lysates in an exemplary embodiment of the disclosure. MSSA: methicillin-sensitive *S. aureus*, MRSA: methicillin-resistant *S. aureus*, EC: *E. coli*, BS: *B. subtilis*, KPS: drug sensitive *K. pneumoniae*, KPC: carbapenem resistant *K. pneumoniae*, SL: *Staphylococcus lentus*, SP: *Staphylococcus pasteuri*, SS: *Staphylococcus saprophyticus*, SE: *Staphylococcus epidermidis*.

Figure 7C:
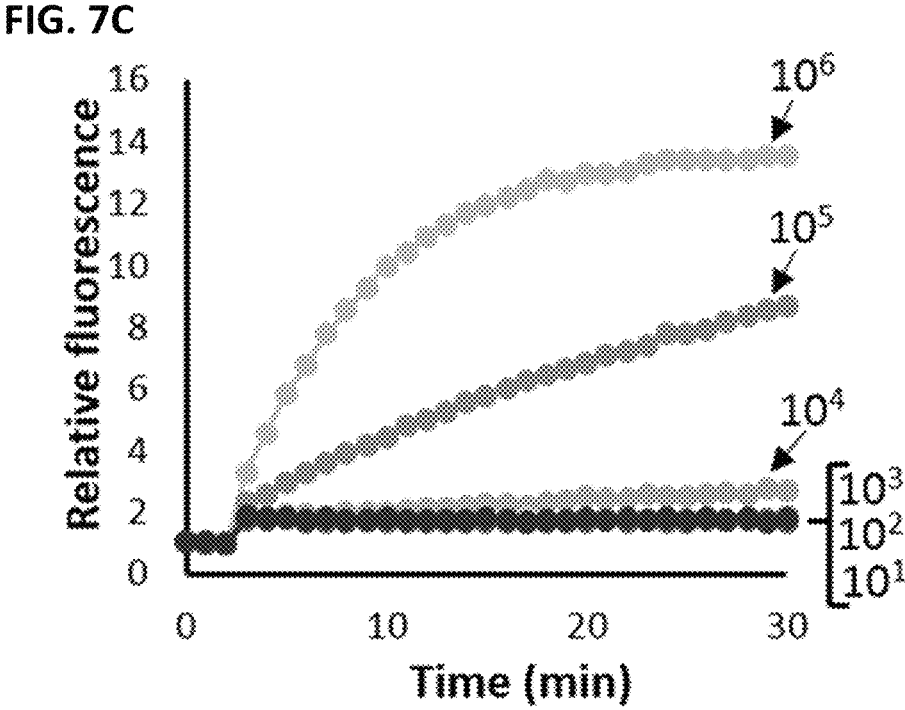

FIG. 7C shows limit of detection (LOD) obtained using fluorescence signal generation in an exemplary embodiment of the disclosure.

Figure 7D:
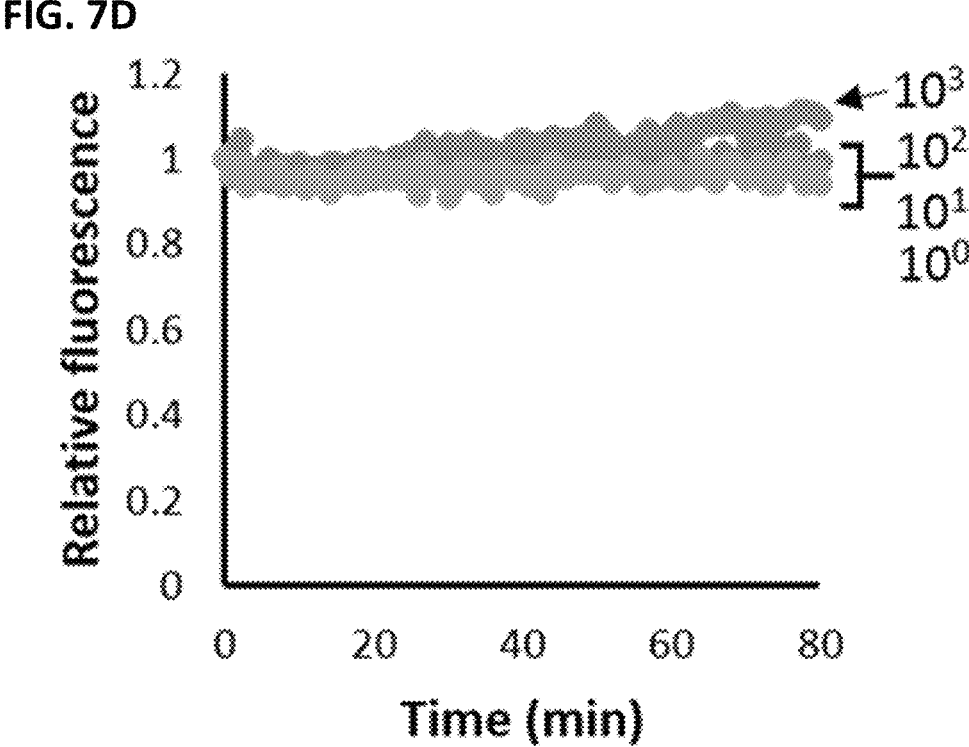

FIG. 7D LOD analysis using a lower number of cells and longer reaction time in an exemplary embodiment of the disclosure.

Figure 7E:
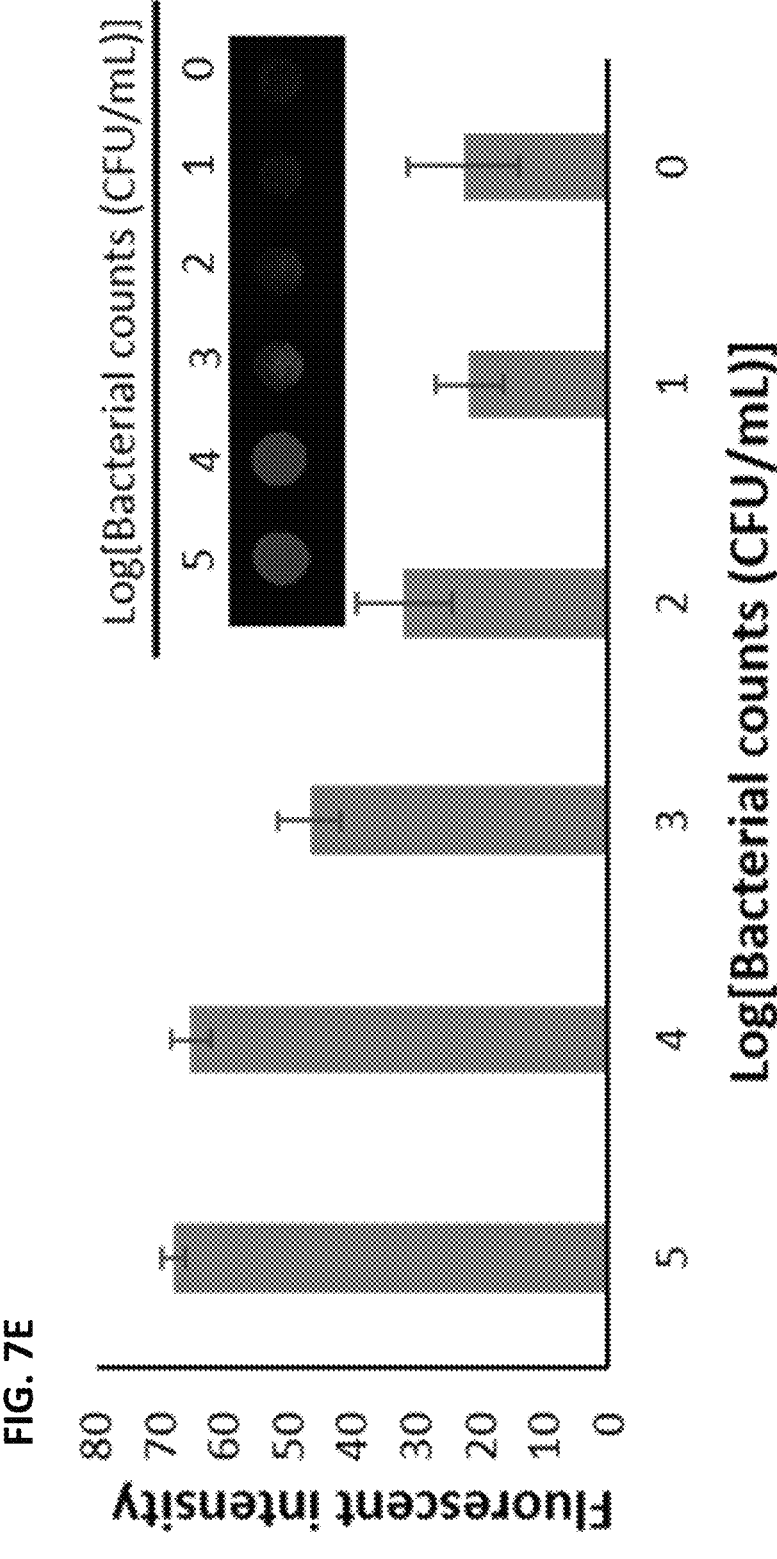

FIG. 7E shows fluorimetric detection of MRSA on a paper microwell plate in an exemplary embodiment of the disclosure.

Figures 8A, 8B:
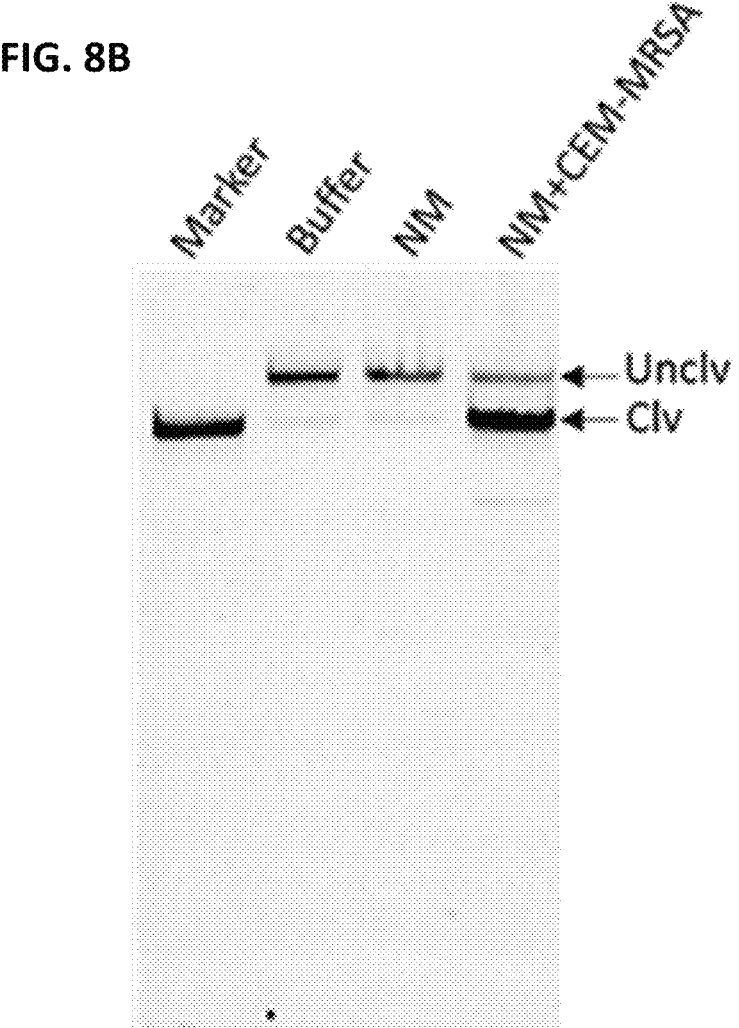

FIG. 8A shows stability test of the DNAzyme in nasal mucus and in crude extra-cellular mixture (CEM)-spiked nasal mucus in an exemplary embodiment of the disclosure. FIG. 8A shows sequences of the full length DNAzyme attached to FS (FS-RFD-SA6T1: SEQ ID NO: 38) and the substrate alone (FS: SEQ ID NO: 10). Q=dabcyl deoxy thymidine: R=adenine ribonucleotide: F=fluorescein deoxythymidine.

FIG. 8B shows stability test of FS-RFD-SA6T1 in buffer, nasal mucus and nasal mucus+CEM-MRSA in an exemplary embodiment of the disclosure. The marker was prepared by treating the full length DNAzyme with NaOH at 90° C. for 10 min. (R: ribo adenosine). Unclv: uncleaved full length DNAzyme, Clv: cleaved DNAzyme, NM: nasal mucus, NM+CEM-MRSA: MRSA CEM spiked nasal mucus.

Figure 8C:
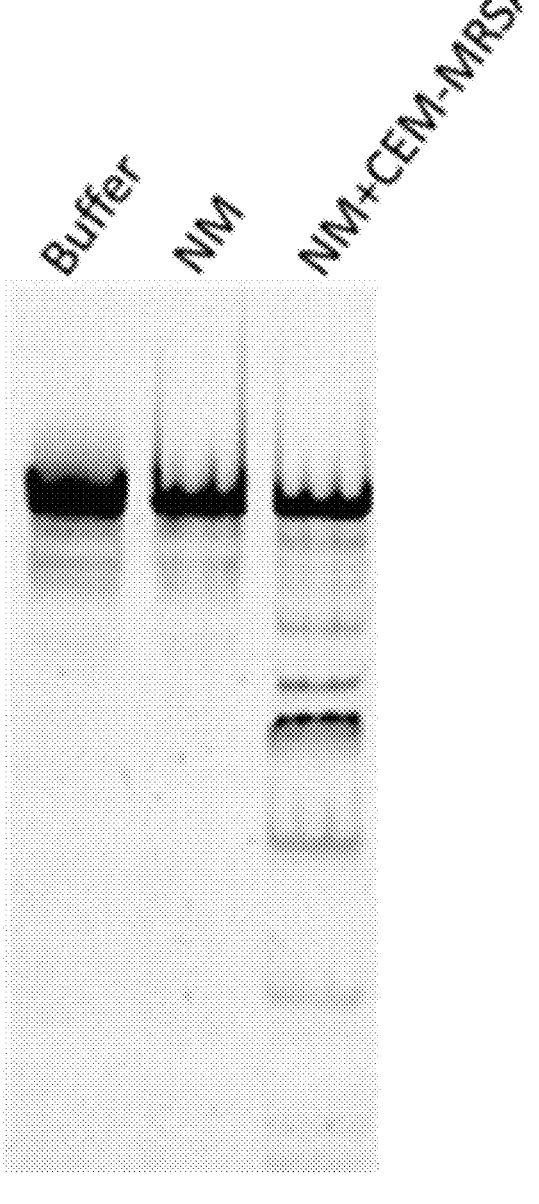

FIG. 8C shows stability test of the substrate (FS) in buffer, nasal mucus alone and nasal mucus+CEM-MRSA, in an exemplary embodiment of the disclosure. 20% nasal mucus was used (with $10^7$ CFU/mL MRSA 33591 in the nasal mucus and with the combination of extra- and intra-cellular mixture (CEM-CIM mixture).

Figure 9:

FIG. 9 shows fluorescent image of 10% dPAGE of the cleavage reaction mixtures of FIG. 7B in an exemplary embodiment of the disclosure. Unclv: Uncleaved full length DNAzyme including the substrate FS. Clv: cleaved shorter fragment. EC: *E. coli*, BS: *B. sphaericus*, KP-ESBL: Extended-spectrum β-*lactamase* producing *K. pneumoniae*, KPC: Carbapenem resistant *K. pneumoniae*, S: *Staphylococcus*, MSSA: methicillin-sensitive *S. aureus*, MRSA: methicillin-resistant *S. aureus*.

Figure 10:
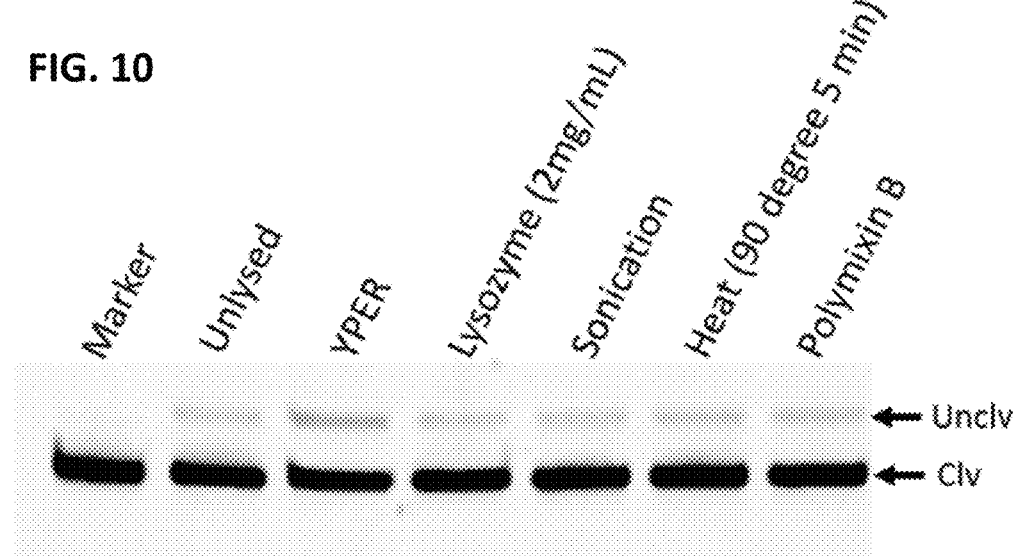

FIG. 10 shows cleavage reactions with intact cells (unlysed MRSA 33591) and after cell lysis using different lysis methods in an exemplary embodiment of the disclosure. Intact cells were incubated in 1× selection buffer (SB) for 20 min without applying any lysis agent or physical agitation. In all other conditions, cells were also incubated for 20 min with the specified lysis agent, except for heating, which was conducted at 90° C. for 5 min. Each solution was then incubated with DNAzyme for 30 min followed by dPAGE analysis. YPER™ is a commercially available cell lysis reagent. Polymixin B is an antibiotic.

FIG. 11A shows sequences of all oligonucleotides (SEQ ID NOs: 10 and 30-34) used for lateral flow device (LFD) fabrication in an exemplary embodiment of the disclosure. Q=dabcyl deoxythymidine: rA=adenine ribonucleotide: F=fluorescein deoxythymidine: B=biotin attached to adjacent thymidine: SH=thiol attached to the adjacent thymidine.

Figure 11B:
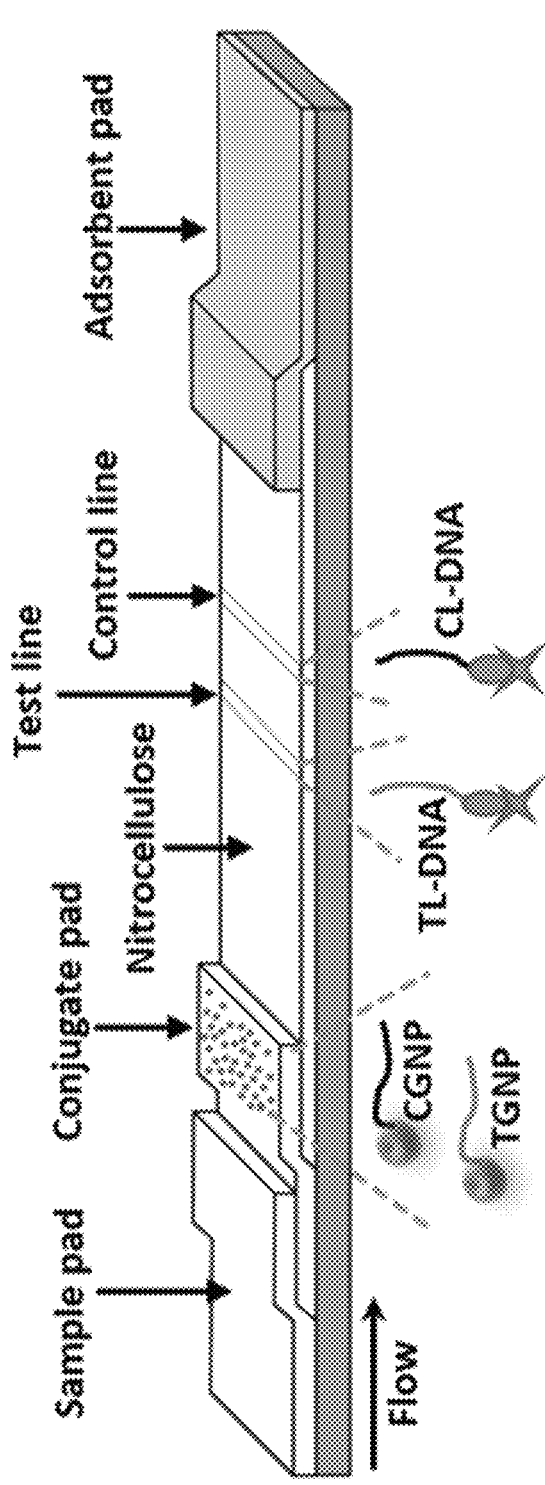

FIG. 11B shows a schematic illustration of the lateral flow device (LFD) in an exemplary embodiment of the disclosure. FIG. 11B shows physical description of the LFD showing the specific regions. Sample pad and conjugate pad are assembled at the bottom of a nitrocellulose strip (NCP: 25×5 cm²). Two different capture DNA oligonucleotides are printed for the test and the control line, respectively. An absorbent pad is attached at the top of the NCP. A mixture of two types of gold nanoparticles with two different oligonucleotides are deposited on the conjugate pad.

Figures 11C, 11D:
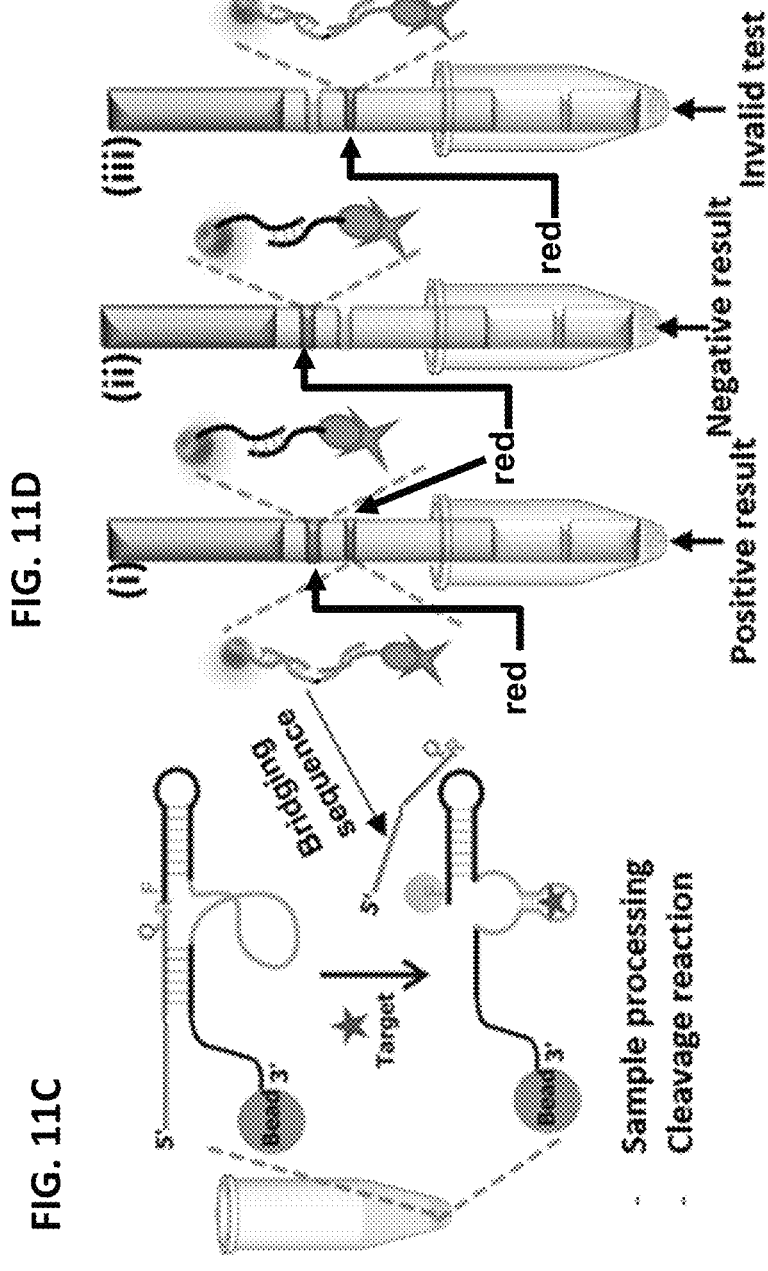

FIG. 11C shows a schematic illustration of the lateral flow device (LFD) in an exemplary embodiment of the disclosure. FIG. 11C shows the DNAzyme-bead complex incubated with the sample to allow the cleavage reaction to occur. The LFD is inserted into the tube such that a portion of the sample pad touches the liquid sample.

FIG. 11D shows a schematic illustration of the lateral flow device (LFD) in an exemplary embodiment of the disclosure. FIG. 11D shows interpretation of the results from the LFD device: (i) If both the test and the control lines turn red, the result is considered positive. (ii) If only the control line turns red, the result is considered negative (no SA in the sample). (iii) If only the test line appears, the result is invalid.

Figure 12:
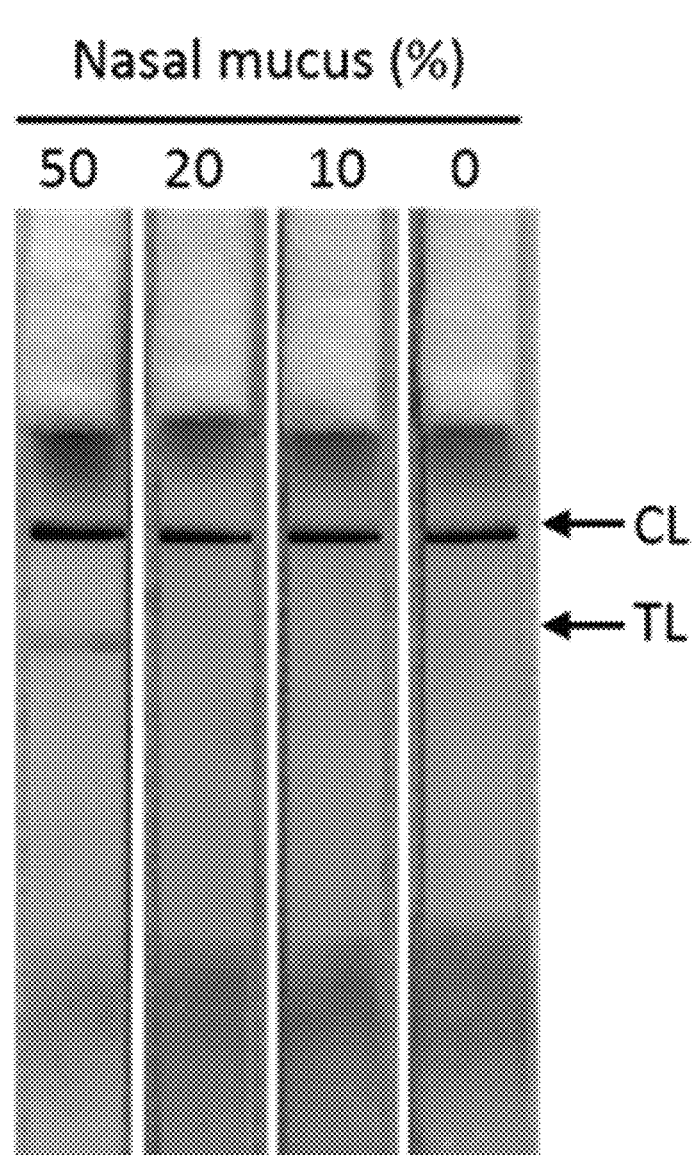

FIG. 12 shows background testing with different concentrations of nasal mucus in an exemplary embodiment of the disclosure. Since 20% nasal mucus did not produce noticeable background, 20% nasal mucus was selected for spiking experiments.

Figure 13:
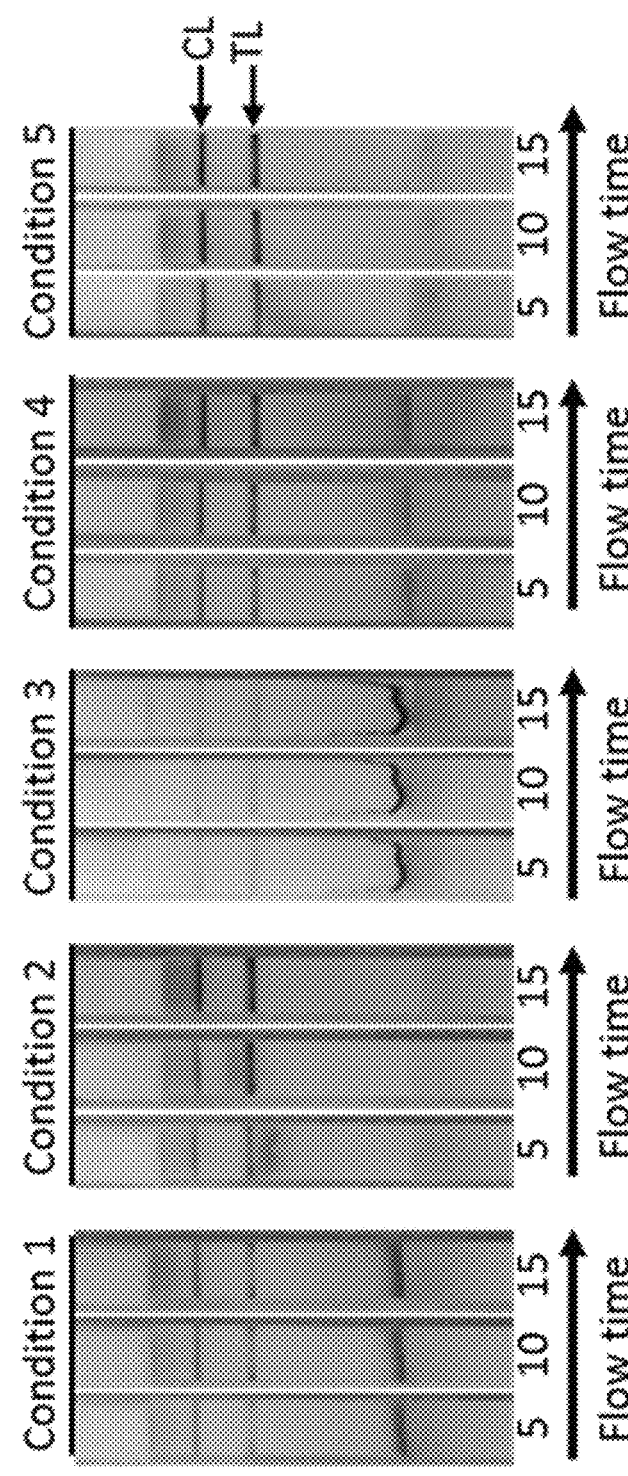

FIG. 13 shows improvement of the LFD running buffer condition in an exemplary embodiment of the disclosure. Condition 1: The cell lysate was in 1×SB. Condition 2: The gold conjugate was immobilized on the conjugate pad without any treatment. 0.1% Tween 20 was added to the cell lysate in 1×SB. Condition 3: The sample pad was soaked in 0.1% Tween 20, dried and attached into the LFD before dipping into the cell lysate. Condition 4: The gold conjugate was immobilized on the conjugate pad without any treatment. The sample pad was soaked in 0.1% SDS, dried and attached into the LFD before dipping into the cell lysate. Condition 5:0.1% Tween 20 was mixed in the cell lysate in 1×SB. The sample pad was soaked in 0.1% SDS, dried and attached into the LFD before dipping into the cell lysate.

Figure 14:
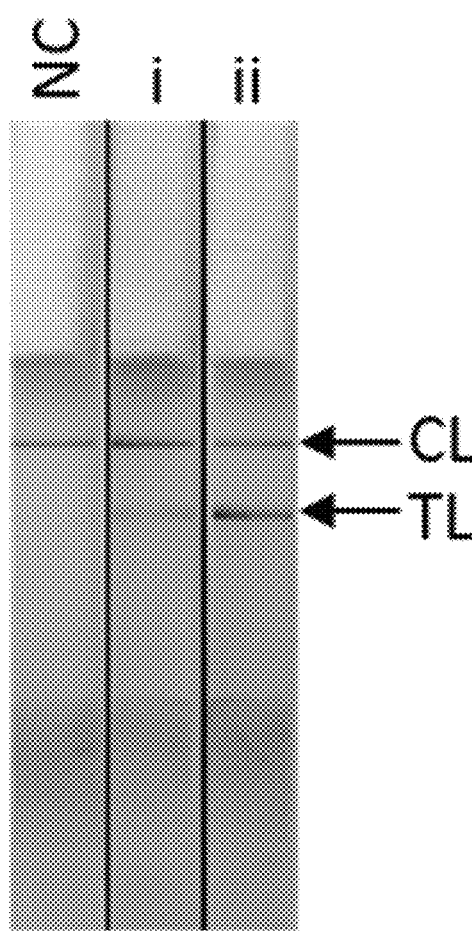

FIG. 14 shows direct cleavage of the DNAzyme on the LFD in an exemplary embodiment of the disclosure. i) DNAzyme was immobilized on the sample pad through streptavidin-agarose beads, dried and attached onto the LFD strip. The strip was directly inserted into the sample (1×SB including 10% cell lysate, 20% nasal mucus and 0.1% Tween20) and the DNAzyme was allowed to cleave during the migration of the targets in the sample. ii) The cleavage reaction of the bead immobilized DNAzyme was carried out in a tube. The LFD strip was then inserted into the tube to run for developing color.

FIG. 15A shows cleavage testing with a modified substrate where the position of fluorophore and quencher have been reversed in an exemplary embodiment of the disclosure. FIG. 15A shows the full length DNAzyme sequence with the original substrate (FS) where the quencher and fluorophore are indicated by Q and F, respectively (RFD-SA6T1: SEQ ID NO: 35) and the full length DNAzyme with the modified substrate [(RFD-SAGT1FRQ: SEQ ID NO: 36); (RFD-SA6TIR (SEQ ID NO: 37)]. Q=dabcyl deoxythymidine: R=adenine ribonucleotide: F=fluorescein deoxythymidine.

FIG. 15B shows cleavage results of RFD-SA6T1 in an exemplary embodiment of the disclosure.

FIG. 15C shows cleavage results of RFD-SAGTIFRQ in an exemplary embodiment of the disclosure.

FIG. 15D shows cleavage results for RFD-SA6TIR where the substrate does not contain the fluorophore and quencher, in an exemplary embodiment of the disclosure.

Figure 16A:
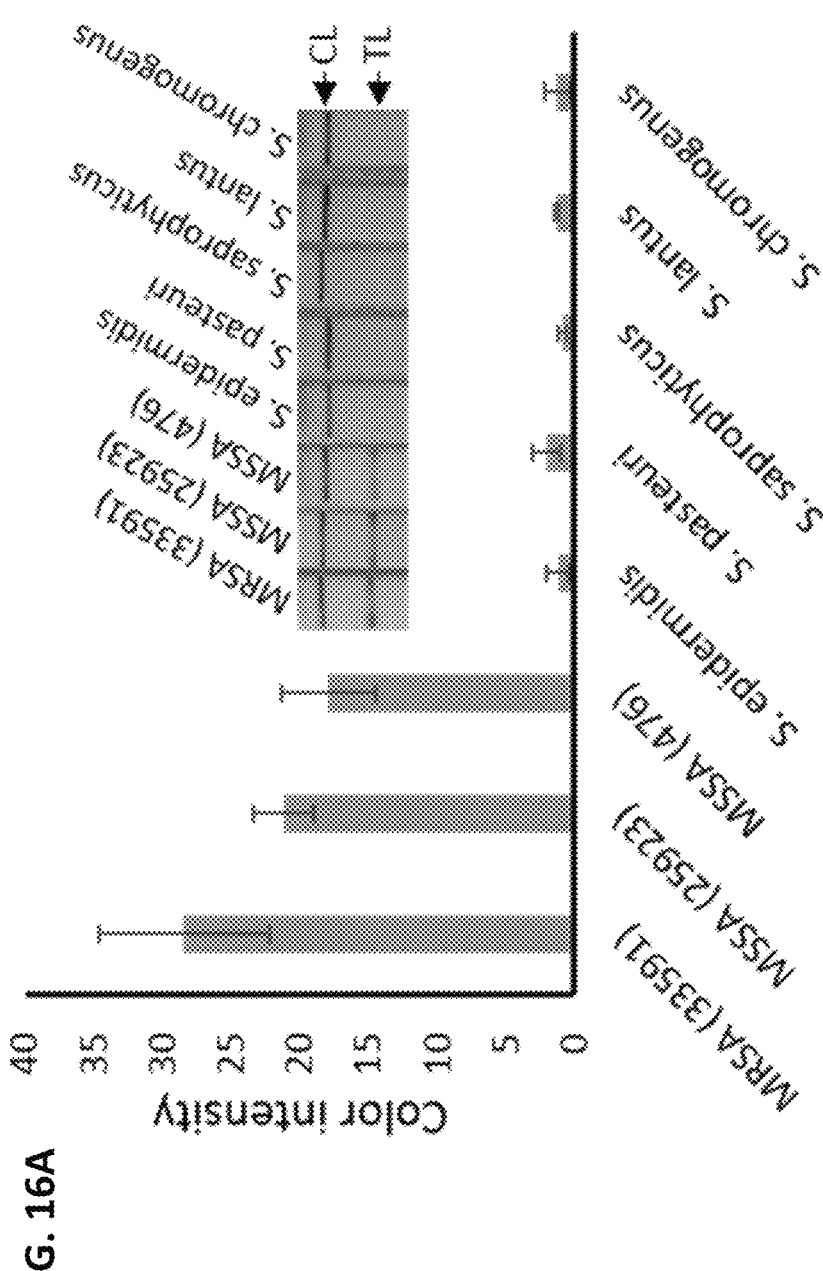

FIG. 16A shows specificity of the LFD against different Staphylococci. 33591, 25923 and 476 represent the ATCC numbers of the SA strains, in an exemplary embodiment of the disclosure. Error bars denote the standard deviation obtained from triplicate experiments for each bacterial species.

Figure 16B:
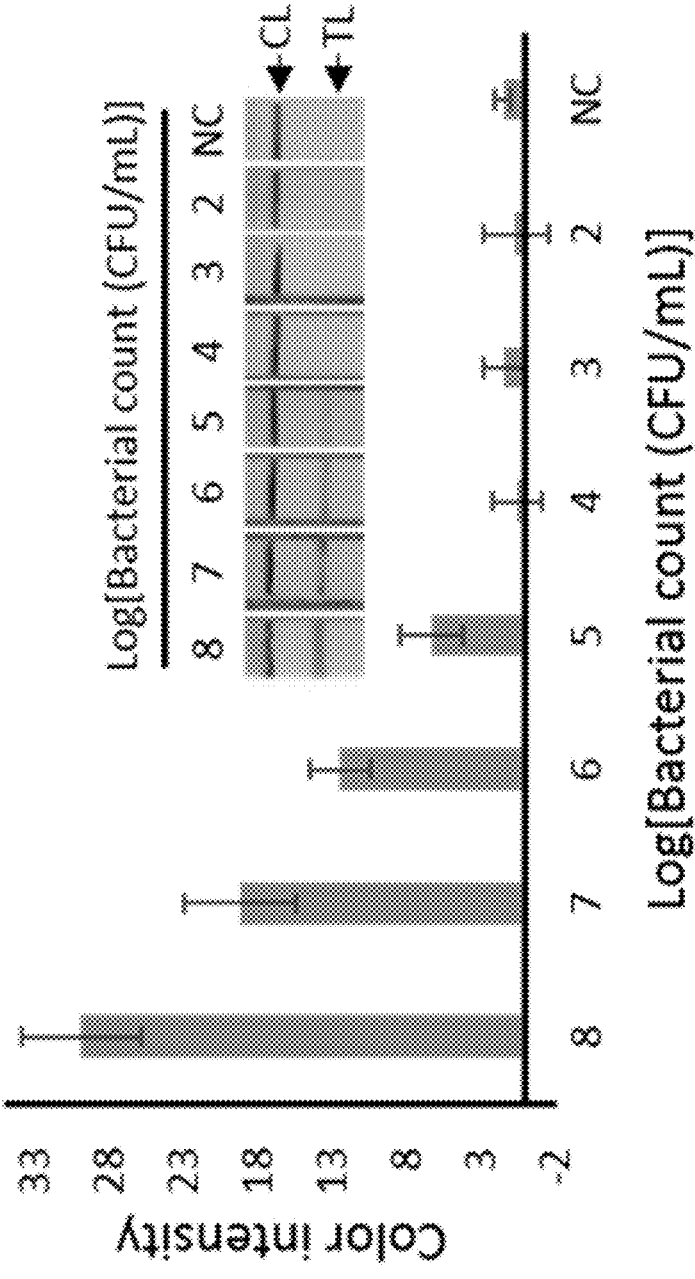

FIG. 16B shows sensitivity of the LFD to detection of MRSA. The sensitivity was investigated using the MRSA 33591 strain. Error bars represent the standard deviation calculated from triplicate experiments of each dilution of bacterial cells.

Figure 17:
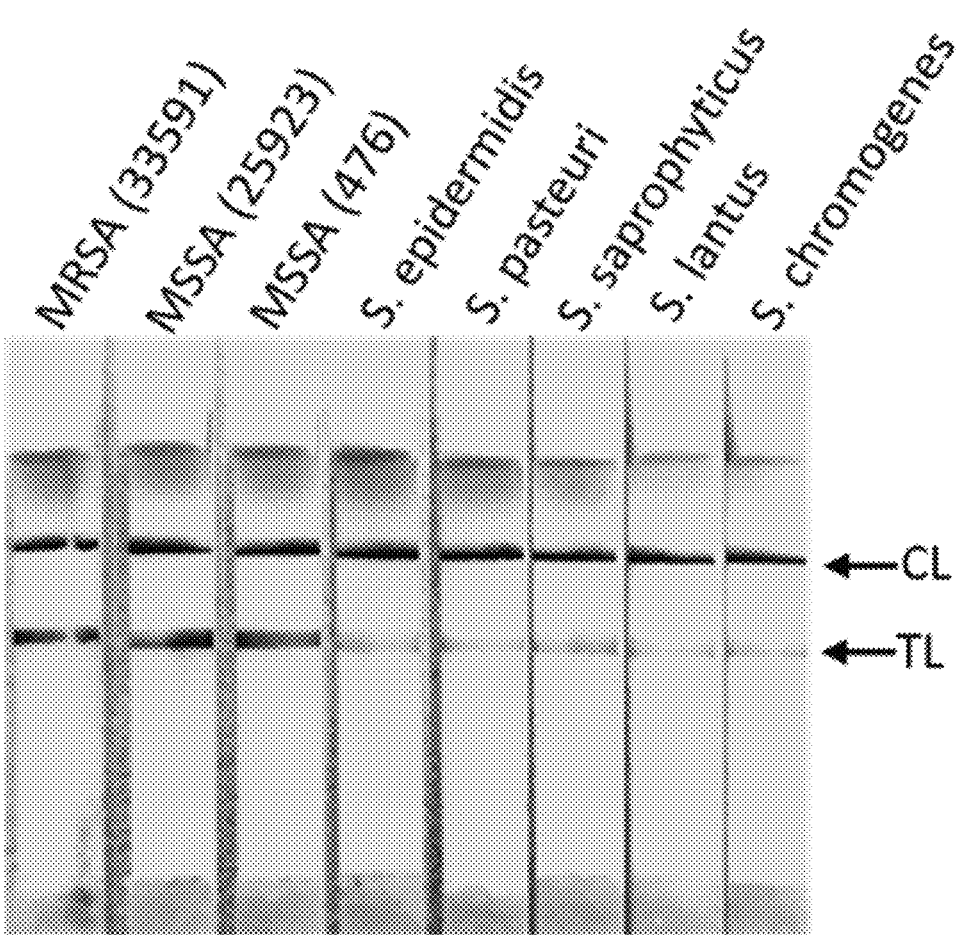

FIG. 17 shows performance of the DNAzyme-based LFD using an extended cleavage reaction time of 30 min, showing increased background in an exemplary embodiment of the disclosure.

Figure 18:
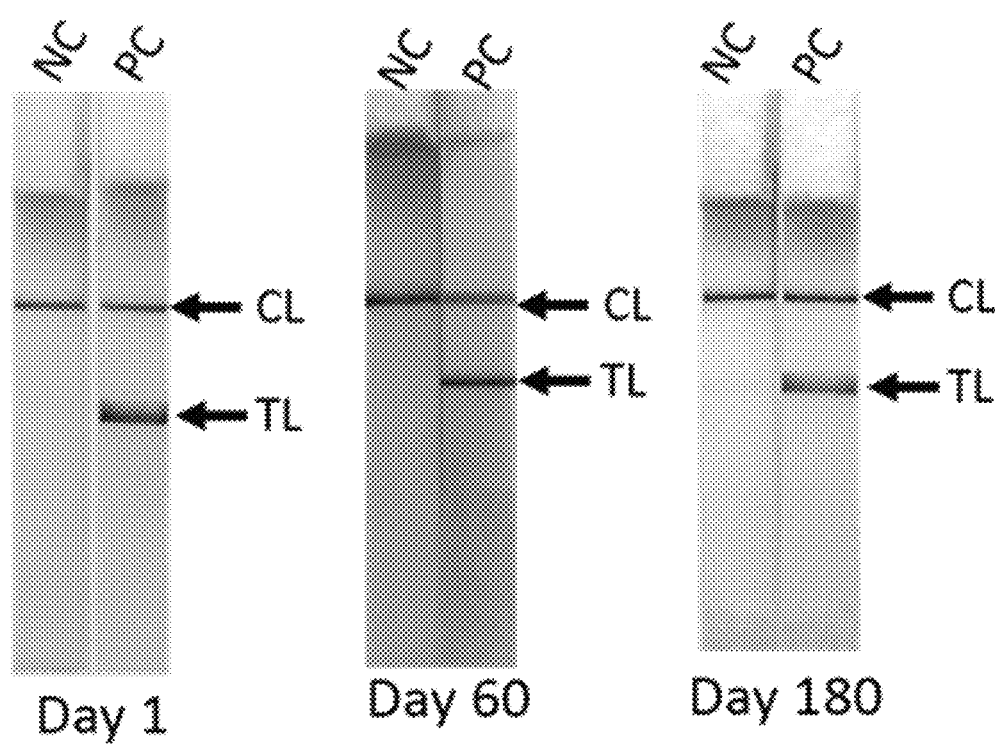

FIG. 18 shows LFD stability at room temperature in a desiccator in an exemplary embodiment of the disclosure. NC: negative control, wherein only buffer was applied in the LFD, PC: positive control wherein a pre-cleaved bridging sequence was added in the running buffer.

Figure 19A:
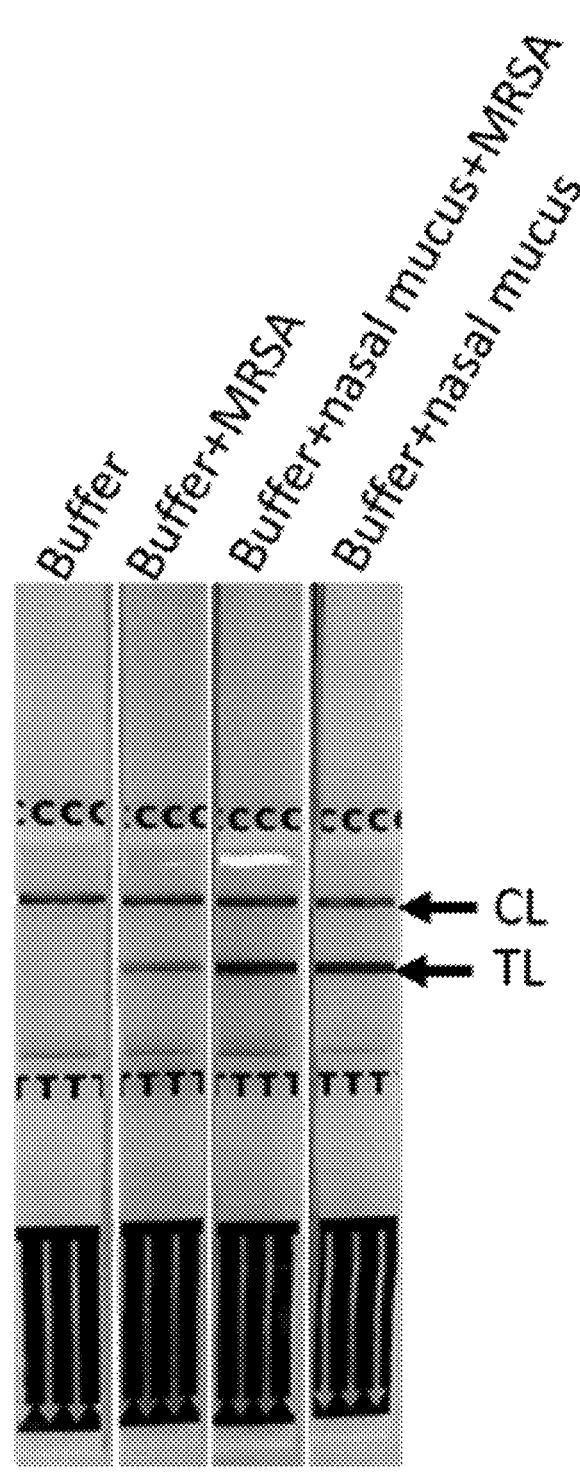

FIG. 19A shows MRSA testing using the Abbot™ Alere™ PBP2a LFD in an exemplary embodiment of the disclosure. FIG. 19A shows performance test in pure buffer and in 20% nasal mucus either in the absence or presence of MRSA cell lysate (~$10^8$ CFU/mL).

Figure 19B:
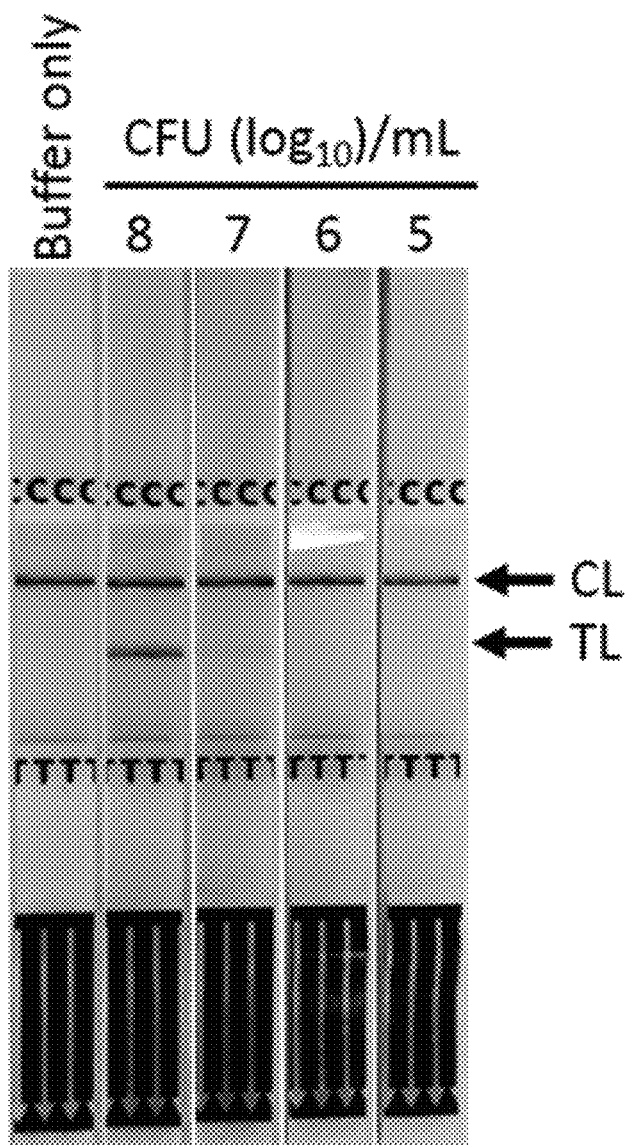

FIG. 19B shows sensitivity test in buffer. Cell lysate equivalent of different cell concentrations were mixed in pure 1×SB and applied to the LFD. CL: control line, TL: test line.

DETAILED DESCRIPTION

I. Definitions

Unless otherwise indicated, the definitions and embodiments described in this and other sections are intended to be applicable to all embodiments and aspects of the present disclosure herein described for which they are suitable as would be understood by a person skilled in the art.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this disclosure, the singular forms "a", "an" and "the" include plural references unless the content clearly dictates otherwise.

In embodiments comprising an "additional" or "second" component, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present. The term "sample" or "test sample" as used herein may refer to any material in which the presence or amount of a target analyte is unknown and can be determined in an assay. The sample may be from any source, for example, any biological (e.g. human or animal samples, including clinical samples), environmental (e.g. water, soil or air) or natural (e.g. plants) source, or from any manufactured or synthetic source (e.g. food or drinks). The sample may be comprised or is suspected of comprising one or more analytes. The sample may be a "biological sample" comprising cellular and non-cellular material, including, but not limited to, tissue samples, saliva, sputum, urine, blood, serum, other bodily fluids and/or secretions. In some embodiments, the sample comprises saliva, sputum, oropharyngeal and/or nasopharyngeal secretions.

The term "target", "analyte" or "target analyte" as used herein may refer to any agent, including, but not limited to, a small inorganic molecule, small organic molecule, metal ion, biomolecule, toxin, biopolymer (such as a nucleic acid, carbohydrate, lipid, peptide, protein), cell, tissue, microorganism and virus, for which one would like to sense or detect. The analyte may be either isolated from a natural source or synthetic. The analyte may be a single compound or a class of compounds, such as a class of compounds that share structural or functional features. The term analyte also includes combinations (e.g. mixtures) of compounds or agents such as, but not limited, to combinatorial libraries and samples from an organism or a natural environment.

The term "nucleic acid" as used herein may refer to a biopolymer comprising monomers of nucleotides, such as deoxyribonucleic acid (DNA), ribonucleic acid (RNA) and other polynucleotides of modified nucleotides and/or nucleotide derivatives, and may be either double stranded (ds) or single stranded (ss). "Modified" bases include, for example, tritiated bases and unusual bases such as inosine. A variety of modifications can be made to DNA and RNA: thus "nucleic acid molecule", "DNA molecule", and "RNA molecule" embrace chemically, enzymatically, or metabolically modified forms. Examples of modified nucleotides which can be used to generate the nucleic acids disclosed herein include xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine or fluorophore and quencher conjugated nucleotides. Alternatively, the nucleic acid molecules can be produced biologically using an expression vector. In some embodiments, modified nucleotides comprise one or more modified bases (e.g. unusual bases such as inosine, and functional modifications to the bases such as amino modifications), modified backbones (e.g. peptide nucleic acid, PNA) and/or other chemically, enzymatically, or metabolically modified forms. The term "functional fragment" as used herein refers to a fragment of the nucleic acid that retains the functional property of the full-length nucleic acid, for example, the ability of the fragment to act as a DNAwyme for detecting a particular analyte, for example, Staphylococcus aureus. In some embodiments, modified nucleotides may contain one or more modified bases (e.g. unusual bases such as inosine, and functional modifications to the bases such as amino), modified backbones (e.g. peptide nucleic acid, PNA) and/or other chemically, enzymatically, or metabolically modified forms.

The term "catalytic nucleic acid", "catalytic nucleic acid probe", "catalytic DNA", "deoxyribozyme", "DNA enzyme", or "DNAzyme" as used herein may refer to a nucleic acid molecule or oligonucleotide sequence that can catalyze or initiate a reaction. DNAzymes may be single-stranded DNA and may include RNA, modified nucleotides and/or nucleotide derivatives. In some embodiments, the DNAzyme is "RNA-cleaving" and catalyzes the cleavage of a particular substrate, for example a nucleic acid sequence comprising one or more ribonucleotides, at a defined cleavage site. In some embodiments, the substrate is a target nucleic acid in a sample. In some embodiments, the DNAzyme cleaves a single ribonucleotide linkage. In some embodiments, the single ribonucleotide linkage is in a nucleic acid sequence wherein the remaining nucleotides are ribonucleotides. In some embodiments, the single ribonucleotide linkage is in a nucleic acid sequence wherein the remaining nucleotides are deoxyribonucleotides. In some embodiments, the DNAzyme cleaves a nucleic acid sequence at a single ribonucleotide linkage thereby producing a nucleic acid cleavage fragment. In some embodiments, the catalytic nucleic acid probe is for detecting Staphylococcus aureus. The term "functional fragment" as used herein refers to the ability of the fragment to act as a catalytic nucleic acid probe for detecting a particular analyte, for example, Staphylococcus aureus, or a microorganism target from Staphylococcus aureus. In some embodiments, the microorganism target comprises a molecule, compound or substance that is present in or on a microorganism, or is generated, excreted, secreted or metabolized by a microorganism. In some embodiments, the microorganism target comprises a molecule, compound or substance that is present in or on Staphylococcus aureus, or is generated, excreted, secreted or metabolized by Staphylococcus aureus.

The term "complementarity" as used herein refers to two structures, such as nucleic acids, each following the lock-and-key principle and aligned antiparallel to each other. Complementarity as used herein referring to nucleic acid includes full or partial complementarity, and complementarity of a portion of the nucleic acid, so long that the complementarity is sufficient to provide a strong enough interaction to prevent dehybridization.

The recitation of numerical ranges by endpoints herein includes all numbers and fractions subsumed within that range (e.g. 1 to 5 includes for example 1, 1.5, 2, 2.75, 3, 3.90, 4, and 5). It is also to be understood that all numbers and fractions thereof are presumed to be modified by the term "about".

It will be understood that any component defined herein as being included can be explicitly excluded by way of proviso or negative limitation, such as any specific compounds or method steps, whether implicitly or explicitly defined herein.

II. Catalytic Nucleic Acid Probes, Biosensors, Lateral Flow Biosensor System, Kits, and Methods Disclosed herein are catalytic nucleic acid probes for detecting Staphylococcus aureus. Catalytic nucleic acid probes were generated by in vitro selection and developed into solution and paper-based fluorescence assays and a rapid colorimetric LFD assay using a catalytic nucleic acid probe as a detection element. In all cases the assay performed robustly, even in nasal mucus samples, and could provide test results in a minimally invasive manner in as little as 30 min. The lateral flow biosensor system described herein has the additional advantages of being portable and simple to use and generating a colorimetric readout that can be analyzed without equipment. As such, the catalytic nucleic acid probes described herein are useful for incorporation in simple and user-friendly paper-based and/or solution-based biosensors or lateral flow biosensor systems for point-of-care or home monitoring of *Staphylococcus aureus* presence, exposure and/or infection.

Accordingly, the present disclosure provides catalytic nucleic acid probe for detecting an analyte, for example, *Staphylococcus aureus*. In some embodiments, the catalytic nucleic acid probe comprises a nucleic acid molecule comprises of (a) a first nucleic acid region that (i) is capable of binding to a microorganism target, and (ii) has catalytic activity for cleaving a substrate, optionally a detectable substrate, upon contacting with the microorganism target, and (b) a second nucleic acid region comprising the substrate. In some embodiments, the catalytic nucleic acid probe comprises or consists of a nucleic acid sequence selected from the group consisting of SEQ ID NOs: 2, 1, 3, 4, 11-30, 35-38, and 43, a functional fragment or modified derivative thereof. In some embodiments, the catalytic nucleic acid probe comprises or consists of a nucleic acid sequence selected from the group of SEQ ID NOs: 2, 35-38, and 43, a functional fragment or modified derivative thereof. In some embodiments, the catalytic nucleic acid probe comprises or consists of a nucleic acid sequence of SEQ ID NO: 2, a functional fragment or modified derivative thereof. In some embodiments, the catalytic nucleic acid probe comprises or consists of a nucleic acid sequence of SEQ ID NO: 1, a functional fragment or modified derivative thereof. In some embodiments, the catalytic nucleic acid probe comprises or consists of a nucleic acid sequence of SEQ ID NO: 3, a functional fragment or modified derivative thereof. In some embodiments, the catalytic nucleic acid probe comprises or consists of a nucleic acid sequence of SEQ ID NO: 4, a functional fragment or modified derivative thereof. In some embodiments, the catalytic nucleic acid probe comprises or consists of a nucleic acid sequence of SEQ ID NO: 11, a functional fragment or modified derivative thereof. In some embodiments, the catalytic nucleic acid probe comprises or consists of a nucleic acid sequence of SEQ ID NO: 12, a functional fragment or modified derivative thereof. In some embodiments, the catalytic nucleic acid probe comprises or consists of a nucleic acid sequence of SEQ ID NO: 13, a functional fragment or modified derivative thereof. In some embodiments, the catalytic nucleic acid probe comprises or consists of a nucleic acid sequence of SEQ ID NO: 14, a functional fragment or modified derivative thereof. In some embodiments, the catalytic nucleic acid probe comprises or consists of a nucleic acid sequence of SEQ ID NO: 15, a functional fragment or modified derivative thereof. In some embodiments, the catalytic nucleic acid probe comprises or consists of a nucleic acid sequence of SEQ ID NO: 16, a functional fragment or modified derivative thereof. In some embodiments, the catalytic nucleic acid probe comprises or consists of a nucleic acid sequence of SEQ ID NO: 17, a functional fragment or modified derivative thereof. In some embodiments, the catalytic nucleic acid probe comprises or consists of a nucleic acid sequence of SEQ ID NO: 18, a functional fragment or modified derivative thereof. In some embodiments, the catalytic nucleic acid probe comprises or consists of a nucleic acid sequence of SEQ ID NO: 19, a functional fragment or modified derivative thereof. In some embodiments, the catalytic nucleic acid probe comprises or consists of a nucleic acid sequence of SEQ ID NO: 20, a functional fragment or modified derivative thereof. In some embodiments, the catalytic nucleic acid probe comprises or consists of a nucleic acid sequence of SEQ ID NO: 21, a functional fragment or modified derivative thereof. In some embodiments, the catalytic nucleic acid probe comprises or consists of a nucleic acid sequence of SEQ ID NO: 22, a functional fragment or modified derivative thereof. In some embodiments, the catalytic nucleic acid probe comprises or consists of a nucleic acid sequence of SEQ ID NO: 23, a functional fragment or modified derivative thereof. In some embodiments, the catalytic nucleic acid probe comprises or consists of a nucleic acid sequence of SEQ ID NO: 24, a functional fragment or modified derivative thereof. In some embodiments, the catalytic nucleic acid probe comprises or consists of a nucleic acid sequence of SEQ ID NO: 25, a functional fragment or modified derivative thereof. In some embodiments, the catalytic nucleic acid probe comprises or consists of a nucleic acid sequence of SEQ ID NO: 26, a functional fragment or modified derivative thereof. In some embodiments, the catalytic nucleic acid probe comprises or consists of a nucleic acid sequence of SEQ ID NO: 27, a functional fragment or modified derivative thereof. In some embodiments, the catalytic nucleic acid probe comprises or consists of a nucleic acid sequence of SEQ ID NO: 28, a functional fragment or modified derivative thereof. In some embodiments, the catalytic nucleic acid probe comprises or consists of a nucleic acid sequence of SEQ ID NO: 29, a functional fragment or modified derivative thereof. In some embodiments, the catalytic nucleic acid probe comprises or consists of a nucleic acid sequence of SEQ ID NO: 30, a functional fragment or modified derivative thereof. In some embodiments, the catalytic nucleic acid probe comprises or consists of a nucleic acid sequence of SEQ ID NO: 35, a functional fragment or modified derivative thereof. In some embodiments, the catalytic nucleic acid probe comprises or consists of a nucleic acid sequence of SEQ ID NO: 36, a functional fragment or modified derivative thereof. In some embodiments, the catalytic nucleic acid probe comprises or consists of a nucleic acid sequence of SEQ ID NO: 37, a functional fragment or modified derivative thereof. In some embodiments, the catalytic nucleic acid probe comprises or consists of a nucleic acid sequence of SEQ ID NO: 38, a functional fragment or modified derivative thereof. In some embodiments, the catalytic nucleic acid probe comprises or consists of a nucleic acid sequence of SEQ ID NO: 43, a functional fragment or modified derivative thereof. In some embodiment, the analyte comprises a molecule, compound or substance that is present in or on *Staphylococcus aureus*, or is generated, excreted, secreted or metabolized by *Staphylococcus aureus*. In some embodiment, the microorganism target comprises a molecule, compound or substance that is present in or on *Staphylococcus aureus*, or is generated, excreted, secreted or metabolized by *Staphylococcus aureus*.

The catalytic nucleic acid probe of the present disclosure can comprise a detectable label. In some embodiments, the detectable label comprises a fluorescent, a colorimetric or other optical probe or electrochemical moiety. In some embodiments, the detectable label is a fluorescent moiety. In some embodiments, the fluorescent moiety is a fluorophore. In some embodiments, the fluorophore is a chemical fluorophore. In some embodiments, the fluorophore is fluorescein. In some embodiments, the fluorescein comprises eosin, calcein, fluorescein amidite (FAM), merbromin, erythrosine, Rose Bengal, or DyLight Fluor, or derivatives thereof, or any other fluorescein that can be incorporated into a DNAwyme. In some embodiments, the fluorophore is 6-Carboxyfluorescein (6-FAM). In some embodiments, the fluorophore is a rhodamine, a coumarin, a cyanine, a TYE™ dye, an ATTO™ dye, an Alexa Fluor® dye, LI-COR IRDyes®, or any other fluorescent dye that can be incorporated into a DNAzyme. In some embodiments, the cyanine is Cy2, Cy3, Cy3B, Cy3.5, Cy5, Cy5.5, or Cy7. In some embodiments, the cyanine is Cy5. In some embodiments, the fluorophore is FAM. The selection of the fluorophore is based upon one or more parameters including, but not limited to, (i) maximum excitation and emission wavelength, (ii) extinction coefficient, (iii) quantum yield, (iv) lifetime, (v) stokes shift, (vi) polarity of the fluorophore and (vii) size.

In some embodiments, the detectable label is a colorimetric moiety. In some embodiments, the colorimetric moiety is urea, nitroblue tetrazolium (NBT), 5-Bromo-4-Chloro-3-Indolyl Phosphate (BCIP), 3,3',5,5'-Tetramethylbenzidine (TMB), 3,3'-Diaminobenzidine (DAB), 2,2'-azino-bis(3-ethylbenzothiazoline-6-sulfonic acid) (ABTS), β-D-glucose, 5-Bromo-4-chloro-3-indolyl-β-galactopyranoside (X-gal), or any other colorimetric moiety that can be incorporated into a DNAzyme. In some embodiments, the colorimetric moiety is catalyzed by an enzymatic moiety. In some embodiments, the enzymatic moiety comprises urease, alkaline phosphatase, horseradish peroxidase, glucose oxidase, β-galactosidase, or any other suitable enzymatic moiety.

Also provided is a nucleic acid comprising or consisting of a sequence selected from the group consisting of SEQ ID NOs: 1-43. In some embodiments, the nucleic acid comprises or consists of a sequence selected from the group consisting of SEQ ID NOs: 2, 1, 3, 4, 11-30, 35-38, and 43. In some embodiments, the nucleic acid comprises or consists of a sequence of SEQ ID NO: 2. In some embodiments, the nucleic acid comprises or consist of a sequence shown in Table 1.

TABLE 1

Sequences.

| SEQ ID NO: | Identifier | Sequence |
|---|---|---|
| 1 | RFD-SA6 (aka RFD-SA06) | ATGCCATCCT ACCAACCACG AAGTACATTT CAAACTCATA ACAATCCATC GGTTAGGTCC TGGTTGGAGC TCTGAACTCG |
| 2 | RFD-SA6T1 | ATGCCATCCT ACCAACCACG AAGTACATTT CAAACTCATA ACAATCCATC GGTTAGGTCC TGGTTGG |
| 3 | RFD-SA6T2 | CACG AAGTACATTT CAAACTCATA ACAATCCATC GGTTAGGTCC TGGTTGGAGC TCTGAACTCG |
| 4 | RFD-SA6T3 | CACG AAGTACATTT CAAACTCATA ACAATCCATC GGTTAGGTCC TGGTTGG |
| 5 | DL | ATGCCATCCTACCAAC-N50-GAGCTCTGAACTCG |
| 6 | FP | ATGCCATCCTACCAAC |
| 7 | RP1 | CGAGTTCAGAGCTC |
| 8 & 44 | RP2 (Reverse Primer 2: SEQ ID NO: 8 & 44 linked by "L" glycol linker) | AAAAAAAAAA AAAAAAAAAA-L-CGAGTTCAGAGCTC (SEQ ID NO: 8-AAAAAAAAAA AAAAAAAAAA) (SEQ ID NO: 44-CGAGTTCAGAGCTC) |
| 9 | LT | GTTGGTAGGATGGCATCTTGGTAGTGAGGTC |
| 10 | FS | CTATGAACTGACQRFGACCTCACTACCAAG |
| 11 | RFD-SA1 (aka RFD-SA01) | ATGCCATCCTACCAACACAACCAAGAGCTGCTTGTCAGTGA TTCATAAAGGCTCGGTGATGTCTAGGAGCTCTGAACTCG |
| 12 | RFD-SA2 (aka RFD-SA02) | ATGCCATCCTACCAACCCAAGTGGTCCAGTGCGTCGTTCAT TCATCTTGCGTGACTGTCTCACTGGAGCTCTGAACTCG |
| 13 | RFD-SA3 (aka RFD-SA03) | ATGCCATCCTACCAACCATGAGGAAGACGTAGTGTTAGTTC ATCCCTGGCACACTGTGACGTCTCGGAGCTCTGAACTCG |
| 14 | RFD-SA4 (aka RFD-SA04) | ATGCCATCCTACCAACACGGCGTAAGTTACACAAGAGTTCT TCATGGCATTAGCTGGTCTCCGTGGGAGCTCTGAACTCG |
| 15 | RFD-SA5 (aka RFD-SA05) | ATGCCATCCTACCAACACCACAAGCTCACCGTCAGTTTTGA AATATTGCAATTGGGTGCAGTCTGGGAGCTCTGAACTCG |
| 16 | RFD-SA7 (aka RFD-SA07) | ATGCCATCCTACCAACCATAATGTCCCAGGTGTCAGCGAGT AATAAGTCATCTAAAGGTCTCCTGGGAGCTCTGAACTCG |

TABLE 1-continued

Sequences.

| SEQ ID NO: | Identifier | Sequence |
|---|---|---|
| 17 | RFD-SA8 (aka RFD-SA08 | ATGCCATCCTACCAACCACGAGCGCAAGTGTCAATCATTAA TCCTTGGCATGCATGAGCGTCCCTGGAGCTCTGAACTCG |
| 18 | RFD-SA9 (aka RFD-SA09 | ATGCCATCCTACCAACCACCAACAACAGCCGTCAGGTTATG TGCGCATCGTGAGGCTCTGCTGTTGGAGCTCTGAACTCG |
| 19 | RFD-SA10 | ATGCCATCCTACCAACCCAGAGCCACAAGTGTCAGTCTCAT TTTTGCTCGTGTGAGAGTATCTGGTGAGCTCTGAACTCG |
| 20 | RFD-SA11 | ATGCCATCCTACCAACCATAACCGTTAGTTCATACAGTCGG CATCAGGAAGGGTCTGTTATTGATGGAGCTCTGAACTCG |
| 21 | RFD-SA12 | ATGCCATCCTACCAACCATAATGCAATCAACGTGTCTGTTC GTACTTATGGCAGTGGGTATCGTTGGAGCTCTGAACTCG |
| 22 | RFD-SA13 | ATGCCATCCTACCAACCACCGGAAGTTCATACAAGATTTGA CATCGGCATCTGGAGGCCTGTGGGGGAGCTCTGAACTCG |
| 23 | RFD-SA14 | ATGCCATCCTACCAACCACACCGCTGTCAGTGAATCAACGG ATGGATTGTTCGTCTGCGGTATAGGGAGCTCTGAACTCG |
| 24 | RFD-SA15 | ATGCCATCCTACCAACCACCAGACTCCTAGCGTTAGTTCAT GGACGCATAGTGGATGTGTCTCTAGGAGCTCTGAACTCG |
| 25 | RFD-SA16 | ATGCCATCCTACCAACTACACGGAAGAGGTGAAATACTACT AGATGGCAGGCTGATGTCCTCCGTGGAGCTCTGAACTCG |
| 26 | RFD-SA17 | ATGCCATCCTACCAACCATCAGAGCCGCCGTCTGTTCTCCA CAAGGATAGCACCGTGTGTGTCTGCGAGCTCTGAACTCG |
| 27 | RFD-SA18 | ATGCCATCCTACCAACACCCGACGAGGAGCCCCGTGTCATT TCTACAGATGGTTTATGCGGTCTCGGAGCTCTGAACTCG |
| 28 | RFD-SA19 | ATGCCATCCTACCAACCCGAAAAGGGCCATCGTGTCAGTTA TCAAACACGCATCTCAGGTCTCGATGAGCTCTGAACTCG |
| 29 | RFD-SA20 | ATGCCATCCTACCAACCACCGTCAGTAATGAATACAGTGAG GATCTGTGGGTGGCCATTCCCTAGGGAGCTCTGAACTCG |
| 30 | RFD-SA6T1B | <u>CTAATGAGTACCTACTGTCTTTTTTTTTTCTGGATGATCCT ATGAACTGACQRFGACCTCACTACCAAGATGCCATCCTACC</u> AACCACGAAGTACATTTCAAACTCATAACAATCCATCGGTT AGGTCCTGGTTGGTTTTTTTTTTB |
| 31 | TGNP-DNA | AGACAGTAGGTACTCATTAGTTTTTTTTTTTSH |
| 32 | TL-DNA | BTTTTTTTTTTTTAGTCAGTTCATAGGATCATCCAG |
| 33 | CGNP-DNA | ACCTGGGGGAGTATTGCGGAGGAAGGTTTTTTSH |
| 34 | CL-DNA | ACCTTCCTCCGCAATACTCCCCCAGGTTTTTB |
| 35 | RFD-SA6T1 | CTATGAACTG ACQRFGACCT CACTACCAAG ATGCCATCCT ACCAACCACG AAGTACATTT CAAACTCATA ACAATCCATC GGTTAGGTCC TGGTTGG |
| 36 | RFD-SA6T1FRQ | CTATGAACTG ACFROGACCT CACTACCAAG ATGCCATCCT ACCAACCACG AAGTACATTT CAAACTCATA ACAATCCATC GGTTAGGTCC TGGTTGG |
| 37 | RFD-SA6T1R | CTATGAACTG ACTRTGACCT CACTACCAAG ATGCCATCCT ACCAACCACG AAGTACATTT CAAACTCATA ACAATCCATC GGTTAGGTCC TGGTTGG |
| 38 | FS-RFD-SA6T1 | CTATGAACTGACQRFGACCTCACTACCAAGATGCCATCCTA CCAACCACGAAGTACATTTCAAACTCATAACAATCCATCGG TTAGGTCCTGGTGG |
| 39 | TGNP-DNA-core | AGACAGTAGGTACTCATTAGTTTTTTTTTT |

TABLE 1-continued

Sequences.

| SEQ ID NO: | Identifier | Sequence |
|---|---|---|
| 40 | TL-DNA-core | TTTTTTTTTTTAGTCAGTTCATAGGATCATCCAG |
| 41 | CGNP-DNA-core | ACCTGGGGGAGTATTGCGGAGGAAGGTTTTTT |
| 42 | CL-DNA-core | ACCTTCCTCCGCAATACTCCCCCAGGTTTTTT |
| 43 | RFD-SA6T1B-core | CTAATGAGTACCTACTGTCTTTTTTTTTTCTGGATGATCCT<br>ATGAACTGACQRFGACCTCACTACCAAGATGCCATCCTACC<br>AACCACGAAGTACATTTCAAACTCATAACAATCCATCGGTT<br>AGGTCCTGGTTGGTTTTTTTTTT |

Sequences are written 5'-3'. Abbreviations include: 50 nucleotide random region (N50), adenosine ribonucleotide (R), fluorescein-dT (F), DABCYL-dT (Q), glycol linker (L), random nucleotide (N), 20 adenosine (A20), biotinylate (B), thiol group (SH). The underlined portion in SEQ ID NO: 30 is the released short fragment that contains "QrA" (dabcyl-dT and adenine ribonucleotide). SEQ ID NO: 43 is SEQ ID NO: 30 without biotinylation at the 3' end.

Also provided is a biosensor for detecting *Staphylococcus aureus* comprising a catalytic nucleic acid probe described herein. In some embodiments, the catalytic nucleic acid probe comprises a nucleic acid molecule comprising (a) a first nucleic acid region that (i) is capable of binding to a microorganism target, and (ii) has catalytic activity for cleaving a substrate, optionally a detectable substrate, upon contacting with the microorganism target, and (b) a second nucleic acid region comprising the substrate. In some embodiments, the catalytic nucleic acid probe comprises a nucleic acid sequence selected from the group consisting of SEQ ID NOs: 2, 1, 3, 4, 11-30, 35-38, and 43, a functional fragment or modified derivative thereof. In some embodiments, the catalytic nucleic acid probe is an RNA-cleaving catalytic nucleic acid probe for cleaving the substrate that upon cleavage releases a fragment of the second nucleic acid region. In some embodiments, the solid support comprises a bead. In some embodiments, the solid support comprises agarose. In some embodiments, the fragment comprises a sensor zone test oligonucleotide binding domain and a test capture zone oligonucleotide binding domain, and wherein the sensor zone test oligonucleotide binding domain is capable of binding to a sensor zone test oligonucleotide by complementarity and the test capture zone oligonucleotide binding domain is capable of binding to a test capture zone oligonucleotide by complementarity. In some embodiments, the sensor zone test oligonucleotide is coupled to a detectable label. In some embodiments, the detectable label is a detectable label described herein. In some embodiments, the detectable label is a nanoparticle. In some embodiments, the nanoparticle is a gold nanoparticle. In some embodiments, the test capture zone oligonucleotide is coupled to a detectable label. In some embodiments, the detectable label is a detectable label described herein. In some embodiments, the detectable label is a nanoparticle. In some embodiments, the nanoparticle is a gold nanoparticle. In some embodiments, the sensor zone test oligonucleotide comprises or consists of a nucleic acid sequence of SEQ ID NO: 31 or 39. In some embodiments, the sensor zone test oligonucleotide comprises or consists of a nucleic acid sequence of SEQ ID NO: 31. In some embodiments, the sensor zone test oligonucleotide comprises or consists of a nucleic acid sequence of SEQ ID NO: 39. In some embodiments, the biosensor comprises a support. In some embodiments, the support is a solid or semi-solid support. In some embodiments, the support comprises beads, cellulose, or paper. In some embodiments, the support comprises agarose beads. In some embodiments, the catalytic nucleic acid probe is immobilized on a support. In some embodiments, the biosensor is comprised in a solution. In some embodiments, the solution comprises a buffer described herein.

Also provided is a lateral flow biosensor system comprising the catalytic nucleic acid probe or biosensor described herein. In some embodiments, the lateral flow biosensor system is for detecting presence of a microorganism target in a test sample. In some embodiments, the lateral flow biosensor system is for detecting presence of *Staphylococcus aureus* in a test sample. In some embodiments, the lateral flow biosensor system for detecting presence of a microorganism target in a test sample comprises:

a) a sample pad for applying the test sample in a running buffer to initiate a lateral flow process, wherein the catalytic nucleic acid probe is a catalytic nucleic acid described herein immobilized to a solid support, wherein the catalytic nucleic acid probe comprises the substrate, wherein the second nucleic acid region comprises a fragment comprising a sensor zone test oligonucleotide binding domain and a test capture zone oligonucleotide binding domain, b) a sensor zone comprising a sensor zone test oligonucleotide coupled to a nanoparticle and a sensor zone control DNA oligonucleotide coupled to a nanoparticle, wherein the sensor zone test oligonucleotide is capable of binding by complementarity to the sensor zone test oligonucleotide binding domain in the fragment to form a probe complex, c) a test capture zone comprising an immobilized test capture oligonucleotide, wherein the immobilized test capture oligonucleotide is capable of binding to the probe complex by complementarity to the test capture zone oligonucleotide binding domain in the fragment, d) a control capture zone comprising an immobilized control capture oligonucleotide, wherein the control capture oligonucleotide is capable of binding to the sensor zone control oligonucleotide, and e) an absorbent pad.

In some embodiments, the catalytic nucleic acid probe comprises a ribonucleotide linkage substrate and a fragment comprising a sensor zone test oligonucleotide binding domain and a test capture zone oligonucleotide binding domain. In some embodiments, the catalytic nucleic acid probe is comprised in the sample pad. In some embodiments, the catalytic nucleic acid probe comprises a nucleic acid molecule comprising (a) a first nucleic acid region that (i) is capable of binding to a microorganism target, and (ii) has catalytic activity for cleaving a substrate, optionally a detectable substrate, upon contacting with the microorganism target, and (b) a second nucleic acid region comprising the substrate. In some embodiments, the catalytic nucleic acid probe comprises a nucleic acid sequence selected from the group consisting of SEQ ID NOs: 2, 1, 3, 4, 11-30, 35-38, and 43, a functional fragment or modified derivative thereof. In some embodiments, the solid support comprises agarose beads. In some embodiments, the RNA-cleaving activity of the catalytic nucleic acid probe is activated by contacting the microorganism target, wherein upon activation, the catalytic nucleic acid probe is capable of cleaving the substrate, thereby releasing the fragment. In some embodiments, the catalytic nucleic acid probe is capable of cleaving the substrate at a ribonucleotide linkage site. In some embodiments, in the presence of the microorganism target, upon activation of the catalytic nucleic acid probe and the releasing of the fragment, whereby the fragment migrates to the sensor zone due to lateral flow of the running buffer. In some embodiments, upon migrating to the sensor zone, the sensor zone test oligonucleotide binding domain in the fragment binds by complementarity to the sensor zone test oligonucleotide, thereby forming a probe complex that migrates to the test capture zone due to lateral flow of the running buffer. In some embodiments, upon migrating to the test capture zone, the probe complex comprising the test capture zone oligonucleotide binding domain binds by complementarity to the test capture zone oligonucleotide, thereby generating a detectable signal by accumulation of the sensor zone test oligonucleotide coupled detectable label, optionally a nanoparticle, optionally a gold nanoparticle, at the test capture zone, indicating presence of *Staphylococcus aureus* in the test sample. In some embodiments, the sensor zone control oligonucleotide coupled to a detectable label, optionally a nanoparticle, optionally a gold nanoparticle, upon migrating from the sensor zone to the control capture zone by the lateral flow of the running buffer, binds to the control capture zone oligonucleotide, thereby generating a signal by accumulation of the capture zone oligonucleotide coupled detectable label at the control capture zone, indicating the lateral flow biosensor system functions correctly.

In some embodiments, the biosensor is immobilized to the agarose beads by biotin-streptavidin interaction. In some embodiments, the lateral flow biosensor system comprises nitrocellulose paper, a polymer support layer and a hydrophobic material. In some embodiments, the nanoparticle is a gold nanoparticle. In some embodiments, the test capture zone oligonucleotide and the control capture zone oligonucleotide are immobilized on a paper. In some embodiments, the paper is nitrocellulose paper. In some embodiments, the detectable label is a detectable label described herein. In some embodiments, the detectable label is a nanoparticle. In some embodiments, the nanoparticle is a gold nanoparticle. In some embodiments, the sensor zone test oligonucleotide comprises or consists of a nucleic acid sequence of SEQ ID NO: 31 or 39. In some embodiments, the sensor zone test oligonucleotide comprises or consists of a nucleic acid sequence of SEQ ID NO: 31. In some embodiments, the sensor zone test oligonucleotide comprises or consists of a nucleic acid sequence of SEQ ID NO: 39. In some embodiments, the sensor zone control nucleotide comprises or consists of a nucleic acid sequence of SEQ ID NO: 33 or 41. In some embodiments, the sensor zone control nucleotide comprises or consists of a nucleic acid sequence of SEQ ID NO: 33. In some embodiments, the sensor zone control nucleotide comprises or consists of a nucleic acid sequence of SEQ ID NO: 41. In some embodiments, the test capture zone oligonucleotide comprises or consists of a nucleic acid sequence of SEQ ID NO: 32 or 40. In some embodiments, the test capture zone oligonucleotide comprises or consists of a nucleic acid sequence of SEQ ID NO: 32. In some embodiments, the test capture zone oligonucleotide comprises or consists of a nucleic acid sequence of SEQ ID NO: 40. In some embodiments, the control capture zone oligonucleotide comprises or consists of a nucleic acid sequence of SEQ ID NO: 34 or 42. In some embodiments, the control capture zone oligonucleotide comprises or consists of a nucleic acid sequence of SEQ ID NO: 34. In some embodiments, the control capture zone oligonucleotide comprises or consists of a nucleic acid sequence of SEQ ID NO: 42. In some embodiments, the biosensor comprises a support. In some embodiments, the support is a solid or semi-solid support. In some embodiments, the support comprises beads, cellulose, or paper. In some embodiments, the support comprises agarose beads. In some embodiments, the catalytic nucleic acid probe is immobilized on a support. In some embodiments, the biosensor is comprised in a solution. In some embodiments, the solution comprises a buffer described herein. In some embodiments, the running buffer comprises HEPES. In some embodiments, the running buffer comprises HEPES and Tween 20. In some embodiments, the running buffer comprises HEPES, Tween 20, and SDS. In some embodiments, the running buffer comprises HEPES, NaCl, $MgCl_2$, and Tween 20. In some embodiments, the running buffer comprises HEPES, NaCl, $MgCl_2$, Tween 20, and SDS. In some embodiments, the running buffer comprises about 50 mM HEPES and about 0.1% Tween 20. In some embodiments, the running buffer comprises about 50 mM HEPES, about 0.1% Tween 20, and about 0.1% SDS. In some embodiments, the running buffer comprises about 50 mM HEPES, pH 7.5, about 150 mM NaCl, about 15 mM $MgCl_2$, about 0.1% Tween 20, and about 0.1% SDS.

Also provided is a method of detecting *Staphylococcus aureus* in a test sample, comprising:
   a) contacting the test sample with the biosensor described herein, wherein the catalytic nucleic acid probe comprises a detectable label,
   b) allowing cleavage of the catalytic nucleic acid probe if a microorganism target is present, thereby releasing the detectable label, and
   c) measuring a detectable signal if the portion of the catalytic nucleic acid probe comprising the detectable label is released,
   wherein the RNA cleavage activity of the catalytic nucleic acid probe is activated by a target from *Staphylococcus aureus*.

In some embodiments, the test sample comprises a clinical sample, a clinical matrix comprising methicillin-sensitive *Staphylococcus aureus* (MSSA), nasal mucus, scab exudate, or faeces.

Further provided is a method of detecting *Staphylococcus aureus* in a test sample, comprising:
   a) applying the test sample in a running buffer to the sample pad of the lateral flow biosensor system described herein,
   wherein the test sample comprises an analyte from *Staphylococcus aureus*, and wherein the analyte contacts the immobilized catalytic nucleic acid probe, optionally in the sample pad, and activates the catalytic nucleic acid probe which cleaves the substrate at a ribonucleotide cleavage site and releases the fragment comprising a sensor zone test oligonucleotide binding domain and a test capture zone oligonucleotide binding domain, b) allowing the running buffer to laterally flow into the sensor zone, and then the probe complex laterally flows to the test capture zone and the sensor zone control oligonucleotide laterally flows to the control capture zone, c) allowing the probe complex to produce a signal, d) detecting the signal in the test capture zone, e) allowing the sensor zone control oligonucleotide to produce a signal, and f) detecting the signal in the control capture zone, whereby the signal is indicative of the lateral flow biosensor system functioning correctly.

In some embodiments, the signal is a color change signal. In some embodiments, the color is indicative of amount of analyte. In some embodiments, wherein the test sample comprises a clinical sample, a clinical matrix comprising methicillin-sensitive *Staphylococcus aureus* (MSSA), nasal mucus, scab exudate, or faeces.

Further provided is a kit for detecting *Staphylococcus aureus*, wherein the kit comprises the biosensor or lateral flow biosensor system described herein, and instructions for use of the kit. In some embodiments, the kit further comprises at least one of a collection receptacle for storing the test sample, running buffer, a container for storing the runner buffer, a test sample collector, a bag, a label for identifying the test sample, and a package for the kit. In some embodiments, the collection receptacle for storing the test sample is a collection tube. In some embodiments, the running buffer is HEPES buffer. In some embodiments, the test sample collector is a swab. In some embodiments, the bag is a slide lock bag.

Hereinafter are provided Examples of specific embodiments and implementations for performing the methods and uses of the present disclosure. The Examples are provided for illustrative purposes only, and are not intended to limit the scope of the present disclosure in any way:

Examples

The following non-limiting examples are illustrative of the present disclosure:

Example 1. a DNAzyme Probe and Biosensor that Recognizes *Staphylococcus aureus*

Figure 1A:
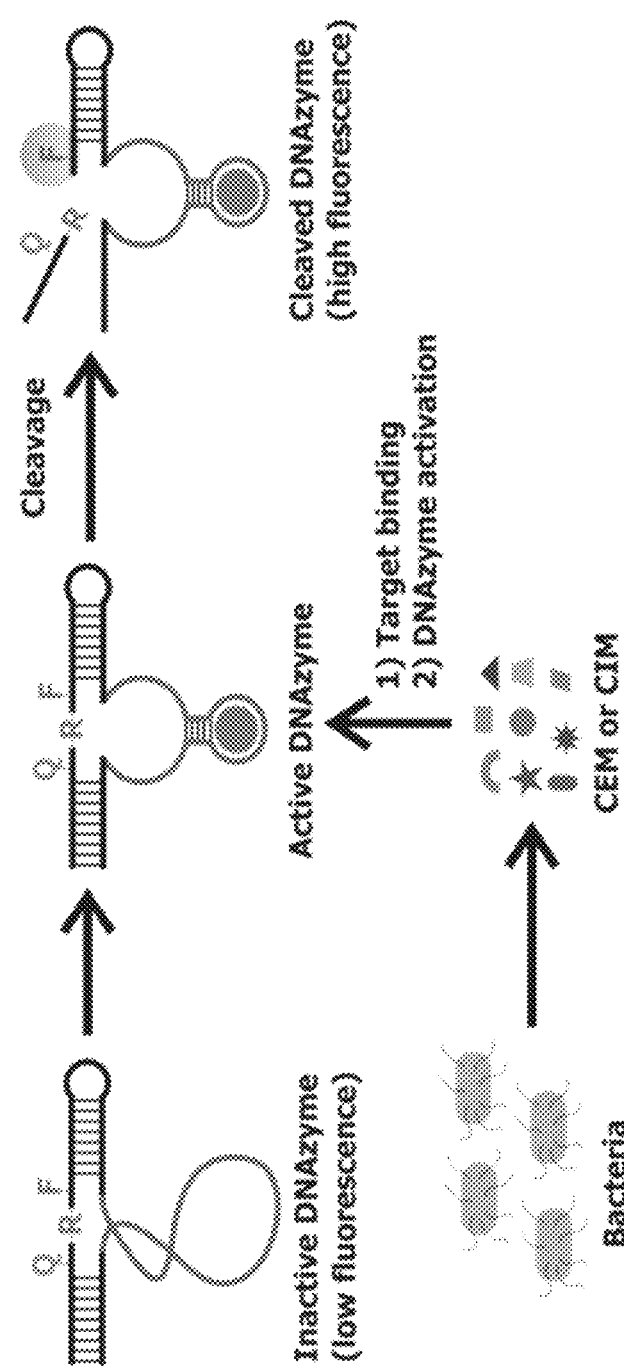
FIG. 1C shows cleavage reaction and real time fluorescence signaling of the truncated sequences of FIG. 1B, in an exemplary embodiment of the disclosure.
FIG. 1D shows fluorescence image of 10% denaturing polyacrylamide gel electrophoresis (dPAGE) of the reaction mixture of C after a 30 min reaction time, in an exemplary embodiment of the disclosure.

The development of bacterial bioassays with RNA-cleaving fluorogenic DNAzymes (RFDs) was introduced a decade ago for *E. coli* detection, [10] and since then, has been utilized for detection of numerous bacteria [11] using both fluorimetric [12] and colorimetric [13] assays. Such RFDs are isolated from random DNA libraries using a crude extra- or intra-cellular mixture (CEM or CIM) or with the combination of extra- and intra-cellular mixture (CEM-CIM) of the bacteria of interest, which catalyzes the cleavage of a fluorogenic DNA substrate at a single ribonucleotide embedded in the DNA substrate. This is followed by counterselection using other, related bacteria, where DNAw mes that do not cleave are carried forward to the next round of positive selection. Sequential rounds of positive and counterselection (up to 20) ultimately produce highly active and selective DNAwymes that cleave only in the presence of the intended bacterium. [10] In this Example, the non-directed CEM-CIM selection method was employed [10] to isolate RFDs for SA, as shown in FIG. 1A. A schematic illustration of the in vitro selection process and the DNA library, including the relevant oligonucleotide sequences, is provided in FIG. 2A, while the detailed procedure for the in vitro selection is provided in FIG. 2B. Briefly, in vitro selection was carried out using a random DNA library (DL) of ~1014 individual sequences which was ligated to a fluorogenic substrate (FS). This library was first used in a counterselection round using a mixture of CEM and CIM obtained from methicillin-sensitive *S. aureus* (MSSA), *E. coli* and *B. subtilis* to eliminate any non-specific DNAzyme molecules. The uncleaved molecules were then used for positive selection with the CEM-CIM mixture of MRSA, and the cleaved molecules were purified, amplified by PCR, and ligated to FS for use in the next round of selection. A significant amount of cleavage product was obtained after 9 rounds of positive selection, with counterselections being carried out every second round to achieve selectivity (FIG. 2C).

The population from round 9 was used for deep sequencing and the top 20 sequences (FIG. 3) were synthesized and tested for cleavage performance. The results presented in FIG. 4 showed that all RFDs cleaved FS in presence of the CEM-CIM of both MRSA and MSSA but did not cleave in presence of multiple other bacteria. These results showed that the RFDs obtained in selection were activated by a target that was present in both MRSA and MSSA, and thus could not discriminate between these bacteria (FIG. 5). These results showed that the DNAzyme was activated by a dominant target that is present in both MSSA and MRSA. Hence, additional rounds of selection or more stringent counterselection steps using a wider range of MSSA subtypes or higher concentrations of MSSA may be needed to achieve high selectivity for MRSA. It may also be necessary to use a different library or a purified target that is unique to MRSA to generate a more selective DNAwyme. Importantly, the DNAwyme still showed high selectivity against many non-SA bacteria, providing a useful molecular recognition element for detection of both methicillin-sensitive and methicillin-resistant SA strains. The RFD denoted as RFD-MRSA6 (i.e. RFD-SA06) had the highest cleavage activity (FIG. 4) and was selected for further investigation in this study.

Figures 1C, 1D:
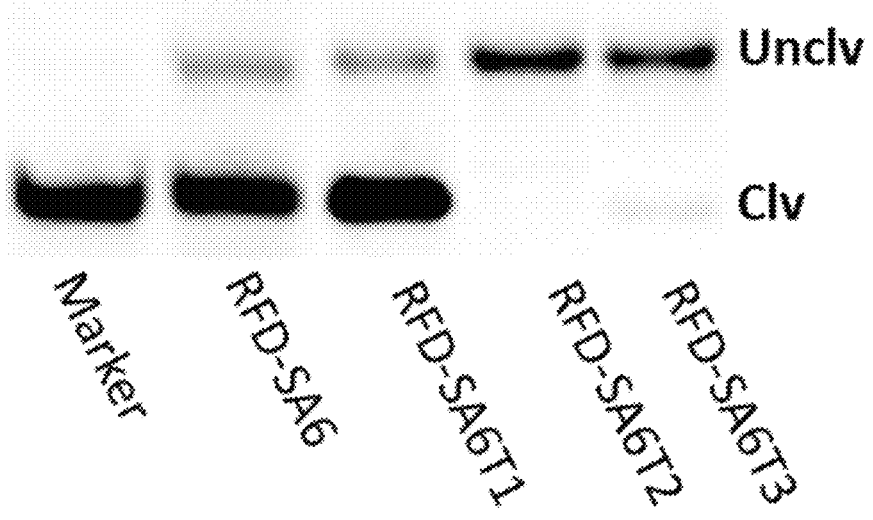

Truncation analysis was carried out to shorten the RFD-SA06 DNAzyme (FIG. 1B: SEQ ID NOs: 1-4). Removal of the 3' primer region had no impact on cleavage, while removal of the 5' primer region completely eliminated cleavage activity, indicating that the 5' primer region contained nucleotides essential to the catalytic function of the DNAzyme. One of the truncated versions, denoted as RFD-SA6T1 (SEQ ID NO: 2), cleaved the substrate, and generated a fluorescence signal equivalent to the full length DNAzyme, RFD-SA6 (FIG. 1C and FIG. 1D: SEQ ID NO: 1). RFD-SA6T1 contained 67 nucleotides and was used in all subsequent experiments. Predicted secondary structures of RFD-SA6 and the truncated RFD-SA6 have been provided FIG. 6 and show a substantial change in the secondary structure upon removal of the 5' primer, which correlates with loss of activity.

RFD-SAGT1 was then evaluated for fluorimetric detection of MRSA and MSSA which was spiked as a CEM-CIM mixture into nasal mucus samples. As a control, unspiked nasal mucus was used to evaluate the possibility of producing false positive signals from the nasal mucus alone. The results in FIG. 7A showed that RFD-SA6T1 produced a high fluorescence signal with the spiked nasal mucus but did not produce any fluorescence signal with nasal mucus alone. This is the first demonstration of an RFD operating in nasal mucus and shows that the RFD can both resist cleavage by nucleases that may be present in these samples, and also retain target-dependent cleavage even in the presence of DNA-binding proteins and other interfering species that may be present in nasal mucus. Additional gel-based data confirmed that the DNAzyme did not cleave in nasal mucus, indicating its resistance to degradation by nucleases in nasal mucus (see FIG. 8).

The specificity of RFD-SA6T1 against two strains of MSSA as well as different *Staphylococcus* species and other gram-positive and gram-negative bacteria was then evaluated (FIG. 7B), revealing that RFD-SA6T1 selectively produced strong fluorescence responses with all forms of SA, but did not respond to any other control bacteria, including several other *Staphylococcus* species. Corresponding dPAGE images of the cleavage reactions is provided in FIG. 9.

To test the sensitivity of the RFD-SAGT1, nasal mucus samples spiked with different numbers of MRSA cells were tested and indicated that an RFD-based fluorescence assay could produce a detectable fluorescence signal with $10^4$ CFU/mL within 30 min (FIG. 2C) and with $10^3$ CFU/mL after 80 min (FIG. 7D). This detection limit is comparable to that reported for other bacteria-sensitive DNAwymes, including those for *E. coli* ($10^4$ CFU/mL in 60 min) and *H. pylori* ($10^4$ CFU/mL in 60 min). Interestingly, the sensitivity of RFD-SAGT1 for detection of MRSA on a paper microwell plate improved by approximately 10-fold to $10^2$ CFU/mL using a 60 min reaction time (FIG. 7E), which was similar to previously reported paper-based assays for *E. coli*. [12b, 14] Similar improvements in detection limits have been reported and are based on increases in local concentration and reaction rates when moving solution-based assays to a paper surface. [14] Cleavage activity was also tested using intact cells and compared the cleavage results using different lysis conditions. The results showed cleavage activity was retained using intact cells and was similar to that obtained with lysed cells (FIG. 10).

To move the DNAzyme-based assay toward a simple and equipment free point-of-care test (POCT) for SA, integrating the assay with a LFD to produce a simple dipstick test was explored, as shown in FIG. 11. To date, there are only a few reports of DNAzyme-based LFDs, all of which are for metal ions. In this Example, the modified version of the cleavage product was utilized as a bridging strand. [15b] The LFD was first produced by printing streptavidin-bound biotinylated DNA oligonucleotides, denoted as TL-DNA for the test line and CL-DNA for the control line, onto a nitrocellulose strip (sequences of all oligonucleotides used for LFD fabrication are provided in FIG. 11A: adenine ribonucleotide is denoted as "rA" in this figure). The NCP strip was then attached to a backing card and cut into strips of 4×25 mm size, and a sample pad and a conjugate pad (4×10 mm) were attached along with an absorbent pad (4×20 mm), as shown in FIG. 11B. Finally, two sets of gold nanoparticle (GNP) conjugates were placed on the conjugate pad containing DNA complementary to either the DNAwyme cleavage fragment (test line nanoparticle, TGNP) or the DNA on the control line (named CGNP).

To make the RFD compatible with the LFD assay, the fluorescently-labelled substrate (FS) within the DNAzyme was modified by adding an extended sequence domain in the 5'-end (light grey domains in RFD-SA6T1B in FIG. 11A)

such that the 5'-end of the cleaved fragment of FS binds to the DNA strand on the TGNP and the 3'-end of the cleaved FS binds to the printed DNA strand on the test line, allowing the cleavage fragment to act as a bridging sequence between the TGNP and the DNA printed on the test line. The 3'-end of RFD-SAGT1 was modified with a biotin to immobilize the DNAzyme onto a streptavidin-modified agarose bead. In this way, the presence of SA in the test solution causes cleavage of the FS within the DNAzyme, releasing the bridging strand into solution, as shown in FIG. 11C, while uncleaved DNAzymes remain bound to the beads in solution.

Following the cleavage reaction, the LFD is placed into the test sample to allow the cleaved fragment of FS to travel up the strip and bridge between the TGNP and the test line DNA to form a positive test line along with a positive control line (FIG. 11D i). If only the control line is positive, the DNAzyme has not cleaved and the test is negative for SA (FIG. 11D part (ii)), while the absence of a control line is considered as an invalid result (FIG. 11D part (iii)).

Prior to testing the LFD with bacterial samples, the buffer conditions were improved to produce intense test and control lines when using 20% nasal mucus and a pre-cleaved product of the DNAzyme as the bridging sequence (underlined sequence, for example, the released short fragment that contains "QrA" (dabcyl-dT and adenine ribonucleotide) in RFD-SA6T1B (SEQ ID NO: 30) in FIG. 11A). 20% nasal mucus was chosen as higher amounts, such as 50% nasal mucus, produced high background signals (FIG. 12). The results are provided in FIG. 13. The improved buffer condition was determined to be 1× selection buffer containing 0.1% Tween20, which was used as the cleavage/running buffer. In addition, the sample pad was soaked in 0.1% SDS and dried to improve buffer flow. SDS in the sample pad also prevented non-specific interactions of the bridging sequence with any proteins present in the nasal mucus, avoiding false positive results (FIG. 13).

Using the improved conditions, it was next tested whether the DNAzyme could cleave and release the bridging sequence if the DNAzyme was directly immobilized on the LFD. In this case, the DNAzyme immobilized-LFD was directly immersed into the bacterial cell lysate mixed in the cleavage buffer in a tube. It was expected that once the targets along with the buffer moved up the strip, they would cleave the FS to free the bridging sequence to bridge TGNP and TL-DNA to produce a color. However, the results showed only a weak test line (FIG. 14 part (i)) when compared with the LFD where the cleavage was first carried out in the test sample followed by dipping the LFD into the reaction tube (FIG. 14 part (ii)), likely owing to insufficient time for DNAzyme cleavage. The two-step procedure (cleavage then immersion of the LFD) was therefore used for all subsequent assays. The F and Q labels were retained on the substrate, as reversal or removal of these labels eliminated cleavage activity (FIG. 15), indicating that the labels were required to obtain high cleavage activity.

The specificity of the LFD was first tested with cell lysate of $10^7$ CFU/mL of different Staphylococci. The cell lysates were spiked into 20% nasal mucus samples and the cleavage reactions were carried out for 10 min with each of the bacterial samples individually, followed by flowing the sample up the LFD for 20 min. An intense test line was observed on the LFD only for samples containing either MRSA or MSSA but not with other *Staphylococcus* species (FIG. 16A), indicating that the LFD maintained specificity and that the nasal mucus samples did not produce false positives or false negatives.

The sensitivity of the LFD with MRSA-spiked nasal mucus samples was also tested. Samples containing different numbers of bacterial cells were prepared as described for the solution-based fluorescence assay in FIG. 7C. The cleavage reactions with the bead-immobilized DNAzyme were conducted for 10 min with these samples and the LFDs were dipped into each tube to flow. Color of test lines on the LFDs were monitored after 20 min of flow. The results (FIG. 16B) revealed that the LFD produced a detectable test line with $10^5$ CFU/mL. Use of a longer cleavage reaction time produced background with non-target bacteria (FIG. 17). Although the detection limit with the LFD is lower than with the paper-based fluorescence assay, the shorter reaction time allowed the test to be done in 30 min and the signal could be read by eye without any instrument. In addition, the detection limit is below the asymptomatic level of SA in nasal mucus, which is reported to be as high as $10^6$ CFU/mL. [2d, 16] The storage stability of the LFD was also evaluated and was determined to be at least 6 months when stored desiccated at room temperature (FIG. 18).

Finally, the performance of the DNAzyme-based LFD was compared to Abbot™ Alere™ PBP2a lateral flow assay, which has been developed for testing MRSA colonies after plate culture. However, this commercial test produced very strong false positive signals (FIG. 19A) with 20% nasal mucus samples and even in pure buffer the limit of detection was only $10^7$ CFU/mL (FIG. 19B), and thus this test does not perform as well as the DNAzyme-based LFD.

In summary, a new DNAzyme for *S. aureus* was generated by in vitro selection and developed into solution and paper-based fluorescence assays and a rapid colorimetric LFD assay using the DNAzyme as a recognition element. In all cases the assay performed robustly, even in nasal mucus samples, and could provide test results in a minimally invasive manner in as little as 30 min. The LFD has the additional advantages of being portable and simple to use and generating a colorimetric readout that can be analyzed without equipment. This Example provides development of low-cost portable point-of-care diagnostics using DNAzyme probes for detecting pathogenic bacteria such as *Staphylococcus aureus* in clinical settings, especially in resource limited areas.

Example 2. Materials and Methods

DNA oligonucleotides. The random DNA library (DL) and the fluorogenic substrate (FS) were purchased from Keck Oligo Synthesis Facilities, Yale University (New Haven, CT). All other sequences including the PCR primers (FP, RP1, RP2), the ligation template (LT) and the DNAzyme sequences obtained after selection were purchased from Integrated DNA technologies (IDT: Coralville, IA). The sequences of DL (SEQ ID NO: 5), FS (SEQ ID NO: 10) and the primer are shown in FIG. 2A. DL contains 80 nucleotides (nt) including 50 random nucleotides denoted by N50 in the center and two constant regions of 16 nt and 14 nt at the 5' and 3' ends, respectively. Each random position, N, represents a 25% probability of A, C, G or T nucleotides. The 28-nt FS contains a riboadenosine nucleotide (R) that serves as the cleavage site. R is flanked by a fluorescein-dT (F) and a dabcyl-dT (Q). RP1 (SEQ ID NO: 7) and RP2 (SEQ ID NOs: 8 & 44 linked by a glycol linker) are two reverse primers used in PCR. RP2 contains a poly-A tail (A20: SEQ ID NO: 8) at the 5' end separated by a hexaethyleneglycol spacer (L, spacer 9 of IDT). The spacer prevents the poly-A tail from being amplified and thus produces a non-sense strand of the PCR product that is 20 nucleotides longer than the sense strand (DNAzyme), which allows purification of the desired sense sequence by denaturing polyacrylamide gel electrophoresis (dPAGE) (further details are provided below in the in vitro selection procedure). All the sequences were purified by 10% dPAGE before use.

Enzymes and chemicals. T4 DNA ligase and T4 polynucleotide kinase (PNK) including their respective buffers, as well as Y-PER™ and lysozyme were purchased from Thermo Scientific (Ottawa, ON, Canada). Biotools Thermophylus DNA polymerase was supplied by Mandel Scientific (Guelph, ON, Canada). Nasal mucus was obtained from Lee Biosolutions (Maryland Heights, MO). Unless otherwise noted, all other chemicals were purchased either from Bioshop Canada (Burlington, ON, Canada) or from Millipore-Sigma (Oakville, ON, Canada) and used without further purification. Water used in this Example was double-deionized (ddH$_2$O) and further purified using a Millipore Advantage A10 system (Millipore-Sigma) and autoclaved.

Bacterial cells. Two methicillin-sensitive *S. aureus* (MSSA: ATCC 25923, ATCC476), two strains of methicillin-resistant *S. aureus* (MRSA: ATCC 33591, ATCC 43300) and the other *Staphylococcus* strains including *S. lentus, S. saprophyticus, S. epidermidis, S. pasteuri* and *S. chromogenes* were purchased from the ATCC through Cederlane (Burlington, ON, Canada). *Bacillus subtilis* (BS) 168 was obtained from the *Bacillus* Genetic Stock Center (Columbus, OH, USA). *Escherichia coli* K12 (EC) is routinely maintained in the lab.

Preparation of Crude Extra- and Intra-Cellular Mixtures (CEM-CIM). CEM-CIM from the above bacteria were prepared as follows: *B. subtilis* was grown at 30° C. for 24 hours, while all other bacteria were grown in individual culture tubes in 5 mL tryptic soy broth (TSB) with continuous shaking at 37° C. and 250 rpm until the OD of the culture reached ~2, corresponding to approximately $10^8$ CFU/mL. The cells were pelleted by centrifugation at 10,000×g for 5 min at room temperature. The supernatants were collected in a fresh tube (denoted as CEM). The cell pellet was resuspended in 5 mL PBS including lysozyme (2 mg/mL) and incubated at 37° C. for 1 h. The cell suspension then underwent 3 freeze thaw cycles to ensure complete lysis. This suspension was then centrifuged at 10,000×g for 10 min. The clear supernatant (denoted as CIM) was collected and combined with the CEM. The mixture of CEM-CIM was passed through a 0.2 μm molecular cut-off size filter disc, aliquoted into microcentrifuge tubes (100 μL each) and stored at −20° C. until use.

In vitro Selection (see FIG. 2B for schematic illustration). Library preparation and selection (step I). In vitro selection was carried out with the full length DNA library (DL) covalently linked to the substrate FS. 1.0 nmole of DL was enzymatically ligated to FS as follows: the 5'-hydroxyl group of DL was phosphorylated using 15 units of T4 PNK for 45 min at 37° C. in 1×T4 polynucleotide kinase buffer A (PKB) in the presence of 1 mM ATP in a 100 μL reaction volume. The reaction was stopped by heating at 90° C. for 5 min. Equivalent amounts of FS and ligation template (LT: 1.0 nmole each) were added to this solution and the mixture was heated at 90° C. for 40 s and cooled to room temperature (RT) for 20 min. Then, 30 μL of 10×T4 DNA ligase buffer (T4LB), 30 μL of PEG4000 and 5 μL (25 U) of T4 DNA ligase (T4DL) were added. The volume was adjusted to 300 μL with ddH$_2$O. After pipette mixing, the reaction mixture was incubated at RT for 1 h.

Purification of ligated FS-DL (step II). The DNA molecules in the reaction mixture from step I were isolated by ethanol precipitation and the ligated FS-DL molecules were purified by 10% dPAGE and ethanol precipitation. The isolated DNA was dried by heating the tube at 95° C. keeping the lid open for 3 min.

Counterselection (step III). The DNA pool obtained in step II was dissolved in 200 μL of 1× selection buffer (1× SB) (50 mM HEPES, pH 7.5, 150 mM NaCl, 15 mM MgCl₂, and 0.01% Tween 20). 50 μL of a mixture of CEM-CIM of control bacteria (MSSA25923, EC and BS) was mixed with 50 μL of 2×SB and added to the FS-DL pool (total volume of 300 μL). After pipette mixing, the reaction mixture was incubated at room temperature for 2 h. The reaction was quenched by the addition 30 μL of 3.0 M NaOAc followed by 890 μL of cold ethanol.

Purification of uncleaved FS-DL (step IV). After ethanol precipitation, the reaction mixture was subjected to 10% dPAGE and the uncleaved FS-DL molecules were isolated as described in step II.

Positive selection (step V). The purified uncleaved full-length DNA pool, obtained from step IV, was dissolved in 100 μL of 1×SB. Immediately, 100 μL of CEM-CIM of MRSA 33591 in 1×SB (50 μL CEM-CIM-MRSA mixed with 50 μL 2× SB) was added to the DNA pool. After pipette mixing, the reaction mixture was incubated at room temperature for 60 min. The reaction was stopped by adding 20 μL of NaOAc followed by 590 μL of cold ethanol.

Isolation of cleaved products (step VI). After ethanol precipitation, the reaction mixture was subjected to 10% dPAGE. Before loading the sample in the gel, a marker was prepared by treating a small portion of the FS-DL with 0.25 M NaOH at 90° C. for 10 min. In the first few rounds, the cleaved product band in the gel image is not expected to be visible owing to a low concentration of cleaved DNA. Therefore, based on the position of the marker band, a portion of the gel below the uncleaved full length band was excised and the DNA molecules were isolated. After ethanol precipitation the DNA molecules were dissolved in 50 μL ddH₂O.

PCR1 (step VII). PCR was typically conducted in a volume of 50 μL with 10 μL of the isolated DNA molecules in step VI, 0.5 μM each of FP and RP1, 200 μM dNTPs, 1× PCR buffer (75 mM Tris-HCl, pH 9.0, 2 mM MgCl₂, 50 mM KCl, 20 mM (NH₄)₂SO₄) and 2.5 units of *Thermus thermophilus* DNA polymerase (Biotools, through Mandel Scientific: Guelph, ON, Canada). The amplification was conducted using the following thermocycling program: one cycle of 94° C. for 1 min: 13 cycles of 94° C. for 30 s, 50° C. for 45 s and 72° C. for 45 s (the numbers of amplification cycles between different selection rounds were adjusted, typically between 13 and 15 cycles, to achieve full amplification as assessed by 2% agarose gel electrophoresis): one cycle of 72° C. for 1 min.

PCR2 (step VIII). Because of the requirement for a large amount of DNA molecules in the selection, a second PCR step was conducted in 20 tubes of 50 μL each using the PCR1 product as a template. In this case, 1 μL of the PCR1 product was diluted to 20 μL, 1 μL of which was used in PCR2 using FP and RP2 primers following the same amplification program as PCR1.

Purification of DNAzyme-coding strand (step IX). The PCR product was concentrated by ethanol precipitation and subjected to 10% dPAGE. The DNA band of the sense-strand (shorter sequence, bottom band) was excised, and the DNA was eluted and stored at −20° C. as a dry pellet until use.

Ligation of PCR product to FS (step X) and repetition of steps II-X. The coding DNA strand prepared above (approximately 200 pmole, stored as a dried pellet) was ligated to FS as follows: The PCR product from the above step was phosphorylated in a 100 μL reaction volume with 10 units of PNK in the presence of 1 mM ATP in 1× PNK buffer for 40 min at 37° C. Note that the reaction volume of phosphorylation of PCR product for the subsequent rounds was constantly maintained at 100 μL. The kinase reaction was quenched by heating at 90° C. for 5 min and cooled down to RT for 20 min. Equal amounts of FS (SEQ ID NO: 10) and LT (SEQ ID NO: 9) (200 pmole each) were added to the PNK reaction mixture, mixed by vortexing, heated at 90° C. for 1 min and cooled to RT for 20 min. Then, 20 μL of T4LB, 20 μL of PEG4000 and 4 μL of T4DL were added sequentially and the volume of the reaction was adjusted to 200 μL with ddH₂O (ligations for the subsequent selection rounds were carried out in a 200 μL volume). After pipette mixing, the ligation reaction was conducted at RT for 1 h. After ethanol precipitation, the ligated DNA product was purified by 10% dPAGE and employed in the second round of negative and positive selections following the same procedure as described in the steps for the first round. A significant amount of cleavage product was obtained at round 9 of selection (FIG. 2C) and finally the DNA population of this round was amplified by PCR using specific primers for deep sequencing (Illumina deep sequencing at McMaster University central facility). The sequences were obtained as FASTQ file format and analyzed by Oracle VirtualBox sequence analyzer. Note that counterselections were applied every two rounds of selection to achieve selectivity.

Cleavage tests of top 20 sequences. The top 20 DNAzyme sequences including their names are shown in FIG. 3 (SEQ ID NOs: 1 and 11-29). Among them, the top 18 sequences were synthesized and tested for their cleavage performance. Each DNAzyme (1.0 nmole) was individually ligated to FS as described above in the selection procedure. After ligation and purification, the DNAzyme sequences were dissolved in ddH₂O, quantified using a Tecan NanoQuant™ plate and stored at −20° C. until use. The concentration of each DNAzyme was adjusted to 2.5 μM or 5 μM as required with ddH₂O. Each of the DNAzyme cleavage reactions were conducted in a 10 μL volume with some controls such as buffer alone, and other non-target bacteria to investigate the specificity. In greater detail, 1 μL of each DNAzyme was transferred to a microcentrifuge tube designated for each DNAw me sequence followed by addition of 5 μL of 2× SB. The cleavage reaction was started by adding 4 μL of ddH₂O in tube 1, and 4 μL of CEM-CIM of different bacteria (EC, BS. MSSA 25923 or MRSA 33591). After 45 min of incubation at RT the cleavage reactions were quenched by adding 10 μL of 2× gel loading buffer (GLB). The reaction mixtures were analyzed by 10% dPAGE and the gel was scanned for fluorescence bands using a ChemiDoc™ fluorescent imager (Bio-Rad, Hercules, CA).

Sequence truncation and cleavage test. Based on the cleavage performance of the top 18 DNAzymes (FIG. 4), RFD-SA06 was selected for nucleotide truncation to shorten the DNAzyme for subsequent experiments. For this purpose, the primers were deleted one at a time and together (FIG. 1B). 1000 pmole of the truncated sequences were ligated to the substrate FS as described above and purified by 10% dPAGE. The cleavage performance of each truncated sequence was assessed via real time fluorescence signal generation and by 10% dPAGE. The fluorescence signaling experiments were conducted in 96 well plate using a Tecan M1000 plate reader. First, 80 μL of each DNAzyme solution in 1× reaction buffer (50 nM final concentration of DNAzyme) was dispensed in a designated well of the 96-well plate for each DNAzyme. The plate was placed in the Tecan plate reader with the parameter settings: excitation 488 nm, emission 520 nm, reading from bottom, gain 150. Data was collected for 5 min and paused to add the samples. Next, 20 μL of CEM-CIM-MRSA 33591 in 1×SB (10) μL 2× SB mixed with 10 μL CEM-CIM) was added in each well. After adding the samples, data collection was resumed and continued for 30 min. The data was saved in an Excel as spread sheet and processed using Microsoft Excel software. 10 μL of each reaction mixture was transferred to a fresh tube and 10 μL of 2× GLB was added. These samples were subjected to 10% dPAGE and visualized using a Chemi-doc™ fluorescence imager.

Cleavage reactions of RFD-SA6T1 with all SA strains (see FIG. 5). The cleavage reactions were performed as described above. 1 μL (2 μM stock) of RFD-SAGT1 was transferred to a microcentrifuge tube designated for each bacterial strain, followed by sequential addition of 5 μL of 2× SB, 1 μL of the respective CEM-CIM mixture and 3 μL of ddH$_2$O. The reaction mixture was incubated for 30 min at RT and then quenched by adding 10 μL of 2×GLB. The reaction mixtures were analyzed by 10% dPAGE and the gel was scanned for fluorescence bands using a ChemiDoc™ fluorescent imager.

Signaling test with spiked nasal mucus (NM). Cleavage and signaling tests of RFD-SAGT1 were performed in 20% (final concentration in the reaction mixture) nasal mucus (NM) and the signaling was compared with the buffer alone. A mixture of 20% NM alone and a mixture of 20% NM including 10% of CEM-CIM was prepared in SB. 100 μL of these mixtures were dispensed in individual wells of a 96-well plate. The signal was acquired for 5 min followed by addition of 1 μL of DNAwyme (5 μM stock), followed by further monitoring for 30 min. The data was processed using Microsoft Excel software.

Selectivity of fluorescence assay in nasal mucus. Selectivity was also tested using RFD-SA6T1 through real time fluorescence signaling using a Tecan plate reader. In this case, 20% nasal mucus was spiked with different bacterial cell lines as described above to achieve a final concentration of 10$^7$ CFU/mL, and the real-time fluorescence signal was obtained over 30 min as described above.

Sensitivity of fluorescence assay in nasal mucus. To evaluate the sensitivity and detection limit of the DNAzyme-based fluorescence assay, the spiked NM of MRSA 33591 was prepared as follows: The cells were first cultured overnight in 3 mL in TSB and the number of cells was determined by conventional serial dilution method. The original overnight culture contained ~10$^8$ CFU/mL. After lysis, the supernatant was collected by centrifugation and this stock was considered to contain the same number of cells (~10$^8$ CFU/mL). This stock was then serially diluted in 10-fold steps in 8 tubes including 20% NM. Based on the number of cells in the original culture, the number of cells in the successive tubes are ~10$^7$, ~10$^6$, ~ 10$^5$. ~ 10$^4$ ~10$^3$, ~10$^2$, ~10$^1$ and ~10$^0$ CFU/mL respectively. 100 μL of each dilution was dispensed in a 96-well plate and data was collected for 5 min. Next, 1 μL of RFD-SAGT1 (5 μM) was added to each well and the fluorescence data was collected for 30 min or 80 min (for lower number of cells). The data was processed using Microsoft Excel software.

Stability of the DNAzyme in nasal mucus (see FIG. 8A, FIG. 8B, and FIG. 8C). For each reaction, 5 μL of 2× SB was dispensed in 6 separate microfuge tubes. 4 μL of ddH$_2$O was added to tube 1 and 4 ((labelled as buffer in FIG. 8B and FIG. 8C). 2 μL of Nasal mucus was added to remaining 4 tubes. 1 μL ddH$_2$O was added to tube 2 and 5 (labelled as NM in FIG. 8B and FIG. 8C) and 1 μL CEM-CIM was added to tube 3 and 6 (labelled as NM+CEM-MRSA in FIG. 8B and FIG. 8C). Next. 1 μL of FS-RFD-SA6T1 (SEQ ID NO: 38; from 2 μM stock) was added to the first 3 tubes that were designated for FS-RFD-SAGT1 (FIG. 8B) and 1 μL of FS (SEQ ID NO: 10; from 10 μM stock) was added to each 3 tubes that were designated for FS (FIG. 8C). The reaction mixtures were incubated at RT for 30 min and quenched by adding 2× GLB. The reaction mixtures were then analyzed by 10% dPAGE and imaged by using Bio-Rad Chemidoc™ gel imager.

Cleavage activity using intact and lysed cells (see FIG. 10). Cleavage reactions were conducted with RFD-SAGT1 in a 10 μL volume. Tube 1 (unlysed) contained 4 μL of 10$^8$ CFU/mL of intact MRSA 33591 in 5 μL of 2×SB. Tube 2, labelled as YPER™, contained 4 μL of the YPER™ lysed cells in 5 μL of 2×SB, which was incubated at RT for 20 min. Tube 3, labelled as lysozyme, contained 4 μL of lysozyme treated cell suspension and 5 μL of 2×SB. For lysozyme mediated lysis, cells (10) 8 CFU/mL) were treated with 2 mg/mL lysozyme in H$_2$O at RT for 20 min. In tube 4. labelled as sonication, 4 μL of sonicated cell suspension and 5 μL of 2×SB (10$^8$ CFU/mL cells in H$_2$O) was sonicated for 20 min. In tube 5, labelled as Heat, 4 μL of heat treated cells (10) 8 CFU/mL heated at 90)° C. for 5 min) was added to 5 μL of 2×SB. The last tube, labelled as polymixin B, contained 4 μL of polymixin B treated cell suspension (10$^8$ CFU/mL) and 5 μL of 2×SB, where cells had been treated with 1 mg/mL polymixin B at RT for 20 min. In each case, 1 μL of RFD-SA6T1 (2 μM stock in ddH$_2$O) was added to the tubes and the reaction mixture was incubated for 30 min at RT and then quenched by adding 10 μL of 2×GLB). The reaction mixtures were analyzed by 10% dPAGE and the gel was scanned for fluorescence bands using a ChemiDoc™ fluorescent imager.

Preparation of paper microwell plates. Paper microwell plates were produced by wax printing onto HF-120 nitro-cellulose paper (NCP) following the previously reported method (Ref 12c). Briefly, microzones of ~4 mm diameter were drawn in PowerPoint with a 6 mm inter-microzone distance, aligned in 8 rows and 12 columns. Wax was then printed on NCP using a Xerox Phaser 856ON wax printer. The wax-printed paper was heated at 120° C. for 2 minutes to melt the wax into the pores of the paper and provide hydrophobic barriers around the microzones. Next, the RFD-SA6T1 DNAzyme solution (5 μM in 1×SB buffer including 8% w/v pullulan) was dispensed in the microwell using a Biodot XYZ3060 dispense System (Irvine, CA) and dried at room temperature overnight.

Cleavage activity using DNAzymes with F/Q labels reversed or removed (see FIG. 15). 1 μL of each DNAzyme (original DNAzyme RFD-SA6T1 (SEQ ID NO: 35): RFD-SAGTIFRQ (SEQ ID NO: 36) with reversed labels and RFD-SAGT1R (SEQ ID NO: 37) with no labels) was transferred to a microcentrifuge tube designated for each DNAzyme sequence followed by addition of 5 μL of 2×SB. The cleavage reaction was started by adding 4 μL of ddH$_2$O in control tubes labelled as NC (Negative control) or 4 μL of CEM-CIM of MRSA 33591 or control bacteria. After 30) min of incubation at RT the cleavage reactions were quenched by adding 10 μL of 2×GLB. The reaction mixtures were analyzed by 10% dPAGE and the gel was scanned for fluorescence bands using a ChemiDoc™ fluorescent imager. Since RFD-SA6TIR did not contain a fluorophore, the gel was stained with 1× SYBR green for 15 min before imaging by ChemiDoc™ fluorescent imager.

Sensitivity tests on paper microwell plates. For sensitivity tests on the paper microwell plates, the spiked NM of MRSA 33591 was prepared in 20% nasal mucus in the same way as described above. 20 μL of each sample in the dilution series was added in the designated wells and allowed to react for 60 min. The plate was then scanned for fluorescence by using the Chemidoc™ imager. The images were processed and quantified by ImageJ software (ImageJ bundled with 64-bit Java 1.8.0_172) and the data were plotted using Microsoft Excel (FIG. 7E).

Development of Lateral Flow Devices: Step I. Synthesis of gold nanoparticles (GNPs). Gold nanoparticles of ~20 nm diameter were synthesized in a 100 mL volume. First, all glassware, including glass balloons, glass vials, stir bars, and condensers were washed with Aqua Regia (3:1 HCl: HNO₃) to remove all contaminants which can potentially lead to the aggregation of particles during synthesis or storage. Afterwards, all glassware was washed with copious amounts of ddH₂O and dried. Next, 100 mL of 2.2 mM sodium citrate was heated at 100° C. with a heating mantle in a 250 mL two-necked round-bottomed flask for 30 min under vigorous stirring. A cleaned condenser was placed in one neck to prevent solvent evaporation during synthesis. The second neck was closed using a rubber septum. Once boiling had commenced, 668 μL of HAuCl₄ (25 mM) was injected through the second neck. The color of the solution changed from yellow to dark blue and then to cherry red in 10 min. Heating at 100° C. was continued for a total of 25 min and then lowered to 90° C. for an additional 30 min. Next, 668 μL of HAuCl₄ (25 mM) was injected again and heating was continued at 90° C. for 30 min under vigorous stirring. Addition of HAuCl₄ (25 mM) was repeated two additional times under heating and stirring to produce ~20 nm GNP (0.8 nM). The resulting suspension was analyzed using UV-Vis to confirm their size and concentration.

Step II. Coupling DNAs with GNPs. TGNP-DNA and CGNP-DNA sequences (FIG. 11A: SEQ ID NOs: 10 and 30-34) were individually coupled with the GNPs and were designated to be captured in the test and control line, respectively. A 20 mL glass vial and stir bar were cleaned with 12 M NaOH and washed thoroughly with ddH₂O prior to use. 1 mL of each GNP (0.8 nM, 20 nm) was pipetted into the cleaned vials. 5 nmol of TGNP-DNA and CGNP-DNA were added to the respective vial. The GNP suspensions were incubated overnight in the dark at RT. Next, 20 μL of 1 M Tris-HCl (pH 7.5) and 50 μL of 1 M NaCl were added to the mixture and incubated overnight at RT. Following this, 100 μL of 1 M NaCl was added, mixed and incubated again overnight at RT. The coupled GNPs were then centrifuged at 6,000×g for 30 min and washed with RSS (10 mM Tris-HCl, sucrose 5% w/v, sodium chloride 0.07% w/v, pH 7.5) 3 times to remove any unbound DNA. The DNA coupled GNPs were resuspended in 1 mL of RSS to obtain a final concentration of ~0.8 nM. The vials were labelled as TGNP and CGNP and stored at 4° C. until use.

Step III. Printing and assembly of LFDs. Each LFD consisted of five components: 1) backing card, 2) printed nitro cellulose paper (NCP), 3) sample pad, 4) conjugate pad and 5) adsorbant pad. First, TL-DNA and CL-DNA (see the sequences in FIG. 11A) were printed on NCP as follows: 5 μM of streptavidin and 25 μM of either TL- and CL-DNA was mixed in 200 μL of PBS (pH 7.4) and incubated at RT for 30 min. After incubation, the streptavidin-DNA conjugate was passed through a centrifugal column (Amicon® Ultra-0.5 mL, Millipore-Sigma) with a 50K molecular cut off size for 10 min at 14,000 xg. The conjugate was washed twice with 200 μL of PBS. After washing, the concentrated streptavidin-DNA was recovered by placing the filter device upside down into a fresh micro centrifuge tube followed by centrifugation at 1,000×g for 2 min. The recovered streptavidin-DNA was diluted to a final volume of 100 μL in PBS. The streptavidin-DNA conjugates were named SA-TDNA and SA-CDNA respectively. These streptavidin-DNA conjugates were printed on the NCP (HF12004XSS, Millipore-Sigma, Etobicoke, Canada) using a Scienion S5 Sciflex Arrayer non-contact microarray printer (Phoenix, AZ). Before printing, the NCP was cut into a 25×300 mm pieces. The NCP was preconditioned at 60% humidity in the printer chamber. Both the control and test lines were printed ~22 mm (CL) and ~17 mm (TL) below the top edge of the NCP respectively with 5 mm interline distance. The diameter of each line was 0.5 mm. Each LFD line was printed using 600 drops with a drop size of 400 pL. After printing, the NCP was air dried for 1 h. This printed NCP was attached to the middle of a backing card and cut into strips of 4 mm wide using the Biodot Guillotine cutter. The absorbent pad (Ahlstrom grade 270)) was cut into 4×20 mm sizes and attached to the backing card just above the control line of the strips with 0.5 mm overlap with the NCP.

Glass fiber (G041 glass fiber from Millipore-Sigma) was cut into 4×10 mm pieces and one was used as a sample pad and the other was used as a conjugate pad. The conjugate pad was immersed in the GNP suspension and the sample pad glass fiber was soaked into resuspension solution containing 0.1% SDS. Both the sample and conjugate pads were dried for 2 h at room temperature. Next, the conjugate pad was attached just below the test line of the strip with 0.5 mm overlap with the NCP. The sample pad was attached just below the conjugate pad with a 0.5 mm overlap with the conjugate pad. This assembled final ready-to-use LFD strips contained (from the bottom): sample pad, conjugate pad, printed NCP and absorbent pad. The LFD strips were stored in a desiccator at room temperature until use.

Immobilization of DNAzyme on agarose beads. 100 μL of an agarose bead suspension (Pierce™, Fisher Scientific Inc., Burlington, ON, Canada) was placed in a microcentrifuge tube. The beads were washed with 300 μL of 1×SB 3 times and resuspended in 200 μL of 1×SB. Then, 100 pmole of the biotinylated DNAwyme was added to the bead suspension and incubated at room temperature for 1 h in a vertical rotator to prevent the beads from settling. After incubation, the mixture was spun down by a benchtop centrifuge (2,000 xg. 30s) and the clear supernatant was discarded. The bead complex was washed a total 5 times with 300 μL 1×SB to remove unbound DNAzymes and then resuspended in 200 μL of 1×SB and stored at 4° C. until use.

Improvement of LFD assays. Since the performance of the LFD depends on the release and smooth migration of the gold nanoparticles (GNPs) from the conjugate pad and successful hybridization of the DNAs on the GNPs with the printed DNAs on the NCP, the goal was to establish a condition that would prevent the GNPs from aggregating and allow them to smoothly migrate towards the absorbent pad. To establish the optimal buffer condition, the color generation on the TL (test line) and CL (control line) was tested using a pre-cleaved free bridging sequence. In the first condition as a control, neither the GNPs nor any components of the LFD were treated with any additive. The dipstick was submerged in a microfuge tube with 100 μL 1×SB including 20% nasal mucus and 50 nM bridging sequence. The migration of the GNPs and appearance of color in the test and control lines was monitored and pictures were taken after 5, 10 and 15 min of sample flow. Results showed that, although a signal appeared for both T and C lines at 15 min, the color intensity was not strong. Also, a significant amount of GNPs remained in the conjugate pad (FIG. 8, Condition 1). In the second condition, additional Tween20 was included in the buffer, assuming that a higher concentration of Tween20 would facilitate migration of GNPs along the LFD. Note that 1×SB always contains 0.01% Tween20. In this condition, Tween20 was increased by 10-fold (0.1% final concentration) in the buffer before inserting the dipstick. This condition helped the GNPs to flow smoothly and produced an intense color (Condition 2 in FIG. 8). In the third condition, the Tween20 was kept at 0.01% but the sample pad was soaked in 0.1% Tween20, dried and attached into the LFD and tested. The result showed that the GNPs remained aggregated in the conjugate pad (FIG. 8, Condition 3). In the fourth condition (Condition 4 in FIG. 8), the sample pad was soaked in 0.1% SDS and dried before attaching in the LFD. This condition improved the migration of the GNPs and produced slightly better color lines but not as intense as expected (FIG. 8, Condition 4). In the fifth condition, 0.1% Tween 20 was used in the cleavage reaction buffer and the sample pad was soaked in 0.1% SDS, dried and attached onto the LFD. This condition produced the best result (Condition 5 in FIG. 8) and this condition was selected for subsequent experiments.

Background Test of LFD in Different Concentrations of Nasal Mucus.

The background signal of the LFDs in different concentrations of unspiked nasal mucus (NM) was evaluated to determine the minimal dilution needed to retain low background on the test line. 100 μL of 50%, 20% and 10% nasal mucus was prepared in individual tubes in 1×SB (note that undiluted NM was too viscous to flow along the strip). The LFD was inserted in each of these tubes and allowed to run. The color of each LFD was captured after 20 min and processed using Image J software. Since the 20% nasal sample did not produce any background signal, this concentration was chosen for all the spiking experiments.

Cleavage of DNAzyme with MRSA cell lysate and performance test of the LFD. The DNAzyme-agarose bead complex was suspended in 90 μL of 1×SB including 0.1% Tween20 and 20% mucus in a microfuge tube. 20 μL of MRSA cell lysate (CEM-CIM) prepared in 1×SB (10 μL cell lysate with 10 μL 2×SB) was added to the DNAzyme-bead suspension. After pipette mixing, the reaction mixture was rotated to prevent sedimentation of the beads. After a 10 min reaction, the tube was briefly centrifuged using a bench top centrifuge at 3,000 rpm for 10 s. The LFD was then inserted into the tube. The color appearance was observed and captured by a cell phone camera (Samsung Galaxy S9) from a distance of 30 cm at 20 min. All images had the contrast enhanced using ImageJ. In the control experiment, only NM was used without adding the CEM-CIM mixture.

Direct cleavage of DNAzyme on the LFD. 50 μL of the DNAzyme-bead complex was briefly centrifuged. The supernatant was discarded. The DNAzyme-bead complex was suspended in 20 μL of 1×SB and dispensed onto the sample pad by pipetting. After air drying for 2 h, the sample pad was attached onto the LFD and directly inserted into the tube that contained 100 μL of 20% NM including 10% MRSA cell lysate (CEM-CIM) in 1×SB. After 20 min, the color was captured by a cell phone camera (Samsung Galaxy S9) from a distance of 30 cm at 20 min and processed by ImageJ software.

Effect of cleavage time on LFD performance (see FIG. 17). The DNAzyme-agarose bead complex was suspended in 90 μL of 1×SB including 0.1% Tween20 and 20% mucus in a microfuge tube. 20 μL of MRSA cell lysate (CEM-CIM) prepared in 1×SB (10 μL cell lysate with 10 μL 2×SB) was added to the DNAzyme-bead suspension. After pipette mixing, the reaction mixture was rotated to prevent sedimentation of the beads. After 30 min of reaction, the tube was briefly centrifuged using a bench top centrifuge at 3,000 rpm for 10 s. The LFD was then inserted into the tube. The color appearance was observed and captured by a cell phone camera (Samsung Galaxy S9) from a distance of 30 cm at 20 min. All images had the contrast enhanced using ImageJ. In the control experiment only, NM was used without adding the CEM-CIM mixture.

Specificity and sensitivity of the LFD. Spiked NM samples with different bacterial cells and samples with different numbers of MRSA cells were prepared in the same way as described earlier for fluorescence signaling assays with the DNAzyme. The cleavage and color development test with dipsticks were also performed using the optimal LFD assay conditions described above, with a 10 min cleavage reaction time and a 20 min LFD flow time.

Storage stability of LFDs (see FIG. 18). The LFD strips were prepared as described earlier in the experimental section and stored at RT in a desiccator. The performance was tested at different time points as indicated in FIG. 18 with the buffer alone and 20 nM bridging sequence containing buffer. The images were captured by a cell phone camera (Samsung Galaxy S9) from a distance of 30 cm at 20 min and processed by ImageJ software.

Performance test of the Abbott™ Alere™ LFD in buffer. 100 μL of 1×SB including 10% MRSA cell lysate (CEM-CIM) was prepared in a microcentrifuge tube. The Alere™ LFD was inserted into the tube. In the control experiment, only buffer without cell lysate was used. The LFDs were run for 20 min and the color of each LFD was captured by a cell phone camera (Samsung Galaxy S9) from a distance of 30 cm at 20 min. The images were processed using ImageJ software (far left two images in FIG. 12A).

Performance test of the Abbott™ Alere™ LFD in 20% nasal mucus. 100 μL of 20% nasal mucus and 10% MRSA cell lysate (CEM-CIM) in 1×SB was prepared in a microcentrifuge tube and the Alere™ LFD was inserted into the tube. In the control experiment, only 20% nasal mucus in 1×SB without cell lysate was used. The LFDs were run for 20 min and the color of each LFD was captured by a cell phone camera (Samsung Galaxy S9) from a distance of 30 cm at 20 min. The images were processed using ImageJ software (right two images in FIG. 12A).

Sensitivity test of the Abbott™ Alere™ LFD in buffer. Different numbers of MRSA33591 cells in 1×SB were prepared by serial dilution in 1×SB. 100 μL of the samples that contained $10^8$, $10^7$, $10^6$ and $10^5$ CFU/mL were transferred in fresh individual tubes. The Alere™ LFDs were inserted into the each tube and allowed to run. The images of the LFDs were captured by a cell phone camera (Samsung Galaxy S9) from a distance of 30 cm at 20 min and processed using ImageJ software (FIG. 12B).

While the present disclosure has been described with reference to examples, it is to be understood that the scope of the claims should not be limited by the embodiments set forth in the examples but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present disclosure is found to be defined differently in a document incorporated herein by reference, the definition provided herein is to serve as the definition for the term.

FULL CITATIONS FOR DOCUMENTS REFERRED TO IN THE DISCLOSURE

[1] a) P. N. Fonkwo, EMBO Rep. 2008, S13-17; b) M. Suhrcke, D. Stuckler, J. E. Suk, M. Desai, M. Senek, M. McKee, S. Tsolova, S. Basu, I. Abubakar, P. Hunter, B. Rechel, J. C. Semenza, PLOS One. 2011, 6, e20724; c) N. Uemura, S. Okamoto, S. Yamamoto, N. Matsumura, S. Yamaguchi, M. Yamakido, K. Taniyama, N. Sasaki, R. J. Schlemper, N. Eng. J. Med. 2001, 345, 784-789.

[2] a) J. Mehraj, W. Witte, M. K. Akmatov, F. Layer, G. Werner, G. Krause, Curr Top Microbiol Immunol. 2016, 398, 55-58: b) J. R. Fitzgerald, Infect Genet Evol. 2014, 21, 542-547; c) A. Schmidt, S. Bénard, S. Cyr, Surg Infect (Larchmt), 2015, 16, 428-435: d) A. Sakr, F. Bregeon, J. L. Mège, J. M. Rolain, O. Blin, Front Microbiol. 2018, 9, 2419.

[3] a) A. F. Brown, J. M. Leech, T. R. Rogers, R. M. McLoughlin, Front Immunol. 2014, 4, 507.

[4] a) C. Shi, Y. Xiao, Q. Zhang, Q. Li, F. Wang, J. Wu, N. Lin, BMC Infect Dis. 2018, 18, 508: b) H. Asgeirsson, A. Thalme, O. Weiland, Infect Dis (Lond). 2018, 50, 175-192: c) C. Gudiol, G. Cuervo, E. Shaw, M. Pujol, J. Carratalà, Expert Opin Pharmacother. 2017, 18, 1947-1963; d) C. K. Naber, Clin Infect Dis. 2009, 48, S231-7.

[5] a) M. Rubab, H. M. Shahbaz, A. N. Olaimat, D. H. Oh, Biosens Bioelectron. 2018, 105, 49-57: b) L. Marquez, T. H. Koy, C. R. Baker, J. Graf, E. M. Whaley, J. R. Campbell, Infect Control Hosp Epidemiol. 2018, 1-2: c) S. M. Puah, J. A. M. A. Tan, C. H. Chew, K. H. Chua, J Food Sci. 2018, 83, 2337-2342.

[6] a) S. Lakhundi, K. Zhang, Clin Microbiol Rev. 2018, 31, e00020-18; b) A. S. Lee, H. D. Lencastre, J. Garau, J. Kluytmans, S. Malhotra-Kumar, A. Peschel, S. Harbarth, Nat Rev Dis Primers. 2018, 4, 18033.

[7] V. Templier, Y. Roupioz., J Appl Microbiol. 2017, 123, 1056-1067.

[8] a) C. Zi, D. Zeng, N. Ling, J. Dai, F. Xue, Y. Jiang, B. Li, BMC Microbiol. 2018, 18, 132: b) M. O. Lara, T. C. Lucas, E. Kalapothakis, R. L. Thomasini, C. J. Machado, Rev Soc Bras Med Trop. 2018, 51, 528-532: c) W. Surasa, H. H. Peter, B. D. Kenneth, D. A. Lea, Diagn Microbiol Infect Dis., 2013, 75, 28-36.

[9] a) M. Zschöck, A. Nesseler, I. Sudarwanto, J Appl Microbiol. 2005, 98, 450-455: b) J Asante, B. A. Hetsa, D. G. Amoako, A. L. K. Abia, L. A. Bester, S. Y. Essack. Antibiotics (Basel), 2021, 10, 198; c) L. Essers, K. Radebold. J Clin Microbiol. 1980, 12, 641-643; d) C. J. Papasian, B. Garrison. Diagn Microbiol Infect Dis. 1999, 33, 201-203.

[10] a) M. M. Ali, S. D. Aguirre, H. Lazim, Y. Li. Angew. Chem. Int. Ed. Engl., 2011, 50, 3751-3754.

[11] a) Z. Shen, Z. Wu, D. Chang, W. Zhang, K. Tram, C. Lee, P. Kim, B. J. Salena, Y. Li, Angew. Chem. Int. Ed. Engl., 2016, 55, 2431-2434; b) M. M. Ali, M. Wolfe, K. Tram, J. Gu, C. D. M. Filipe, Y. Li, J. D. Brennan. Angew Chem Int Ed Engl. 2019, 58, 9907-9911: c) M. M. Ali, A. Slepenkin, E. Peterson, W. Zhao, Chembiochem. 2019, 20, 906-910; d) M. Rothenbroker, E. M. McConnell, J. Gu, M. L. Urbanus, S. E. Samani, A. W. Ensminger, C. D. M. Filipe, Y. Li. Angew Chem Int Ed Engl. 2021, 60, 4782-4788: e) E. M. McConnell, I. Cozma, Q. Mou, J. D. Brennan, Y. Lu, Y. Li, Chem Soc Rev. 2021, 50, 8954-8994.

[12] a) S. D. Aguirre, M. M. Ali, B. J. Salena, Y. Li, Biomolecules, 2013, 3, 563-577; b) M. M. Ali, C. L. Brown, S. Jahanshahi-Anbuhi, Y. Li, J. D. Brennan, Scientific Reports, 2017, 7, 12335: c) C. Ting, W. Yongcheng, Z. Ling-Li, W. Ye, T. Ye, H. A. John, W. A. David, Z. Ying-Lin, Z. Xin-Xiang, Chem Commun, 2019, 55, 7358-7361.

[13] K. Tram, P. Kanda, B. J. Salena, S. Huan, Y. Li, Angew. Chem. Int. Ed. Engl., 2014, 53, 12799-12802.

[14] M. Liu, C. Y. Hui, Q. Zhang, J. Gu, B. Kannan, S. Jahanshahi-Anbuhi, C. D. M. Filipe, J. D. Brennan, Y. Li. Angew Chem. Int. Ed. 2016, 55, 2709-2713.

[15] a) D. Mazumdar, J. Liu, G. Lu, J. Zhou, Y. Lu, Chem. Commun., 2010, 46, 1416-1418; b) Z. Fang, J. Huang, P. Lie, Z. Xiao, C. Ouyang, Q. Wu, Y. Wu, G. Liu, L. Zeng, Chem Commun. 2010, 46, 9043-9045; c) J. Chen, X. Zhou, L. Zeng, Chem. Commun., 2013, 49, 984-986.

[16] a) P. Verhoeven, F. Grattard, A. Carricajo, B. Pozzetto, P. Berthelot, J Clin Microbiol. 2010, 48, 4242-4244.

The invention claimed is:

1. A catalytic nucleic acid probe for detecting *Staphylococcus aureus*, wherein the catalytic nucleic acid probe comprises a nucleic acid molecule comprising (a) a first nucleic acid region that (i) is capable of binding to a microorganism target, and (ii) has catalytic activity for cleaving a substrate, optionally a detectable substrate, upon contacting with the microorganism target, and (b) a second nucleic acid region comprising the substrate, wherein the catalytic nucleic acid probe comprises a nucleic acid sequence selected from the group consisting of SEQ ID NOs: 2, 1, 30, 35-38, and 43.

2. The catalytic nucleic acid probe of claim 1, wherein the catalytic nucleic acid probe comprises a nucleic acid sequence selected from the group consisting of SEQ ID NOs: 35-38, and 43.

3. The catalytic nucleic acid probe of claim 1, wherein catalytic nucleic acid probe consists of SEQ ID NO: 2.

4. A biosensor comprising the catalytic nucleic acid probe of claim 1 coupled to a solid support, wherein the catalytic nucleic acid probe is an RNA-cleaving catalytic nucleic acid probe for cleaving the substrate that upon cleavage releases a fragment of the second nucleic acid region.

5. The biosensor of claim 4, wherein the solid support comprises a bead surface.

6. The biosensor of claim 4, wherein the solid support comprises agarose beads.

7. The biosensor of claim 4, wherein the fragment comprises a sensor zone test oligonucleotide binding domain and a test capture zone oligonucleotide binding domain, and wherein the sensor zone test oligonucleotide binding domain is capable of binding to a sensor zone test oligonucleotide by complementarity and the test capture zone oligonucleotide binding domain is capable of binding to a test capture zone oligonucleotide by complementarity.

8. A lateral flow biosensor system for detecting presence of a microorganism target in a test sample comprising:

a) a sample pad for applying the test sample in a running buffer to initiate a lateral flow process, wherein the catalytic nucleic acid probe of claim 1 is immobilized to a solid support, wherein the catalytic nucleic acid probe comprises the substrate, wherein the second nucleic acid region comprises a fragment comprising a sensor zone test oligonucleotide binding domain and a test capture zone oligonucleotide binding domain, b) a sensor zone comprising a sensor zone test oligonucleotide coupled to a nanoparticle and a sensor zone control DNA oligonucleotide coupled to a nanoparticle, wherein the sensor zone test oligonucleotide is capable of binding by complementarity to the sensor zone test oligonucleotide binding domain in the fragment to form a probe complex, c) a test capture zone comprising an immobilized test capture oligonucleotide, wherein the immobilized test capture oligonucleotide is capable of binding to the probe complex by complementarity to the test capture zone oligonucleotide binding domain in the fragment, d) a control capture zone comprising an immobilized control capture oligonucleotide, wherein the control capture oligonucleotide is capable of binding to the sensor zone control oligonucleotide, and e) an absorbent pad, optionally wherein the catalytic nucleic acid probe is comprised in the sample pad.

9. The lateral flow biosensor system of claim 8, wherein the solid support comprises agarose beads.

10. The lateral flow biosensor system of claim 9, wherein the catalytic nucleic acid probe is immobilized to the agarose beads by biotin-streptavidin interaction.

11. The lateral flow biosensor system of claim 8, wherein the lateral flow biosensor system comprises nitrocellulose paper, a polymer support layer and a hydrophobic material.

12. The lateral flow biosensor system of claim 8, wherein the nanoparticle is a gold nanoparticle.

13. The lateral flow biosensor system of claim 8, wherein the test capture zone oligonucleotide and the control capture zone oligonucleotide are immobilized on a paper.

14. The lateral flow biosensor system of claim 13, wherein the paper is nitrocellulose paper.

15. A method of detecting *Staphylococcus aureus* in a test sample, comprising:

a) contacting the test sample with the biosensor of claim 4, wherein the catalytic nucleic acid probe comprises a detectable label, b) allowing cleavage of the catalytic nucleic acid probe if a microorganism target is present, thereby releasing the detectable label, and c) measuring a detectable signal if the portion of the catalytic nucleic acid probe comprising the detectable label is released, wherein the RNA cleavage activity of the catalytic nucleic acid probe is activated by a target from *Staphylococcus aureus*.

16. The method of claim 15, wherein the test sample comprises a clinical sample, a clinical matrix comprising methicillin-sensitive *Staphylococcus aureus* (MSSA), nasal mucus, scab exudate, or faeces.

17. A method of detecting *Staphylococcus aureus* in a test sample, comprising:

a) applying the test sample in a running buffer to the sample pad of the lateral flow biosensor system in claim 8, wherein the test sample comprises an analyte from *Staphylococcus aureus*, and wherein the analyte contacts the immobilized catalytic nucleic acid probe, optionally in the sample pad, and activates the catalytic nucleic acid probe which cleaves the substrate at a ribonucleotide cleavage site and releases the fragment comprising a sensor zone test oligonucleotide binding domain and a test capture zone oligonucleotide binding domain, b) allowing the running buffer to laterally flow into the sensor zone, and then the probe complex laterally flows to the test capture zone and the sensor zone control oligonucleotide laterally flows to the control capture zone, c) allowing the probe complex to produce a signal, d) detecting the signal in the test capture zone, optionally the signal is a color change signal, optionally color is indicative of amount of analyte, e) allowing the sensor zone control oligonucleotide to produce a signal, and f) detecting the signal in the control capture zone, optionally the signal is a color change signal, whereby the signal is indicative of the lateral flow biosensor system functioning correctly.

18. The method of claim 17, wherein the test sample comprises a clinical sample, a clinical matrix comprising methicillin-sensitive *Staphylococcus aureus* (MSSA), nasal mucus, scab exudate, or faeces.

19. A kit for detecting *Staphylococcus aureus*, wherein the kit comprises the lateral flow biosensor system of claim 8, and instructions for use of the kit.

20. The kit of claim 19, further comprising at least one of a collection receptacle for storing the test sample, optionally a collection tube, running buffer, optionally HEPES buffer, a container for storing the running buffer, a test sample collector, optionally a swab, a bag optionally a slide lock bag, a label for identifying the test sample, and a package for the kit.

* * * * *

SEQUENCE LISTING

```
Sequence total quantity: 48
SEQ ID NO: 1              moltype = DNA  length = 80
FEATURE                   Location/Qualifiers
source                    1..80
                          mol_type = other DNA
                          organism = synthetic construct
SEQUENCE: 1
atgccatcct accaaccacg aagtacattt caaactcata acaatccatc ggttaggtcc   60
tggttggagc tctgaactcg                                               80

SEQ ID NO: 2              moltype = DNA  length = 67
FEATURE                   Location/Qualifiers
source                    1..67
                          mol_type = other DNA
                          organism = synthetic construct
SEQUENCE: 2
atgccatcct accaaccacg aagtacattt caaactcata acaatccatc ggttaggtcc   60
tggttgg                                                             67

SEQ ID NO: 3              moltype = DNA  length = 64
FEATURE                   Location/Qualifiers
source                    1..64
                          mol_type = other DNA
```

-continued

```
                              organism = synthetic construct
SEQUENCE: 3
cacgaagtac atttcaaact cataacaatc catcggttag gtcctggttg gagctctgaa    60
ctcg                                                                64

SEQ ID NO: 4              moltype = DNA   length = 51
FEATURE                   Location/Qualifiers
source                    1..51
                          mol_type = other DNA
                          organism = synthetic construct
SEQUENCE: 4
cacgaagtac atttcaaact cataacaatc catcggttag gtcctggttg g            51

SEQ ID NO: 5              moltype = DNA   length = 80
FEATURE                   Location/Qualifiers
source                    1..80
                          mol_type = other DNA
                          organism = synthetic construct
SEQUENCE: 5
atgccatcct accaacnnnn nnnnnnnnnn nnnnnnnnnn nnnnnnnnnn nnnnnnnnnn    60
nnnnnngagc tctgaactcg                                               80

SEQ ID NO: 6              moltype = DNA   length = 16
FEATURE                   Location/Qualifiers
source                    1..16
                          mol_type = other DNA
                          organism = synthetic construct
SEQUENCE: 6
atgccatcct accaac                                                   16

SEQ ID NO: 7              moltype = DNA   length = 14
FEATURE                   Location/Qualifiers
source                    1..14
                          mol_type = other DNA
                          organism = synthetic construct
SEQUENCE: 7
cgagttcaga gctc                                                     14

SEQ ID NO: 8              moltype = DNA   length = 20
FEATURE                   Location/Qualifiers
source                    1..20
                          mol_type = other DNA
                          organism = synthetic construct
misc_feature              20
                          note = The 3' of the deoxyadenosine is attached
                           through the hexaethylene glycol linker to SEQ ID NO: 44
SEQUENCE: 8
aaaaaaaaaa aaaaaaaaaa                                               20

SEQ ID NO: 9              moltype = DNA   length = 31
FEATURE                   Location/Qualifiers
source                    1..31
                          mol_type = other DNA
                          organism = synthetic construct
SEQUENCE: 9
gttggtagga tggcatcttg gtagtgaggt c                                 31

SEQ ID NO: 10             moltype = DNA   length = 30
FEATURE                   Location/Qualifiers
source                    1..30
                          mol_type = other DNA
                          organism = synthetic construct
modified_base             13
                          mod_base = OTHER
                          note = dabcyl deoxythymidine
modified_base             14
                          mod_base = OTHER
                          note = adenine ribonucleotide
modified_base             15
                          mod_base = OTHER
                          note = fluorescein deoxythymidine
SEQUENCE: 10
ctatgaactg actatgacct cactaccaag                                    30

SEQ ID NO: 11             moltype = DNA   length = 80
FEATURE                   Location/Qualifiers
source                    1..80
                          mol_type = other DNA
                          organism = synthetic construct
```

-continued

```
SEQUENCE: 11
atgccatcct accaacacaa ccaagagctg cttgtcagtg attcataaag gctcggtgat   60
gtctaggagc tctgaactcg                                              80

SEQ ID NO: 12          moltype = DNA   length = 79
FEATURE                Location/Qualifiers
source                 1..79
                       mol_type = other DNA
                       organism = synthetic construct
SEQUENCE: 12
atgccatcct accaacccaa gtggtccagt gcgtcgttca ttcatcttgc gtgactgtct   60
cactggagct ctgaactcg                                               79

SEQ ID NO: 13          moltype = DNA   length = 80
FEATURE                Location/Qualifiers
source                 1..80
                       mol_type = other DNA
                       organism = synthetic construct
SEQUENCE: 13
atgccatcct accaaccatg aggaagacgt agtgttagtt catccctggc acactgtgac   60
gtctcggagc tctgaactcg                                              80

SEQ ID NO: 14          moltype = DNA   length = 80
FEATURE                Location/Qualifiers
source                 1..80
                       mol_type = other DNA
                       organism = synthetic construct
SEQUENCE: 14
atgccatcct accaacacgg cgtaagttac acaagagttc ttcatggcat tagctggtct   60
ccgtgggagc tctgaactcg                                              80

SEQ ID NO: 15          moltype = DNA   length = 80
FEATURE                Location/Qualifiers
source                 1..80
                       mol_type = other DNA
                       organism = synthetic construct
SEQUENCE: 15
atgccatcct accaacacca caagctcacc gtcagttttg aaatattgca attgggtgca   60
gtctgggagc tctgaactcg                                              80

SEQ ID NO: 16          moltype = DNA   length = 80
FEATURE                Location/Qualifiers
source                 1..80
                       mol_type = other DNA
                       organism = synthetic construct
SEQUENCE: 16
atgccatcct accaaccata atgtcccagg tgtcagcgag taataagtca tctaaaggtc   60
tcctgggagc tctgaactcg                                              80

SEQ ID NO: 17          moltype = DNA   length = 80
FEATURE                Location/Qualifiers
source                 1..80
                       mol_type = other DNA
                       organism = synthetic construct
SEQUENCE: 17
atgccatcct accaaccacg agcgcaagtg tcaatcatta atccttggca tgcatgagcg   60
tccctggagc tctgaactcg                                              80

SEQ ID NO: 18          moltype = DNA   length = 80
FEATURE                Location/Qualifiers
source                 1..80
                       mol_type = other DNA
                       organism = synthetic construct
SEQUENCE: 18
atgccatcct accaaccacc aacaacagcc gtcaggttat gtgcgcatcg tgaggctctg   60
ctgttggagc tctgaactcg                                              80

SEQ ID NO: 19          moltype = DNA   length = 80
FEATURE                Location/Qualifiers
source                 1..80
                       mol_type = other DNA
                       organism = synthetic construct
SEQUENCE: 19
atgccatcct accaacccag agccacaagt gtcagtctca tttttgctcg tgtgagagta   60
tctggtgagc tctgaactcg                                              80

SEQ ID NO: 20          moltype = DNA   length = 80
FEATURE                Location/Qualifiers
source                 1..80
```

-continued

```
                            mol_type = other DNA
                            organism = synthetic construct
SEQUENCE: 20
atgccatcct accaaccata accgttagtt catacagtcg gcatcaggaa gggtctgtta   60
ttgatggagc tctgaactcg                                              80

SEQ ID NO: 21          moltype = DNA   length = 80
FEATURE                Location/Qualifiers
source                 1..80
                       mol_type = other DNA
                       organism = synthetic construct
SEQUENCE: 21
atgccatcct accaaccata atgcaatcaa cgtgtctgtt cgtacttatg gcagtgggta   60
tcgttggagc tctgaactcg                                              80

SEQ ID NO: 22          moltype = DNA   length = 80
FEATURE                Location/Qualifiers
source                 1..80
                       mol_type = other DNA
                       organism = synthetic construct
SEQUENCE: 22
atgccatcct accaaccacc ggaagttcat acaagatttg acatcggcat ctggaggcct   60
gtgggggagc tctgaactcg                                              80

SEQ ID NO: 23          moltype = DNA   length = 80
FEATURE                Location/Qualifiers
source                 1..80
                       mol_type = other DNA
                       organism = synthetic construct
SEQUENCE: 23
atgccatcct accaaccaca ccgctgtcag tgaatcaacg gatggattgt tcgtctgcgg   60
tatagggagc tctgaactcg                                              80

SEQ ID NO: 24          moltype = DNA   length = 80
FEATURE                Location/Qualifiers
source                 1..80
                       mol_type = other DNA
                       organism = synthetic construct
SEQUENCE: 24
atgccatcct accaaccacc agactcctag cgttagttca tggacgcata gtggatgtgt   60
ctctaggagc tctgaactcg                                              80

SEQ ID NO: 25          moltype = DNA   length = 80
FEATURE                Location/Qualifiers
source                 1..80
                       mol_type = other DNA
                       organism = synthetic construct
SEQUENCE: 25
atgccatcct accaactaca cggaagaggt gaaatactac tagatggcag gctgatgtcc   60
tccgtggagc tctgaactcg                                              80

SEQ ID NO: 26          moltype = DNA   length = 80
FEATURE                Location/Qualifiers
source                 1..80
                       mol_type = other DNA
                       organism = synthetic construct
SEQUENCE: 26
atgccatcct accaaccatc agagccgccg tctgttctcc acaaggatag caccgtgtgt   60
gtctgcgagc tctgaactcg                                              80

SEQ ID NO: 27          moltype = DNA   length = 80
FEATURE                Location/Qualifiers
source                 1..80
                       mol_type = other DNA
                       organism = synthetic construct
SEQUENCE: 27
atgccatcct accaacaccc gacgaggagc cccgtgtcat ttctacagat ggtttatgcg   60
gtctcggagc tctgaactcg                                              80

SEQ ID NO: 28          moltype = DNA   length = 80
FEATURE                Location/Qualifiers
source                 1..80
                       mol_type = other DNA
                       organism = synthetic construct
SEQUENCE: 28
atgccatcct accaacccga aaagggccat cgtgtcagtt atcaaacacg catctcaggt   60
ctcgatgagc tctgaactcg                                              80

SEQ ID NO: 29          moltype = DNA   length = 80
```

-continued

```
FEATURE                Location/Qualifiers
source                 1..80
                       mol_type = other DNA
                       organism = synthetic construct
SEQUENCE: 29
atgccatcct accaaccacc gtcagtaatg aatacagtga ggatctgtgg gtggccattc   60
cctagggagc tctgaactcg                                               80

SEQ ID NO: 30          moltype = DNA   length = 146
FEATURE                Location/Qualifiers
source                 1..146
                       mol_type = other DNA
                       organism = synthetic construct
modified_base          52
                       mod_base = OTHER
                       note = dabcyl deoxythymidine
modified_base          53
                       mod_base = OTHER
                       note = adenine ribonucleotide
modified_base          54
                       mod_base = OTHER
                       note = fluorescein deoxythymidine
modified_base          146
                       mod_base = OTHER
                       note = biotinylated thymidine
SEQUENCE: 30
ctaatgagta cctactgtct ttttttttc tggatgatcc tatgaactga ctatgacctc    60
actaccaaga tgccatccta ccaaccacga agtacatttc aaactcataa caatccatcg   120
gttaggtcct ggttggtttt tttttt                                        146

SEQ ID NO: 31          moltype = DNA   length = 30
FEATURE                Location/Qualifiers
source                 1..30
                       mol_type = other DNA
                       organism = synthetic construct
modified_base          30
                       mod_base = OTHER
                       note = thiol-bearing thymidine
SEQUENCE: 31
agacagtagg tactcattag ttttttttt                                     30

SEQ ID NO: 32          moltype = DNA   length = 34
FEATURE                Location/Qualifiers
source                 1..34
                       mol_type = other DNA
                       organism = synthetic construct
modified_base          1
                       mod_base = OTHER
                       note = biotinylated thymidine
SEQUENCE: 32
tttttttttt tagtcagttc ataggatcat ccag                              34

SEQ ID NO: 33          moltype = DNA   length = 32
FEATURE                Location/Qualifiers
source                 1..32
                       mol_type = other DNA
                       organism = synthetic construct
modified_base          32
                       mod_base = OTHER
                       note = thiol-bearing thymidine
SEQUENCE: 33
acctggggga gtattgcgga ggaaggtttt tt                                 32

SEQ ID NO: 34          moltype = DNA   length = 32
FEATURE                Location/Qualifiers
source                 1..32
                       mol_type = other DNA
                       organism = synthetic construct
modified_base          32
                       mod_base = OTHER
                       note = biotinylated thymidine
SEQUENCE: 34
accttcctcc gcaatactcc cccaggtttt tt                                 32

SEQ ID NO: 35          moltype = DNA   length = 97
FEATURE                Location/Qualifiers
source                 1..97
                       mol_type = other DNA
                       organism = synthetic construct
```

-continued

```
modified_base            13
                         mod_base = OTHER
                         note = dabcyl deoxythymidine
modified_base            14
                         mod_base = OTHER
                         note = adenine ribonucleotide
modified_base            15
                         mod_base = OTHER
                         note = fluorescein deoxythymidine
SEQUENCE: 35
ctatgaactg actatgacct cactaccaag atgccatcct accaaccacg aagtacattt   60
caaactcata acaatccatc ggttaggtcc tggttgg                            97

SEQ ID NO: 36           moltype = DNA   length = 97
FEATURE                 Location/Qualifiers
source                  1..97
                        mol_type = other DNA
                        organism = synthetic construct
modified_base           13
                        mod_base = OTHER
                        note = fluorescein deoxythymidine
modified_base           14
                        mod_base = OTHER
                        note = adenine ribonucleotide
modified_base           15
                        mod_base = OTHER
                        note = dabcyl deoxythymidine
SEQUENCE: 36
ctatgaactg actatgacct cactaccaag atgccatcct accaaccacg aagtacattt   60
caaactcata acaatccatc ggttaggtcc tggttgg                            97

SEQ ID NO: 37           moltype = DNA   length = 97
FEATURE                 Location/Qualifiers
source                  1..97
                        mol_type = other DNA
                        organism = synthetic construct
modified_base           14
                        mod_base = OTHER
                        note = adenine ribonucleotide
SEQUENCE: 37
ctatgaactg actatgacct cactaccaag atgccatcct accaaccacg aagtacattt   60
caaactcata acaatccatc ggttaggtcc tggttgg                            97

SEQ ID NO: 38           moltype = DNA   length = 97
FEATURE                 Location/Qualifiers
source                  1..97
                        mol_type = other DNA
                        organism = synthetic construct
modified_base           13
                        mod_base = OTHER
                        note = dabcyl deoxythymidine
modified_base           14
                        mod_base = OTHER
                        note = adenine ribonucleotide
modified_base           15
                        mod_base = OTHER
                        note = fluorescein deoxythymidine
SEQUENCE: 38
ctatgaactg actatgacct cactaccaag atgccatcct accaaccacg aagtacattt   60
caaactcata acaatccatc ggttaggtcc tggttgg                            97

SEQ ID NO: 39           moltype = DNA   length = 30
FEATURE                 Location/Qualifiers
source                  1..30
                        mol_type = other DNA
                        organism = synthetic construct
SEQUENCE: 39
agacagtagg tactcattag tttttttttt                                    30

SEQ ID NO: 40           moltype = DNA   length = 34
FEATURE                 Location/Qualifiers
source                  1..34
                        mol_type = other DNA
                        organism = synthetic construct
SEQUENCE: 40
tttttttttt tagtcagttc ataggatcat ccag                              34

SEQ ID NO: 41           moltype = DNA   length = 32
FEATURE                 Location/Qualifiers
```

-continued

```
source                   1..32
                         mol_type = other DNA
                         organism = synthetic construct
SEQUENCE: 41
acctgggggga gtattgcgga ggaaggtttt tt                                    32

SEQ ID NO: 42            moltype = DNA   length = 32
FEATURE                  Location/Qualifiers
source                   1..32
                         mol_type = other DNA
                         organism = synthetic construct
SEQUENCE: 42
accttcctcc gcaatactcc cccaggtttt tt                                     32

SEQ ID NO: 43            moltype = DNA   length = 146
FEATURE                  Location/Qualifiers
source                   1..146
                         mol_type = other DNA
                         organism = synthetic construct
modified_base            52
                         mod_base = OTHER
                         note = dabcyl deoxythymidine
modified_base            53
                         mod_base = OTHER
                         note = adenine ribonucleotide
modified_base            54
                         mod_base = OTHER
                         note = fluorescein deoxythymidine
SEQUENCE: 43
ctaatgagta cctactgtct tttttttttc tggatgatcc tatgaactga ctatgacctc   60
actaccaaga tgccatccta ccaaccacga agtacatttc aaactcataa caatccatcg   120
gttaggtcct ggttggtttt tttttt                                          146

SEQ ID NO: 44            moltype = DNA   length = 14
FEATURE                  Location/Qualifiers
source                   1..14
                         mol_type = other DNA
                         organism = synthetic construct
misc_feature             1
                         note = The 5' of the deoxycytidine is attached through
                          the glycol linker to SEQ ID NO: 8
SEQUENCE: 44
cgagttcaga gctc                                                         14

SEQ ID NO: 45            moltype = DNA   length = 110
FEATURE                  Location/Qualifiers
source                   1..110
                         mol_type = other DNA
                         organism = synthetic construct
SEQUENCE: 45
ctatgaactg actatgacct cactaccaag atgccatcct accaaccacg aagtacattt   60
caaactcata acaatccatc ggttaggtcc tggttggagc tctgaactcg               110

SEQ ID NO: 46            moltype = DNA   length = 97
FEATURE                  Location/Qualifiers
source                   1..97
                         mol_type = other DNA
                         organism = synthetic construct
SEQUENCE: 46
ctatgaactg actatgacct cactaccaag atgccatcct accaaccacg aagtacattt   60
caaactcata acaatccatc ggttaggtcc tggttgg                             97

SEQ ID NO: 47            moltype = DNA   length = 94
FEATURE                  Location/Qualifiers
source                   1..94
                         mol_type = other DNA
                         organism = synthetic construct
SEQUENCE: 47
ctatgaactg actatgacct cactaccaag cacgaagtac atttcaaact cataacaatc   60
catcggttag gtcctggttg gagctctgaa ctcg                                94

SEQ ID NO: 48            moltype = DNA   length = 81
FEATURE                  Location/Qualifiers
source                   1..81
                         mol_type = other DNA
                         organism = synthetic construct
```

-continued

SEQUENCE: 48
ctatgaactg actatgacct cactaccaag cacgaagtac atttcaaact cataacaatc  60
catcggttag gtcctggttg g                                            81